(12) United States Patent
Chuang et al.

(10) Patent No.: US 11,913,025 B2
(45) Date of Patent: Feb. 27, 2024

(54) ANTIGEN-SPECIFIC T CELLS AND USES THEREOF

(71) Applicant: CYTOARM CO., LTD, Taipei (TW)

(72) Inventors: Kuo-Hsiang Chuang, Taipei (TW); Yi-Jou Chen, Keelung (TW); Michael Chen, Hsinchu County (TW)

(73) Assignee: Cytoarm Co., Ltd, Taipei (TW)

( * ) Notice: Subject to any disclaimer, the term of this patent is extended or adjusted under 35 U.S.C. 154(b) by 360 days.

(21) Appl. No.: 16/497,805

(22) PCT Filed: Mar. 29, 2018

(86) PCT No.: PCT/CN2018/081084
§ 371 (c)(1),
(2) Date: Sep. 26, 2019

(87) PCT Pub. No.: WO2018/177371
PCT Pub. Date: Oct. 4, 2018

(65) Prior Publication Data
US 2021/0139851 A1 May 13, 2021

Related U.S. Application Data

(60) Provisional application No. 62/478,280, filed on Mar. 29, 2017.

(51) Int. Cl.
| | |
|---|---|
| *A61K 35/17* | (2015.01) |
| *C12N 5/0783* | (2010.01) |
| *A61P 35/00* | (2006.01) |
| *C07K 16/28* | (2006.01) |
| *C07K 16/30* | (2006.01) |
| *C07K 16/32* | (2006.01) |
| *C07K 16/40* | (2006.01) |

(52) U.S. Cl.
CPC ............ *C12N 5/0638* (2013.01); *A61K 35/17* (2013.01); *A61P 35/00* (2018.01); *C07K 16/2809* (2013.01); *C07K 16/2827* (2013.01); *C07K 16/2863* (2013.01); *C07K 16/30* (2013.01); *C07K 16/3007* (2013.01); *C07K 16/3069* (2013.01); *C07K 16/32* (2013.01); *C07K 16/40* (2013.01); *C07K 2317/24* (2013.01); *C07K 2317/31* (2013.01); *C07K 2317/55* (2013.01); *C07K 2317/622* (2013.01); *C12N 2501/15* (2013.01); *C12N 2501/2302* (2013.01); *C12N 2501/2307* (2013.01); *C12N 2501/515* (2013.01); *C12N 2501/599* (2013.01)

(58) Field of Classification Search
CPC .......................... A61K 35/17; A61K 2039/505
See application file for complete search history.

(56) References Cited

FOREIGN PATENT DOCUMENTS

WO    WO-2012158818 A2 * 11/2012    ........ A61K 39/39558

OTHER PUBLICATIONS

Norman (Ther. Drug Monit. Dec. 1995; 17 (6): 615-20).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Winkler et al. (J. Immunol. Oct. 15, 2000; 165 (8): 4505-4514).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Renders et al. (Clin. Exp. Immunol. Sep. 2003; 133 (3): 307-9).*
June (J. Clin. Invest. Jun. 1, 2007; 117 (6): 1466-76).*
Brishwein et al. (J. Immunother. Nov.-Dec. 2007; 30 (8): 798-807).*
Grabert et al. (Clin. Cancer Res. Jan. 15, 2006; 12 (2): 569-76).*
Link et al. (Int. J. Cancer. Jul. 17, 1998; 77 (2): 251-6).*
Sen et al. (J. Hematother. Stem Cell Res. Apr. 2001; 10 (2): 247-60).*
Davol et al. (Clin. Prostate Cancer. Sep. 2004; 3 (2): 112-21).*
Wolf et al. (Drug Discov. Today. Sep. 15, 2005; 10 (18): 1237-44).*
Yankelevich et al. (Pediatr. Blood Cancer. Dec. 15, 2012; 59 (7): 1198-205).*
Zitron et al. (BMC Cancer. Feb. 22, 2013; 13: 83; pp. 1-14).*
Lum et al. (Clin. Cancer Res. May 15, 2015; 21 (10): 2305-14).*
Gall et al. (Exp. Hematol. Apr. 2005; 33 (4): 452-9).*
Freudenberg et al. (Front. Immunol. Feb. 2, 2018; 9: 125; pp. 1-13).*
Guo et al. (J. Immunol. Aug. 15, 2008; 181 (4): 2285-91; author manuscript; pp. 1-18).*
Thakur et al. (Front. Immunol. Jul. 5, 2021; 12: 690437; pp. 1-13).*
Bhutani et al. (Curr. Opin. Hematol. Nov. 2015; 22 (6): 476-83).*
Grützkau et al. (Cytometry A. Jul. 2010; 77 (7): 643-7).*
Reusch et al. (Clin. Cancer Res. Jan. 1, 2006; 12 (1): 183-90).*
Lum et a. (Oncoimmunology. Jun. 10, 2020; 9 (1): 1773201; pp. 1-11).*

* cited by examiner

Primary Examiner — Stephen L Rawlings
(74) Attorney, Agent, or Firm — NZ Carr Law Office

(57) ABSTRACT

Provided are methods of inducing differentiation and/or proliferation of T cells and uses thereof. In the present method, peripheral blood mononuclear cells (PBMCs) isolated from a subject are cultivated with bi-specific antibodies (BsAbs) in a culture medium so as to differentiate the PBMCs into the T cells. Each of the T cells has an anti-tumor antigen moiety and an anti-CD3 moiety on its surface. Also provided are methods and pharmaceutical kits for treating subjects suffering from cancers.

2 Claims, 32 Drawing Sheets

Specification includes a Sequence Listing.

(A)

(B)

(C)

(D)

(A)

(B)

(C)

(D)

ANTIGEN-SPECIFIC T CELLS AND USES THEREOF

CROSS-REFERENCE OF RELATED APPLICATION

This application is a U.S. National Stage Filing under 35 U.S.C. 371 from International Patent Application Serial No. PCT/CN2018/081084, entitled "ANTIGEN-SPECIFIC T CELLS AND USES THEREOF," filed Mar. 29, 2018, and published on Oct. 4, 2018. The PCT application claims priority to U.S. Application No. 62/478,280, filed on Mar. 29, 2017. The contents of these applications are incorporated herein by reference in their entirety.

BACKGROUND OF THE INVENTION

1. Field of the Invention

The present disclosure relates to treatments of cancers. Specifically, the present disclosure relates to antigen-specific T cells and their uses for suppressing the growth or metastasis of cancers.

2. Description of Related Art

T cells are of a rare cell population, in which merely 5 to 10% of $CD4^+$ T cells are found in peripheral blood. Proliferation of T cells can be promoted by stimulating with cytokines, such as IL-2, IL-4, and IL-5, in addition to anti-CD28 antibodies. However, the level is still insufficient for any clinical applications, such as application that involves increasing the number of activated T cells and transferring them back to human (e.g., chimeric antigen receptor (CAR) T cell therapy).

One way to activate T cell or to induce differentiation of T cell is via activating signal transduction pathway mediated by CD3 using anti-CD3 antibodies. To date, the activation of human T cells via the CD3 antigen complex have been carried out with mouse anti-human IgG2a isotype (OKT3) monoclonal antibody, which induces a mitogenic response equal to that of concanavalin A (Con A). However, one major concern of a non-human origin monoclonal antibody (e.g., murine OKT3 Ab) is its immunogenicity to the recipient, in some cases, caused dangerous allergic reactions. Human T cells activated by murine OKT3 Abs inevitably carry murine protein fragments on the surfaces, thereby posting a potential threat to their recipient.

In view of the foregoing, there remains in the related field a need of less immunogenic antibodies that may replace murine OKT3 antibodies, and a need of an improved method of activating human T cells without using murine OKT3 antibodies.

SUMMARY

The present disclosure provides T cells differentiated and proliferated by BsAbs of the present disclosure, and their uses for treating cancers.

Accordingly, it is the first objective of the present disclosure to provide a method of inducing differentiation and/or proliferation of T cells, in which each T cells has anti-tumor antigen moiety and an anti-CD3 moiety on its surface. The method includes, culturing peripheral blood mononuclear cells (PBMCs) with bi-specific antibodies (BsAbs) in a culture medium so as to differentiate the PBMCs into the T cells, in which each BsAbs comprises a tumor antigen binding site that corresponds to the anti-tumor antigen moiety of the T cell, and a CD3 binding site that corresponds to the anti-CD3 moiety of the T cell, and the BsAbs are not murine OKT3 antibodies.

According to embodiments of the present disclosure, each BsAbs is in the structure of single chain variable fragment (scFv), an antigen-binding fragment (Fab), a $F(ab')_2$ or an IgG.

According to embodiments of the present disclosure, the tumor antigen binding site of each BsAbs binds to any of epidermal growth factor receptor (EGFR), programmed cell death-ligand 1 (PD-L1), or prostate specific membrane antigen (PSMA).

According to optional embodiments of the present disclosure, the culture medium may further comprise a cytokine selected from the group consisting of IL2, TGF-β, or a combination thereof. In one preferred embodiment, the culture medium comprises both of the IL2 and the TGF-β, and the T cells thus formed are regulator T cells.

According to embodiments of the present disclosure, in each BsAbs, the tumor antigen binding site comprises a tumor antigen scFv at least 90% identical to any of SEQ ID NOs: 69, 77, 84, 90, 96, 102, 108, 114, or 120; and the CD3 binding site comprises an anti-CD3 VL-Ck domain at least 90% identical to SEQ ID NO: 67, and an anti-CD3 VH-CH1 domain at least 90% identical to SEQ ID NO: 68.

According to embodiments of the present disclosure, in each BsAbs, the tumor antigen binding site comprises an anti-tumor antigen scFv at least 90% identical to any of SEQ ID NOs: 70, 78, 85, 91, 97, 109, or 121; and the CD3 binding site comprises an anti-CD3 scFv at least 90% identical to SEQ ID NOs: 66 or 79.

According to embodiments of the present disclosure, in each BsAbs, the tumor antigen binding site comprises an anti-tumor antigen VL-Ck domain at least 90% identical to SEQ ID NOs: 64, 75, 82, 88, 94, 100, 106, 112, or 118; and an anti-tumor antigen VH-CH1 domain at least 90% identical to SEQ ID NOs: 65, 76, 83, 89, 95, 101, 107, 113, or 119; and the CD3 binding site comprises an anti-CD3 scFv at least 90% identical to SEQ ID NO: 66 or 79.

According to embodiments of the present disclosure, in each BsAbs, the tumor antigen binding site comprises an anti-tumor antigen VL-Ck domain at least 90% identical to SEQ ID NOs: 73, 80, 86, 92, 98, 104, 110, 116 or 122, and an anti-tumor antigen VH-CH1-Fc domain at least 90% identical to SEQ ID NOs: 74, 81, 87, 93, 99, 105, 111, 117, or 123; and the CD3 binding site comprises an anti-CD3 VL-Ck domain at least 90% identical to SEQ ID NO: 71, and an anti-CD3 VH-CH1-Fc domain at least 90% identical to SEQ ID NO: 72.

In practice, antigen-specific T cells prepared in accordance by the present method may be mixed with the humanized BsAb described above to form a mixture, the mixture is then administered to a subject in need of a treatment of cancer.

Accordingly, it is the third objective of the present disclosure to provide a pharmaceutical kit for the treatment of cancer. The pharmaceutical kit comprises, the T cells differentiated and proliferated in accordance with the present method, and a humanized BsAb of the present disclosure.

It is the fourth objective of the present disclosure to provide a method of treating a subject afflicted with a cancer. The method includes the step of, administered to the subject an effective amount of the T cells prepared by the method described above, or an effective amount of a murine OKT3 T cell modified with the present BsAb.

According to some embodiments, the murine OKT3 T cell are modified to arm with the BsAb of the present disclosure on its surface by cultivating with the present BsAb in a culture medium. In addition or optionally, the culture medium may further comprise a cytokine selected from the group consisting of IL-2, IL-7, and a combination thereof.

Preferably, the T cells of the present disclosure are administered to the subject in the amount of $1 \times 10^4$ to $1 \times 10^7$ cells/Kg body weight of the subject. The amount can be administered in a single dose, or alternatively in more than one smaller doses.

Cancers, preferably those that are positive with the expression of EGFR, PSMA, or PD-L1 are treatable by the present method. Examples of the cancer treatable by the present method includes, but is not limited to, bladder cancer, biliary cancer, bone cancer, brain tumor, breast cancer, cervical cancer, colorectal cancer, colon cancer, esophageal cancer, epidermal carcinoma, gastric cancer, gastrointestinal stromal tumor (GIST), glioma, hematopoietic tumors of lymphoid lineage, hepatic cancer, non-Hodgkin's lymphoma, Kaposi's sarcoma, leukemia, lung cancer, lymphoma, intestinal cancer, melanoma, myeloid leukemia, pancreatic cancer, prostate cancer, retinoblastoma, ovary cancer, renal cell carcinoma, spleen cancer, squamous cell carcinoma, thyroid cancer, and thyroid follicular cancer.

According to one specific embodiment of the present disclosure, the cancer is triple-negative breast cancer. According to another specific embodiment of the present disclosure, the cancer is a malignant pancreatic cancer.

The details of one or more embodiments of the invention are set forth in the accompanying description below. Other features and advantages of the invention will be apparent from the detail descriptions, and from claims.

BRIEF DESCRIPTION OF THE DRAWINGS

These and other features, aspects and advantages of the present invention will become better understood with reference to the following description, appended claims and the accompanying drawings, where:

DESCRIPTION

Figure 1:
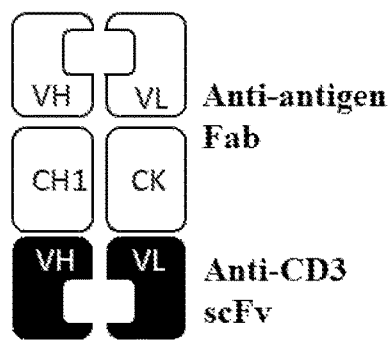
FIG. 1 are schematic diagrams of the structures of (A) anti-antigen Fab/anti-CD3 scFv, (B) anti-CD3 Fab/anti-antigen scFv, (C) anti-CD3 scFv/anti-antigen scFv, and (D) anti-antigen knob/anti-CD3 hole BsAbs of the present disclosure.
Figure 1:
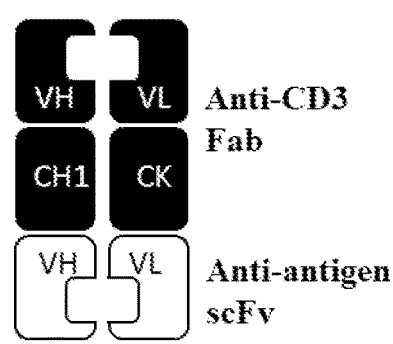
Figure 1:
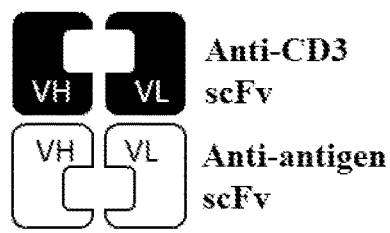
Figure 1:
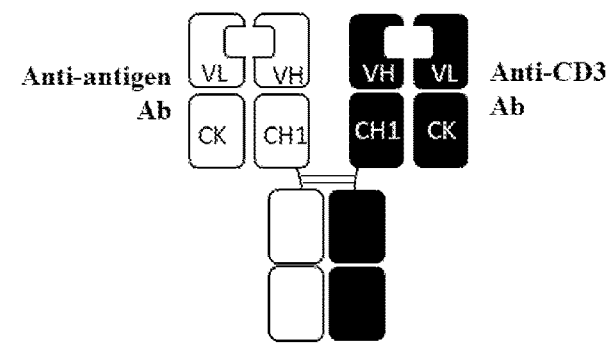

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

The term "antibody" is used in the broadest sense and specifically covers monoclonal antibodies, polyclonal antibodies, multi-specific antibodies (e.g., bi-specific antibodies), and antibody fragments so long as they exhibit the desired biological activity, that is, to specifically bind to an antigen when it preferentially recognizes its target antigen in a complex mixture of proteins and/or other molecules.

The term "monoclonal antibody" as used herein refers to an antibody obtained from a population of substantially homogeneous antibodies, and is not to be constructed as requiring production of the antibody by any particular method. In contrast to polyclonal antibodies which typically include different antibodies directed to different epitopes, each monoclonal antibody is directed against a single determinant (i.e., epitope) on the antigen. The monoclonal antibodies of the present disclosure may be made by hybridoma method or by recombinant DNA methods. The monoclonal antibodies herein specifically include "chimeric" or "recombinant" antibodies, in which a portion of the heavy and/or light chain is identical with or homologous to corresponding sequences in antibodies derived from a particular species or belonging to a antibody class or subclass, while the remainder of the chain identical with or homologous to corresponding sequences in antibodies derived from another species or belonging to another antibody class or subclass, as well as fragments of such antibodies, as long as they exhibit the desired biological activity.

"Humanized" forms of non-human (e.g., murine) antibodies are chimeric antibodies which contain minimal sequence derived from non-human immunoglobulin. Humanized antibodies are human immunoglobulins in which hypervariable region residues are replaced by hypervariable region residues from a non-human species such as mouse, rat, rabbit, or non-human primate having the desired specificity or affinity. In some instances, Fv framework region (FR) residues of the human immunoglobulin are replaced by corresponding non-human residues. In general, the humanized antibody will comprise substantially all of at least one, and typically two, variable domains, in which all or substantially all of the FR regions are those of a human immunoglobulin sequence. The humanized antibody may optionally comprise at least a portion of an immunoglobulin constant region (Fc), typically that of a human immunoglobulin.

The term "bi-specific antibody (BsAb)" refers to an antibody having specificities for at least two different antigens. In preferred embodiments, the BsAb of the present disclosure has two antigen-binding sites, in which one is directed against a tumor antigen (e.g., EGFR, PD-L1, HER2, PSMA and etc), while the other is directed against a T cell receptor (e.g., CD3).

The term "linker" and "peptide linker" are interchangeably used in the present disclosure and refers to a peptide having natural or synthetic amino acid residues for connecting two polypeptides. For example, the peptide linker may be used to connect the VH and the VL to form the single chain variable fragment (e.g., scFv); or to connect the scFv to the full length antibody to form a BsAb of the present disclosure. Preferably, the linker is a peptide having at least 5 amino acid residues in length, such as to 100 amino acid residues in length, more preferably 10 to 30 amino acid residues in length. The linker within scFv is a peptide of at least 5 amino acid residues in length, preferably 15 to 20 amino acid residues in length. Preferably, the linker comprises a sequence of $(G_nS)_m$, with G=glycine, S=serine, and n and m are independently a number between 1 to 4. In one example, the linker comprises a sequence of $(G_2S)_4$. In another example, the linker comprises a sequence or $(G_4S)_3$.

The terms "cancer" and "tumor" are used alternatively in the present disclosure and preferably refer to the physiological condition in mammals and especially in humans that is typically characterized by un-regulated cell growth. Cancers in this respect include metastases cancers, and/or drug-resistant cancers. Cancers, preferably those exhibit increased expression levels of αvβ3, a5β1, carcinoembryonic antigen (CEA), cytotoxic T-lymphocyte-associated antigen 4 (CTLA4), CD3, CD19, CD20, CD30, CD50, CIAX, cMuc1, ED-B, epidermal growth factor receptor (EGFR), epithelia cell adhesion molecules (EpCAM), erythropoietin-producing hepatocellular A3 EPHA3), familial adenomatous polyposis (FAP), gpA33, Globo-H, human epidermal growth factor receptor 2 (HER2), HER3, insulin like growth factor 1 receptor (IGF1R), OC183B2, platelet-derived growth factor receptor (PDGFR), programed cell death ligand 1 (PD-L1), prostate specific membrane antigen (PSMA), Leg, MET, tumor-associated glycoprotein 72 (TAG72), Tenascin, vascular endothelial growth factor receptor (VEGFR), VEGFR-2, and/or VEGFR-3. Accordingly, cancers or tumors treatable by the present disclosure are breast, lung, colon, colorectal, spleen, kidney, liver, bladder, head and neck, ovary, prostate, brain, pancreas, skin, bone, blood, thymus, uterus, testicles, cervix, and neuron. More specifically, the cancer is selected from the group consisting of bladder cancer, biliary cancer, bone cancer, brain tumor, breast cancer, cervical cancer, colorectal cancer, colon cancer, esophageal cancer, epidermal carcinoma, gastric cancer, gastrointestinal stromal tumor (GIST), glioma, hematopoietic tumors of lymphoid lineage, hepatic cancer, non-Hodgkin's lymphoma, Kaposi's sarcoma, leukemia, lung cancer, lymphoma, intestinal cancer, melanoma, myeloid leukemia, pancreatic cancer, prostate cancer, retinoblastoma, ovary cancer, renal cell carcinoma, spleen cancer, squamous cell carcinoma, thyroid cancer, or thyroid follicular cancer. In one example, the caner is a malignant pancreatic cancer. In another example, the cancer is triple-negative breast cancer (TNBC).

The term "an effective amount" as used herein refers to an amount effective, at dosages, and for periods of time necessary, to achieve the desired therapeutically desired result with respect to the treatment of cancers.

The term "administered," "administering" or "administration" are used interchangeably herein to refer means either directly administering a BsAb of the present disclosure, T cells differentiated and proliferated by the BsAb of the present disclosure, or a combination thereof.

The term "subject" or "patient" refers to an animal including the human species that is treatable with the compositions and/or methods of the present disclosure. The term "subject" or "patient" intended to refer to both the male and female gender unless one gender is specifically indicated. Accordingly, the term "subject" or "patient" comprises any mammal which may benefit from treatment of cancer. Examples of a "subject" or "patient" include, but are not limited to, a human, rat, mouse, guinea pig, monkey, pig, goat, cow, horse, dog, cat, bird and fowl. In an exemplary embodiment, the patient is a human.

The term "identical" or "percent identity" as used herein refers to two or more sequences or subsequences that are the same or have a specified percentage of amino acid residues that are the same, when compared and aligned for maximum correspondence. To determine the percent identity, the sequences are aligned for optimal comparison purposes (e.g., gaps can be introduced in the sequence of a first amino acid sequence for optimal alignment with a second amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=number of identical positions/total number of positions (e.g., overlapping positions)×100). In certain embodiments, the two sequences are the same length.

The singular forms "a," "and," and "the" are used herein to include plural referents unless the context clearly dictates otherwise.

II. Description of the Invention

Accordingly, it is the first aspect of the present disclosure to provide antigen-specific T cells, particularly T cells that are activated (or induced differentiation) by recombinant bi-specific antibodies (BsAbs) of the present disclosure that convert peripheral blood mononuclear cells (PBMCs) into T cells bearing specific anti-tumor antigen and anti-CD3 fragments on the surfaces. Accordingly, such antigen-specific T cells would bind more strongly to tumor cells including malignant tumor cells and triple-negative breast cancer (TNBC) cells, thereby may suppress the growth and metastasis of the tumor cells.

1. The BsAbs of the Present Disclosure

Antibodies belong to the immunoglobulin class of proteins that includes IgG, IgA, IgE, IgM, and IgD. The most abundant immunoglobulin found in serum is IgG, which has four chains, two light chains and two heavy chains; each light chain has two domains and each heavy chain has four domains. The antigen-binding site is located in the fragment antigen binding (Fab) region that contains a variable light (VL) and variable heavy (VH) chain domains as well as a constant light (CL) and constant heavy (CH1) domains. The CH2 and CH3 domain region of the heavy chain is called fragment crystallizable (Fc) region. A full length antibody heavy chain is therefore a polypeptide consisting of, from N-terminus to C-terminus, a VH, a CH1, a hinge region (HR), a CH2, and a CH3; abbreviated as VH-CH1-HR-CH2-CH3. A full length antibody light chain is a polypeptide consisting in N-terminus to C-terminus direction of a VL and a CL, abbreviated as VL-CL, in which the CL can be κ (kappa) or λ (lambda). The IgG is regarded as a heterotetramer having two heavy chains that are held together by disulfide bonds (—S—S—) between the CL domain and the CH1 domain and between the hinge regions of the two heavy chains.

As stated above in the "definition" section, the BsAbs refer to Abs having specificities for different antigens; hence, BsAbs of the present disclosure is a recombinant Ab engineered to contain sequences capable of binding to two different antigens, which are a tumor antigen and a CD3 antigen. Accordingly, each BsAbs of the present disclosure contains an anti-tumor antigen sequence and an anti-CD3 sequence. Various recombinant BsAbs have been developed in the present disclosure, and are used to induce differentiation and/or proliferation of mononuclear cells into antigen specific T cells that bear on their surfaces moieties that correspond to the antigens of BsAbs.

Reference is made to FIG. 1, which illustrates the schematic structures of BsAbs suitable for use in the present disclosure.

In some embodiments, the BsAb of the present disclosure is monomeric, divalent bi-specific antibody, in which a VH-CH1 domain and a light chain VL-Ck directed to a tumor antigen (i.e., anti-tumor antigen Fab) is fused to an anti-CD3 scFv (scFv) consisting of a heavy chain domain (VH) and a light chain variable domain (VL), abbreviated as VH-VL (FIG. 1A). In other embodiments, the monomeric, divalent BsAb comprises in its structure, an anti-CD3 Fab consisting of a VH-CH1 domain and a light chain VL-Ck directed to CD3, which is fused to an scFv directed to a tumor antigen (FIG. 1B) via a peptide linker. In further embodiments, the monomeric, divalent BsAb of the present disclosure is composed of, an anti-tumor antigen scFv and an anti-CD3 scFv, in which both scFvs are connected via a peptide linker (FIG. 1C). In still further embodiments, the BsAb of the present disclosure has a "knob into hole" structure, in which a knob in the CH3 domain of the first heavy chain is created by replacing several amino acid side chains with alternative ones, and a hole in the juxtaposed position at the CH3 domain of the second heavy chain is created by replacing appropriate amino acid side chains with alternative ones. A schematically presentation of the "knob into hole" BsAb structure is depicted in FIG. 1D. The knob-in-hole technique is well known to those skilled in the art, and can be readily applied in forming the BsAbs of the present disclosure.

DNAs encoding the present BsAbs are derived from known antibodies, their genes are cloned and fused to create DNA constructs of desired humanized BsAbs. Detailed production method is set forth in the Examples.

Accordingly, recombinant BsAb having binding sites to the CD3 of a T cell, and a tumor antigen selected from the group consisting of PSMA, EGFR, PD-L1, CEA, FAP, EpCAM, HER2, and VCAM-1, are created.

According to some embodiments, anti-PSMA/anti-CD3 BsAbs are produced. In one example, the anti-PSMA/anti-CD3 BsAb comprises a PSMA binding site comprising aVH-CH1 domain of SEQ ID NO: 65 and a VL-Ck domain of SEQ ID NO: 64; and a CD3 binding site comprising an anti-CD3 scFv of SEQ ID No: 66. In another example, the anti-PSMA/anti-CD3 BsAb comprises a PSMA binding site comprising an anti-PSMA scFv of SEQ ID NO: 69; and a CD3 binding site comprising aVH-CH1 domain of SEQ ID NO: 68 and a VL-Ck domain of SEQ ID NO: 67. In a further example, the anti-PSMA/anti-CD3 BsAb comprises a PSMA binding site comprising an anti-PSMA scFv of SEQ ID NO: 70; and a CD3 binding site comprising an anti-CD3 scFv of SEQ ID NO: 66. In still a further example, the anti-PSMA/anti-CD3 BsAb has a "knob into hole" structure, in which the CD3 binding site comprises a VL-Ck knob domain of SEQ ID NO: 71 and a VH-CH1 knob domain of SEQ ID NO: 72; and the PSMA binding site comprises a VL-Ck hole domain of SEQ ID NO: 73 and a VH1-CH1 hole domain of SEQ ID NO: 74.

According to some embodiments, anti-EGFR/anti-CD3 BsAbs are produced. In one example, the anti-EGFR/anti-CD3 BsAb comprises an EGFR binding site comprising aVH-CH1 domain of SEQ ID NO: 75 and a VL-Ck domain of SEQ ID NO: 76; and a CD3 binding site comprising an anti-CD3 scFv of SEQ ID No: 66. In another example, the anti-EGFR/anti-CD3 BsAb comprises an EGFR binding site comprising an anti-EGFR scFv of SEQ ID NO: 77; and a CD3 binding site comprising aVH-CH1 domain of SEQ ID NO: 68 and a VL-Ck domain of SEQ ID NO: 67. In a further example, the anti-EGFR/anti-CD3 BsAb comprises an EGFR binding site comprising an anti-EGFR scFv of SEQ ID NO: 78; and a CD3 binding site comprising an anti-CD3 scFv of SEQ ID NO: 79. In still a further example, the anti-EGFR/anti-CD3 BsAb has a "knob into hole" structure, in which the CD3 binding site comprises a VL-Ck knob domain of SEQ ID NO: 71 and a VH-CH1 knob domain of SEQ ID NO: 72; and the EGFR binding site comprises a VL-Ck hole domain of SEQ ID NO: 80 and a VH1-CH1 hole domain of SEQ ID NO: 81.

According to some embodiments, anti-PD-L1/anti-CD3 BsAbs are produced. In one example, the anti-PD-L1/anti-CD3 BsAb comprises a PD-L1 binding site comprising aVH-CH1 domain of SEQ ID NO: 83 and a VL-Ck domain of SEQ ID NO: 82; and a CD3 binding site comprising an anti-CD3 scFv of SEQ ID No: 66. In another example, the anti-PD-L1/anti-CD3 BsAb comprises a PD-L1 binding site comprising an anti-PD-L1 scFv of SEQ ID NO: 84; and a CD3 binding site comprising aVH-CH1 domain of SEQ ID NO: 68 and a VL-Ck domain of SEQ ID NO: 67. In a further example, the anti-PD-L1/anti-CD3 BsAb comprises a PD-L1 binding site comprising an anti-PD-L1 scFv of SEQ ID NO: 85; and a CD3 binding site comprising an anti-CD3 scFv of SEQ ID NO: 79. In still a further example, the anti-PD-L1/anti-CD3 BsAb has a "knob into hole" structure, in which the CD3 binding site comprises a VL-Ck knob domain of SEQ ID NO: 71 and a VH-CH1 knob domain of SEQ ID NO: 72; and the PD-L1 binding site comprises a VL-Ck hole domain of SEQ ID NO: 86 and a VH1-CH1 hole domain of SEQ ID NO: 87.

According to some embodiments, anti-HER2/anti-CD3 BsAbs are produced. In one example, the anti-HER2/anti-CD3 BsAb comprises a HER2 binding site comprising aVH-CH1 domain of SEQ ID NO: 89 and a VL-Ck domain of SEQ ID NO: 88; and a CD3 binding site comprising an anti-CD3 scFv of SEQ ID No: 66. In another example, the anti-HER2/anti-CD3 BsAb comprises a HER2 binding site comprising an anti-HER2 scFv of SEQ ID NO: 90; and a CD3 binding site comprising aVH-CH1 domain of SEQ ID NO: 68 and a VL-Ck domain of SEQ ID NO: 67. In a further example, the anti-HER2/anti-CD3 BsAb comprises a HER2 binding site comprising an anti-HER2 scFv of SEQ ID NO: 91; and a CD3 binding site comprising an anti-CD3 scFv of SEQ ID NO: 79. In still a further example, the anti-HER2/anti-CD3 BsAb has a "knob into hole" structure, in which the CD3 binding site comprises a VL-Ck knob domain of SEQ ID NO: 71 and a VH-CH1 knob domain of SEQ ID NO: 72; and the HER2 binding site comprises a VL-Ck hole domain of SEQ ID NO: 92 and a VH1-CH1 hole domain of SEQ ID NO: 93.

According to some embodiments, anti-FAP/anti-CD3 BsAbs are produced. In on example, the anti-FAP/anti-CD3 BsAb comprises an FAP binding site comprising aVH-CH1 domain of SEQ ID NO: 95 and a VL-Ck domain of SEQ ID NO: 94; and a CD3 binding site comprising an anti-CD3 scFv of SEQ ID No: 66. In another example, the anti-FAP/anti-CD3 BsAb comprises an FAP binding site comprising an anti-FAP scFv of SEQ ID NO: 96; and a CD3 binding site comprising aVH-CH1 domain of SEQ ID NO: 68 and a VL-Ck domain of SEQ ID NO: 67. In a further example, the anti-FAP/anti-CD3 BsAb comprises an FAP binding site comprising an anti-FAP scFv of SEQ ID NO: 97; and a CD3 binding site comprising an anti-CD3 scFv of SEQ ID NO: 79. In still a further example, the anti-FAP/anti-CD3 BsAb has a "knob into hole" structure, in which the CD3 binding site comprises a VL-Ck knob domain of SEQ ID NO: 71 and a VH-CH1 knob domain of SEQ ID NO: 72; and the FAP binding site comprises a VL-Ck hole domain of SEQ ID NO: 98 and a VH1-CH1 hole domain of SEQ ID NO: 99.

According to some embodiments, anti-EpCAM MOC31/anti-CD3 BsAbs are produced. In one example, the anti-EpCAM MOC31/anti-CD3 BsAb comprises an EpCAM MOC31 binding site comprising a VH-CH1 domain of SEQ ID NO: 101 and a VL-Ck domain of SEQ ID NO: 100; and a CD3 binding site comprising an anti-CD3 scFv of SEQ ID No: 66. In another example, the anti-EpCAM MOC31/anti-CD3 BsAb comprises an EpCAM MOC31 binding site comprising an anti-EpCAM MOC31 scFv of SEQ ID NO: 102; and a CD3 binding site comprising aVH-CH1 domain of SEQ ID NO: 68 and a VL-Ck domain of SEQ ID NO: 67. In a further example, the anti-EpCAM MOC31/anti-CD3 BsAb comprises an EpCAM MOC31 binding site comprising an anti-EpCAM MOC31 scFv of SEQ ID NO: 103; and a CD3 binding site comprising an anti-CD3 scFv of SEQ ID NO: 79. In still a further example, the anti-EpCAM MOC31/anti-CD3 BsAb has a "knob into hole" structure, in which the CD3 binding site comprises a VL-Ck knob domain of SEQ ID NO: 71 and a VH-CH1 knob domain of SEQ ID NO: 72; and the EpCAM MOC31 binding site comprises a VL-Ck hole domain of SEQ ID NO: 104 and a VH1-CH1 hole domain of SEQ ID NO: 105.

According to some embodiments, anti-EpCAM MT201/anti-CD3 BsAbs are produced. In one example, the anti-EpCAM MT201/anti-CD3 BsAb comprises an EpCAM MT201 binding site comprising a VH-CH1 domain of SEQ ID NO: 107 and a VL-Ck domain of SEQ ID NO: 106; and a CD3 binding site comprising an anti-CD3 scFv of SEQ ID No: 66. In another example, the anti-EpCAM MT201/anti-CD3 BsAb comprises an EpCAM MT201 binding site comprising an anti-EpCAM MT201 scFv of SEQ ID NO: 108; and a CD3 binding site comprising aVH-CH1 domain of SEQ ID NO: 68 and a VL-Ck domain of SEQ ID NO: 67. In a further example, the anti-EpCAM MT201/anti-CD3 BsAb comprises an EpCAM MT201 binding site comprising an anti-EpCAM MT201 scFv of SEQ ID NO: 109; and a CD3 binding site comprising an anti-CD3 scFv of SEQ ID NO: 79. In still a further example, the anti-EpCAM MT201/anti-CD3 BsAb has a "knob into hole" structure, in which the CD3 binding site comprises a VL-Ck knob domain of SEQ ID NO: 71 and a VH-CH1 knob domain of SEQ ID NO: 72; and the EpCAM MT201 binding site comprises a VL-Ck hole domain of SEQ ID NO: 110 and a VH1-CH1 hole domain of SEQ ID NO: 111.

According to some embodiments, anti-CEA/anti-CD3 BsAbs are produced. In one example, the anti-CEA/anti-CD3 BsAb comprises a CEA binding site comprising a VH-CH1 domain of SEQ ID NO: 113 and a VL-Ck domain of SEQ ID NO: 112; and a CD3 binding site comprising an anti-CD3 scFv of SEQ ID No: 66. In another example, the anti-CEA/anti-CD3 BsAb comprises a CEA binding site comprising an anti-CEA scFv of SEQ ID NO: 114; and a CD3 binding site comprising aVH-CH1 domain of SEQ ID NO: 68 and a VL-Ck domain of SEQ ID NO: 67. In a further example, the anti-CEA/anti-CD3 BsAb comprises a CEA binding site comprising an anti-CEA scFv of SEQ ID NO: 115; and a CD3 binding site comprising an anti-CD3 scFv of SEQ ID NO: 79. In still a further example, the anti-CEA/anti-CD3 BsAb has a "knob into hole" structure, in which the CD3 binding site comprises a VL-Ck knob domain of SEQ ID NO: 71 and a VH-CH1 knob domain of SEQ ID NO: 72; and the CEA binding site comprises a VL-Ck hole domain of SEQ ID NO: 116 and a VH1-CH1 hole domain of SEQ ID NO: 117.

According to some embodiments, anti-VCAM1/anti-CD3 BsAbs are produced. In one example, the anti-VCAM1/anti-CD3 BsAb comprises a VCAM1 binding site comprising a VH-CH1 domain of SEQ ID NO: 119 and a VL-Ck domain of SEQ ID NO: 118; and a CD3 binding site comprising an anti-CD3 scFv of SEQ ID No: 66. In another example, the anti-VCAM1/anti-CD3 BsAb comprises a VCAM1 binding site comprising an anti-VCAM1 scFv of SEQ ID NO: 120; and a CD3 binding site comprising aVH-CH1 domain of SEQ ID NO: 68 and a VL-Ck domain of SEQ ID NO: 67. In a further example, the anti-VCAM1/anti-CD3 BsAb comprises a VCAM1 binding site comprising an anti-VCAM1 scFv of SEQ ID NO: 121; and a CD3 binding site comprising an anti-CD3 scFv of SEQ ID NO: 79. In still a further example, the anti-VCAM1/anti-CD3 BsAb has a "knob into hole" structure, in which the CD3 binding site comprises a VL-Ck knob domain of SEQ ID NO: 71 and a VH-CH1 knob domain of SEQ ID NO: 72; and the VCAM1 binding site comprises a VL-Ck hole domain of SEQ ID NO: 122 and a VH1-CH1 hole domain of SEQ ID NO: 123.

According to further embodiments of the present disclosure, humanized OKT3 Anti-CD3 VH and CL are produced, these sequences (see Tables 39 to 42) may fused with relevant anti-tumor antigen sequences described in the present disclosure to produce desired BsAbs.

2. Antigen Specific T Cells Activated by the Present BsAbs

The BsAbs of the present disclosure are used to induce differentiation and proliferation of mononuclear cells (e.g., peripheral mononuclear cells) into antigen specific T cells of the present disclosure. Accordingly, one aspect of the present disclosure is directed to the production of antigen specific T cells, which respectively comprise an anti-tumor antigen moiety and an anti-CD3 moiety on the surfaces.

Accordingly, the present disclosure encompasses a method of inducing differentiation and/or proliferation of T cells. The method comprises, culturing peripheral blood mononuclear cells (PBMCs) harvested from a subject with bi-specific antibodies (BsAbs) of the present disclosure in a medium, so as to differentiate the PBMCs into the T cells and proliferate the thus differentiated T cells, wherein, each BsAbs comprises a tumor antigen binding site that corresponds to the anti-tumor antigen moiety on each T cells, and a CD3 binding site that corresponds to the anti-CD3 moiety on each T cells, and the BsAbs are not murine OKT3 antibodies.

PBMCs may be isolated from fresh blood of a subject using any methods known to a skilled artisan, such as by density centrifugation (Ficoll-Paque™), as different components of the blood have different densities and can be separated accordingly.

To achieve differentiation and proliferation of T cells, the isolated PBMCs are cultivated with any of BsAbs of the present disclosure in a normal culture medium for a sufficient period of time, for example, at least 7 days, such as 7, 8, 9, 10, 11, 12, 13, and 14 days; and preferably for at least 14 days. In some embodiments, the number of CD3+ T cells multiplies after cultivation for 7 days. In other embodiments, cultivation is continued for 14 days, and the number of CD3+ T cells increases for 3 folds. In addition or optionally, the culture medium may include a cytokine, such as IL-2, IL-7 and a combination thereof.

According to embodiments of the present disclosure, T cells thus produced respectively comprise on their surfaces, an anti-tumor antigen moiety that corresponds to the anti-tumor antigen of the BsAb, and an anti-CD3 moiety that corresponds to the anti-CD3 of the BsAb. In some examples, T cells thus produced respectively comprise anti-PSMA and anti-CD3 moieties on the surfaces. In other examples, T cells thus produced respectively comprise anti-EGFR and anti-CD3 moieties on the surfaces. In further examples, T cells thus produced respectively comprise anti-PD-L1 and anti-CD3 moieties on the surfaces.

According to further embodiments of the present disclosure, periphery derived regulatory T cells are produced after cultivating PBMCs with the BsAbs of the present disclosure for at least 7 days, in which cell marker FoxP3 appeared on the surface of the T cells. In such case, the culture medium further comprises anti-CD 28 antibodies, in addition to the cytokine, IL-2.

According to embodiments of the present disclosure, antigen specific T cells (including the periphery derived regulatory T cells) of the present disclosure not only exhibit stronger binding affinity toward tumor cells, but also produce higher levels of cytokines, including, but are not limited to, IL-2, IFN-γ, TNF-α, granzyme B and perforin. Accordingly, these T cells exhibit much higher level of cytotoxicity toward tumor cells, including malignant cancer cells and TNBC cells, as compared with T cells activated by murine OKT3 Abs.

3. Methods of Treating Cancers 3.1 Treating Cancer by Use of Antigen Specific T Cells Accordingly, it is a further aspect of the present disclosure to provide a method of treating cancers. The method takes advantages of antigen specific T cells described in Section 2, in which an effective amount of the T cells per se, or T cells that are further modified with BsAbs, is administered to a subject afflicted with a cancer, so as to suppress or inhibit the growth of the cancer cells.

Figure 2A:
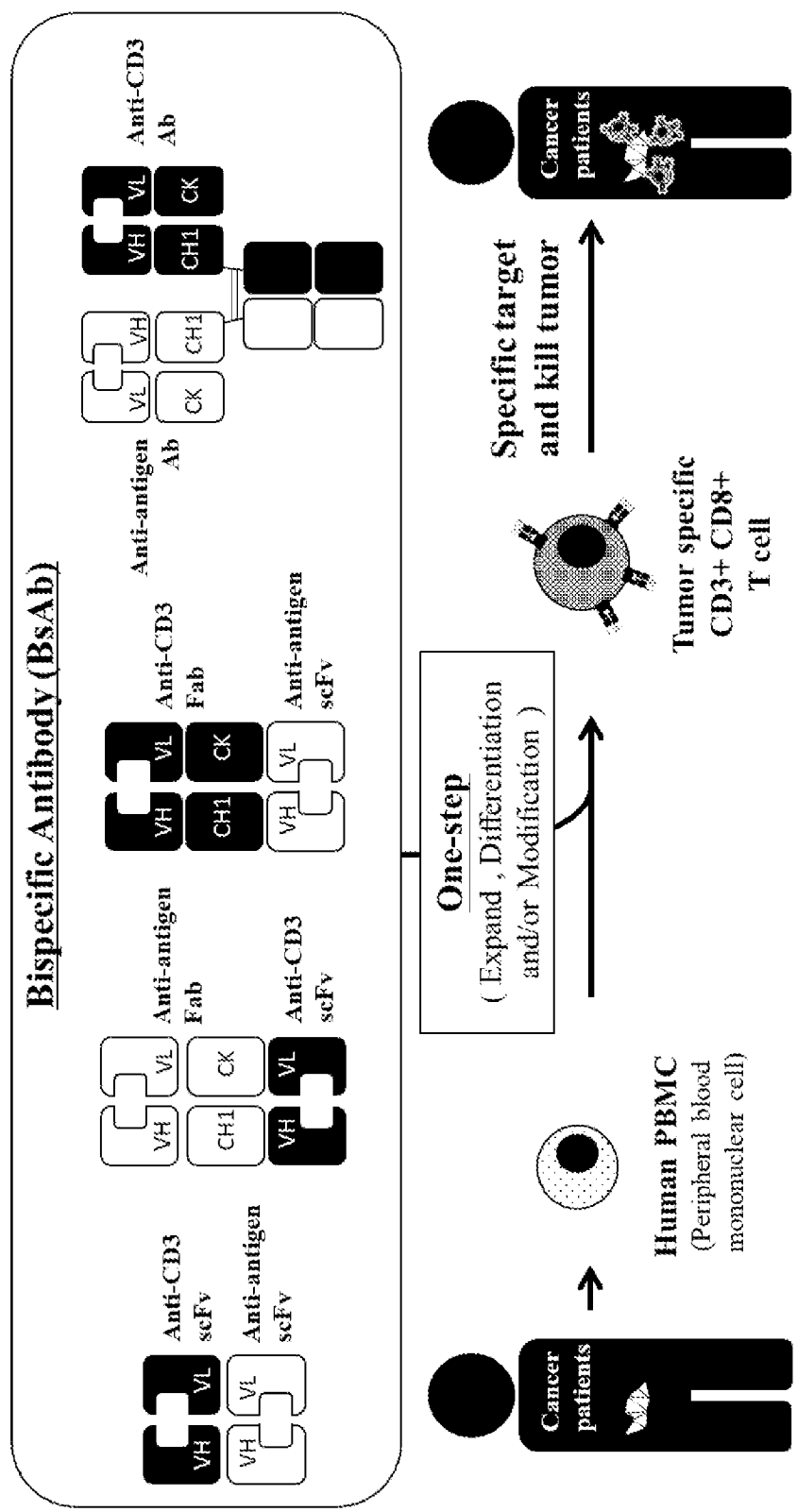
FIG. 2A is a schematic presentation of treating a subject with antigen specific T cells produced by one-step expanding, differentiation and/or modification with BsAbs of the present disclosure.

Reference is made to FIG. 2A, which is a schematic presentation of the present method, in which PBMCs are first isolated from fresh blood of a subject, then subjected to one-step expanding and differentiation treatment to arm the differentiated T cells with moieties respectively correspond to the anti-tumor antigen and the anti-CD3 of the BsAbs. Specifically, the one-step expanding and differentiation treatment incudes cultivating PBMCs with the BsAbs of the present disclosure in a culture medium for at least 7 days, more preferably, for at least 14 days, until sufficient number of desired T cells are produced. In addition or optionally, the antigen specific T cells thus produced may be further modified with the BsAbs, in which case, the present antigen specific T cells are further incubated with the BsAbs of the present disclosure, such step is termed "one-step expanding, differentiation and modification" treatment depicted in FIG. 2A.

In some embodiments, an effective amount of the antigen specific T cells (i.e., without further modification with the BsAbs) are administered directly to the subject for treating cancer. In other embodiments, an effective amount of the antigen specific T cells further modified with the BsAbs are administered to the subject for treating cancer. The amount of T cells administered to the subject is from about $1\times10^4$ to $1\times10^7$ cells/Kg body weight of the subject. In certain embodiments, the amount of T cells is administered to the subject from about $1\times10^5$ to $1\times10^6$ cells/Kg body weight of the subject. The dose can be administered in a single dose, or alternatively in more than one smaller doses.

Figure 2B:
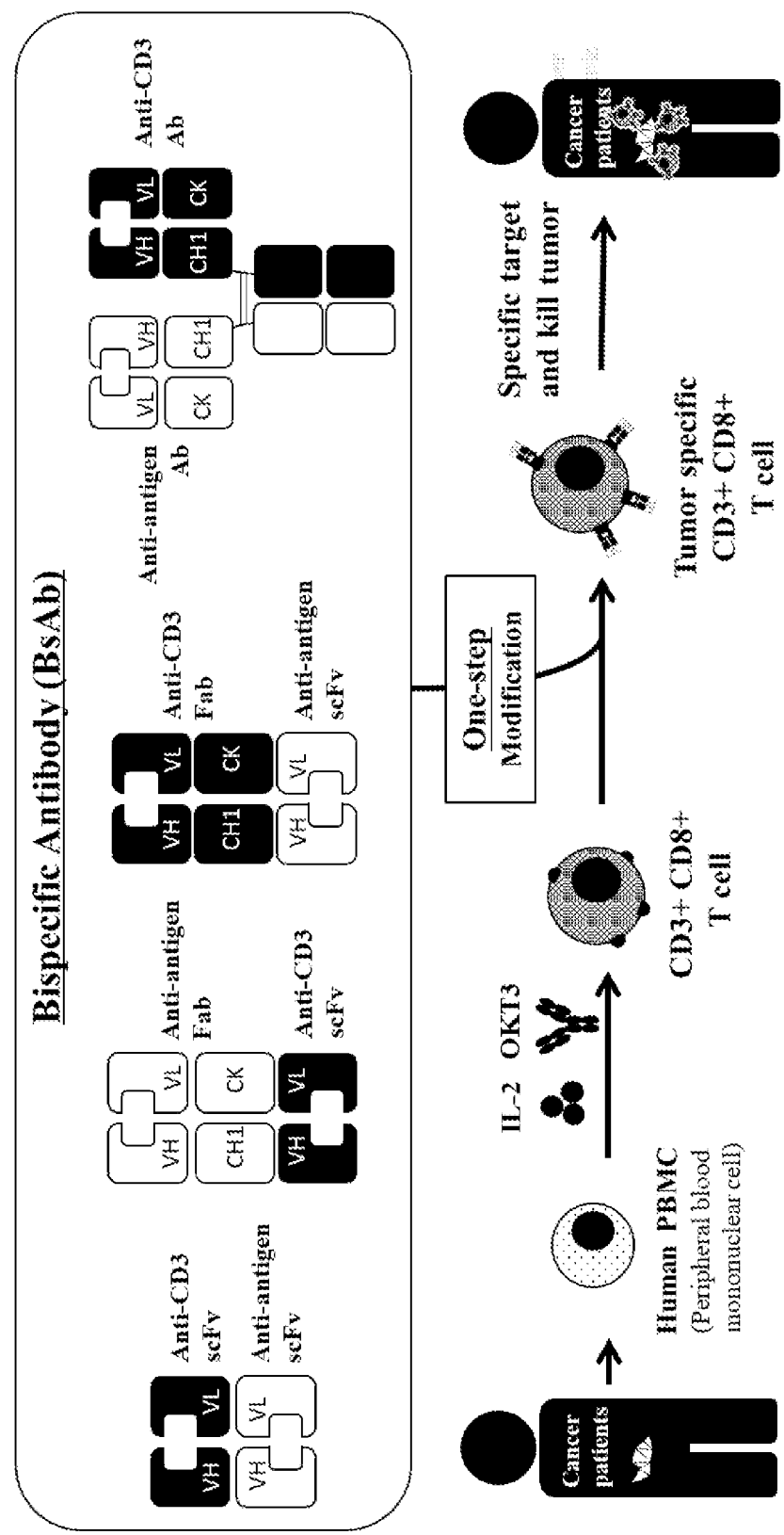
FIG. 2B is a schematic presentation of treating a subject with murine OKT3 T cells produced by one-step modification with BsAbs of the present disclosure.

3.2 Treating Cancer by Use of Murine OKT3 T Cells Modified with the Present BsAbs In some embodiments, instead of using the antigen specific T cells described above in Section 2, murine OKT3 T cells (i.e., T cells derived by activating PBMCs via murine OKT3 Abs) further modified with the BsAbs of the present disclosure are used for the treatment of a cancer. Reference is made to FIG. 2B, which is similar to FIG. 2A, except murine OKT3 T cells are modified with the BsAbs of the present disclosure and administered to the subject. Similar to FIG. 2A, the modification is achieved by cultivating murine OKT3 T cells with the BsAbs of the present disclosure, so as to arm murine OKT3 T cells with the anti-tumor antigen and the anti-CD3 of the BsAbs.

According to embodiments of the present disclosure, at least 500 ng, such as 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, and 3,000 ng of BsAbs of the present disclosure is sufficient to modify murine OKT3 T cells (e.g., $3\times10^5$ cells) so that the desired anti-tumor antigen of the BsAbs of the present disclosure are expressed on their surfaces. In some examples, murine OKT3 T cells are further modified with anti-PSMA/anti-CD3 BsAbs of the present disclosure. In further examples, murine OKT3 T cells modified with anti-PSMA/anti-CD3 BsAbs of the present disclosure produce much higher level of cytokines, including, but are not limited to, IL-2, IFN-γ, TNF-α, Granzyme B and Perforin, as compared to unmodified murine OKT3 T cells. Accordingly, these modified murine OKT3 T cells exhibit much higher level of cytotoxicity toward tumor cells, including malignant cancer cells and TNBC cells, as compared with unmodified murine OKT3 T cells.

The BsAbs, antigen specific T cells, as well as the modified murine OKT3 T cells of the present disclosure may be administered to a mammal, preferably human, by any route that may effectively transport the BsAbs or T cells to desired site of action, such as oral, nasal, pulmonary, transdermal, such as passive or iontophoretic delivery, or parenteral, e.g., rectal, depot, subcutaneous, intravenous, intramuscular, intranasal, intra-cerebella, ophthalmic solution or an ointment. It will be appreciated that the dosage of the present disclosure will vary from patient to patient not only for the cancer therapeutic agent selected, the route of administration, and the ability of the BsAb, the T cells, and/or a combination thereof, to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the cancer therapeutic agent are outweighed by the therapeutically beneficial effects. Preferably, the BsAb, T cells, or a combination thereof, are administered at a dosage and for a time such that the growth of the cancer cells are suppressed.

The present invention will now be described more specifically with reference to the following embodiments, which are provided for the purpose of demonstration rather than limitation.

Examples

Materials and Methods.

Cells and Animals

Human T lymphocyte cell line Jurkat T cells (CD3$^+$), human prostate adenocarcinoma cell line LNCaP (PSMA$^+$/VPD-L1$^+$), human colon adenocarcinoma cell line HT-29 (EGFR$^+$), malignant pancreatic cell line MIA PaCa-2 (PD-L1$^+$), triple negative breast cancer (TNBC) cell line MDA-M13-231 (EGFR$^+$/PD-L1$^+$) and Expi293™ cells were used in the present disclosure.

In general, HT-29, MIA PaCa-2 and MDA-MB-231 cells were cultured in Dulbecco's modified Eagle's medium (Sigma, St Louis, MO, USA) supplemented with 10% fetal calf serum (HyClone, Logan, UT), 100 U/mL penicillin and 100 μg/mL streptomycin at 37° C. in an atmosphere of 5% CO$_2$ in air. Jurkat T and LNCaP cells were grown in RPMI-1640 containing the same supplements. Expi293™ cells were maintained in Expi293™ Expression medium at 37° C. in an atmosphere of 5% CO$_2$ in air.

SCID mice (6-8 weeks old) were obtained from the National Laboratory Animal Center, Taipei, Taiwan. All animal experiments were performed in accordance with institutional guidelines and approved by the Laboratory Animal Facility and Pathology Core Committee of Taipei Medical University (Taipei, Taiwan).

Production of Recombinant BsAbs

To generate the BsAbs of the present disclosure, nucleic acids encoding the anti-tumor antigen (e.g., anti-PSMA, anti-EGFR, anti-PD-L1 and etc) and anti-CD3 were grafted and fused with other DNA sequence (e.g., signal peptide, IRES, linker and etc) into desired constructs via whole gene synthesis.

The thus produced DNA constructs were then amplified in Expi293' cells (7.5×10$^7$ cell/25.5 mL, with the addition of 30 μg nucleic acids for transfection), which were cultured at 37° C. in an atmosphere of 8% CO$_2$ in air. BsAbs were purified from the culture media collected after 6 days by Ni-Affinity chromatography, and the concentration was determined by use of Pierce™ BCA Protein Assay kit.

Production of Humanized OKT3 VH and VL

To select human framework sequences for complementarity-determining region (CDR) grafting, we compared the VH and VL sequences of the OKT3 with the National Center for Biotechnology Information database of human immunoglobulin germline sequences in the variable and joining regions using the IgBLAST program. The IGHV1-46ˆ03/IGHJ4 was found to be the most homologous to the variable/joining regions of OKT3 VH. The IGKV1-39ˆ01/IgKJ4 was found to be the most homologous to the variable and joining regions of OKT3 VL. For construction of the humanized OKT3 VH, the CDRs determined by the rule of Kabat et al. (Sequences of Proteins of Immunological Interest. 5th ed. Bethesda, MD: U.S. Department of Health and Human Services, Public Health Service, National Institutes of Health; 1991:103-511) and 2 residues (Thr 71 and Lys 73) of OKT3 VH were similarly grafted into IGHV1-46ˆ03/IGHJ4. For construction of the humanized OKT3 VL, the CDRs determined by the rule of Kabat et al. and 1 residue (Tyr 71) of OKT3 VL were similarly grafted into IGKV1-39ˆ01/IgKJ4. The humanized OKT3 VH and VL segments were constructed via whole gene synthesis.

Analysis of the Purified BsAbs

BsAbs were electrophoresed in a 10% SDS-PAGE gels under reducing or non-reducing conditions and then stained by Coomassie® Blue.

Differentiation of T Cells

CD8$^+$ T cells. Peripheral blood mononuclear cells (PBMCs) isolated from the blood of healthy subjects or naïve CD8 T cells were washed with phosphate buffer solution (PBS) and re-suspended in AIM-V medium at the concentration of 2×10$^6$ cells/mL. The suspended cells were then cultivated with BsAbs (1-1,000 ng/mL) and humanized IL-2 (3,000 IU/mL) at 37° C. in an atmosphere of 5% CO$_2$ in air for designated time. Some of the T cells were collected respectively at 7 and 14 days, and analyzed by flow cytometry.

CD4$^+$ T cells. Differentiation of CD4$^+$ T cells was relatively the same as that for CD8$^+$ T cells, except PBMCs were re-suspended in AIM-V medium at the concentration of 1×10$^6$ cells/mL, and cultivated in the presence of BsAbs (1-1,000 ng/mL) and humanized IL-2 (2,000 IU/mL) and IL-7 (20 IU/mL).

Regulatory T cells. Differentiation of regulatory T cells was relatively the same as that for CD8 T cells, except PBMCs or naïve CD4 T cells were suspended in AIM-V medium at the concentration of 1×10$^6$ cells/mL, and cultivated in the presence of BsAbs (1-1,000 ng/mL), anti-CD28 antibody (100 ng/mL), humanized IL-2 (2,000 IU/mL) and D-mannose (25 mM).

Flow Cytometer Analysis

Tumor-specific antigen recognition and/or targeting. BsAbs (1 μg/mL) were incubated with LNCaP (PSMA+/PD-L1+), HT-29 (EGFR+), MDA-MB-231 (EGFR+/PD-L1+), MIA PaCa-2 (PD-L1+), or Jurkat (CD3+) cells (3×10$^5$ cells) at 4° C. for 60 min followed by incubation with mouse anti-histidine antibody (1 μg/mL) and FITC-labeled Goat F(ab)2 anti-mouse immunoglobulin second antibody (1 μg/mL) at 4° C. The fluorescence was measured by FACScalibur™ flow cytometer (Becton Dickinson, Mountain View, CA, USA) then analyzed with Flowjo® (Tree Star Inc., San Carlos, CA, USA).

T cells differentiation. Differentiated T cells (3×10$^5$ cells) were mixed with FITC-labeled conjugated anti-human CD3 antibody (1 μg/mL), FITC-labeled conjugated anti-human CD4 antibody (1 μg/mL), FITC-labeled conjugated anti-human CD8 antibody (1 μg/mL), or PE-conjugated anti-human FoxP3 antibody at 4° C. After washing with cold PBS, the fluorescence on the viable cells was measured by FACScalibur™ flow cytometer (Becton Dickinson, Mountain View, CA, USA) then analyzed with Flowjo® (Tree Star Inc., San Carlos, CA, USA).

Amount of BsAbs remained on the surface of T cells. T cells or T cells armed with BsAbs of Example 1 (3×10⁵ cells) were cultivated in a medium containing 20% FCS, and were harvested at 0, 24, 48, and 72 hrs, respectively. After washed with PBS, the harvested T cells were mixed with mouse anti-histidine antibody (1 µg/mL), and FITC-labeled Goat F(ab)2 anti-mouse immunoglobulin second antibody (1 µg/mL) at 4° C. The fluorescence was then measured by FACScalibur™ flow cytometer (Becton Dickinson, Mountain View, CA, USA) then analyzed with Flowjo® (Tree Star Inc., San Carlos, CA, USA).

Cytotoxicity Assay

Tumor cells (10⁴ cells/well) were seeded in 96-well plates and cultivated at 37° C. in an atmosphere of 5% $CO_2$ in air for 24 hrs. Then, the differentiated T cells (e.g., T cells of Example 2) or OKT3 T cells were added to the tumor cells at E/T ratio of 3:1, 5:1 or 10:1, and continued to cultivate for 16 hrs. The cells were subsequently harvested and the supernatant was analyzed by CytoTox96® Non-Radioactive Cytotoxicity Kit for evaluating the cytotoxicity effect of each differentiated T cells.

ELISA

The level of IL-2, INF-γ, TNF-α, Granzyme B and Perforin secreted from the differentiated T cells were respectively measured by commercial available ELISA kits in accordance with the manufacturer's instruction. Briefly, supernatant of the tumor cells treated with T cells of Example 2 or OKT3 T cells was collected and seeded in 96-well (100 µL/well) and incubated at 36° C. in an incubator for 1.5 hr. After washing with washing buffer, antibodies (100 µL/well) were added, and the mixtures were returned to the incubator and continued incubation at 36° C. for 1 hr. After washing, horse radish peroxidase (HRP) (100 µL/well) was added and continue the incubation for another 30 min. After washing, tetramethylbenzidine (TMB) (100 µL/well) was added, and the mixture was incubated in the dark at 36° C. for 15 min. Then, stop solution (100 µL/well) was added, and the absorbance (405 nm) of wells was measured in a microplate reader.

In Vivo Imaging of SCID Mice Bearing EGFR⁺ Tumors

SCID mice were respectively injected on their back with HT-29 (EGFR+) cells (2×10⁶ cells/100 µL) to induce formation of tumor. The tumor was allowed to grow for 14-17 days until it was about 80-100 mm³ in size, then NIR797-labeled OKT3 T cells further modified with anti-EGFR/anti-CD3 BsAb (10⁷ cells) were injected intravenously into the animals. Pentobarbital anesthetized mice were sequentially imaged with an IVIS spectrum optical imaging system (excitation, 745 nm; emission, 840 nm; Perkin-Elmer, Inc., MA, USA) at 4 and 24 hrs, respectively, after injection. Mice were then sacrificed, and the tumors and organs (including heart, lung, kidney, liver, stomach, muscle, bone, bowl, intestine, pancreas, and blood) were collected and also analyzed by IVIS spectrum optical imaging system.

Treatment of SCID Mice Bearing EGFR⁺ Tumors

SCID mice were respectively injected on their back with HT-29 (EGFR+) cells (2×10⁶ cells/100 µL) to induce formation of tumor. The tumor was allowed to grow for 10-14 days until it was about 30-50 mm³ in size, then NIR797-labeled T cells further modified with anti-EGFR/anti-CD3 BsAb (10⁷ cells/mice) were injected intravenously into the animals. Each mice were weighted and the size of the tumor measured (length×width×height×½) twice a week during the treatment period. Mice were then sacrificed, and the tumors were dissected and analyzed by H&E staining, or by immunostaining with anti-CD3 Abs.

Statistic Analysis.

Statistical significance of differences between mean values was estimated with JMP 9.0 software (SAS Institute, Inc., Cary, NC) using the nonparametric Mann-Whitney test. P-values in the cytotoxicity assay and in vivo toxicity $<0.05$ and the P-values in the in vivo treatment $<0.01$ were considered to be statistically significant.

Figure 3:
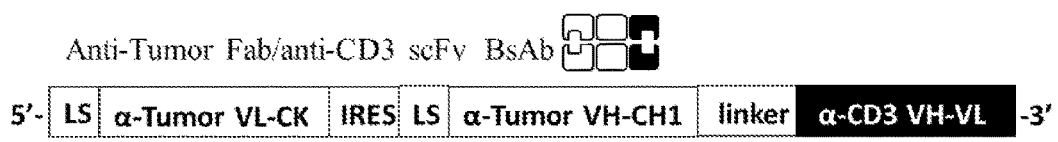
FIG. 3 is a schematic diagram of DNA constructs for the expression of BsAbs of the present disclosure.
Figure 3:
Figure 3:
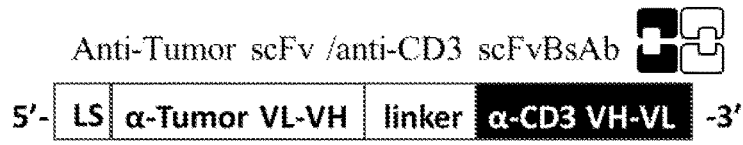
Figure 3:
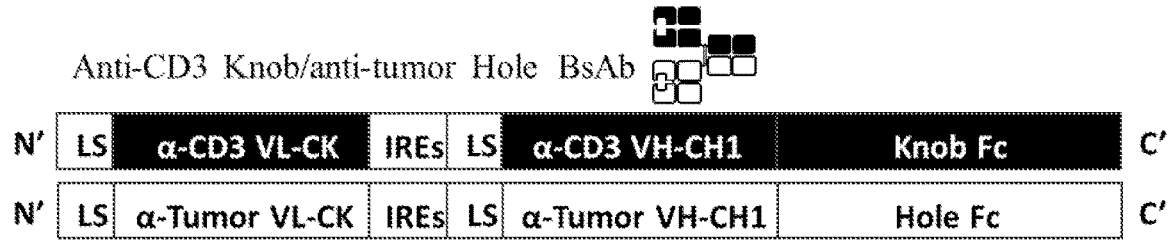

Example 1 Production and Characterization of Humanized Anti-Tumor/Anti-CD3 Antibodies 1.1 Production of Anti-Tumor/Anti-CD3 BsAbs In this example, recombinant humanized bi-specific Abs respectively having the structures as depicted in FIG. 1 were prepared vis use of the DNA constructs illustrated in FIG. 3. For anti-tumor Fab/anti-CD3 scFv BsAb, the construct comprised in sequence, IgG signal peptide (LS), anti-tumor VL-CK (e.g., anti-EGFR VL-CK), internal ribosomal entry site (IRES), anti-tumor VH-CH1 (e.g., anti-EGFR VH-CH1), linker peptide (L), and anti-CD3 VH-VL (FIG. 3, (A)). For anti-CD3 Fab/anti-tumor scFv BsAb, the construct comprised in sequence, LS, anti-CD3 VL-CK, IRES, LS, anti-CD3 VH-CH1, L, and anti-tumor VH-VL (FIG. 3, (B)). For anti-tumor scFv/anti-CD3 scFv BsAb, the construct comprised in sequence, LS, anti-tumor VL-VH, L, and anti-CD3 VH-VL (FIG. 3, (C)). For anti-CD3 knob/anti-tumor hole BsAb, the anti-CD3 knob construct comprised in sequence, LS, anti-CD3 VL-CK, IRES, LS, and anti-CD3 VH-CH1-knob Fc, while the anti-tumor hole comprised in sequence, LS, anti-tumor VL-CK, IRES, LS, and anti-tumor VH-CH1-hole Fc (FIG. 3, (D)).

Accordingly, BsAbs comprised an anti-CD3 and an anti-tumor antigen (i.e., anti-PSMA, anti-EGFR, anti-PD-L1, anti-HER2, and anti-FAP, anti-EpCAM (MOC31), anti-EpCAM (MO201), anti-CEA, and anti-VCAM-1) were prepared. Components and respective nucleic acid and amino acid sequences of the present BsAbs are summarized in Tables 1 to 36. The BsAbs were produced via Expi-293' expression system, and the yield of each BsAbs was above 100 mg/L, with an assembling accuracy over 95%.

TABLE 1

Components and sequences of anti-PSMA Fab/anti-CD3 scFv BsAb

| Name | Nucleic Acid Sequence (SEQ ID NO) | Amino Acid Sequence (SEQ ID NO) |
| --- | --- | --- |
| Signal Peptide | 1 | 63 |
| Anti-PSMA VL-Cκ | 2 | 64 |
| IRES | 3 | — |
| Anti-PSMA VH-CH1 | 4 | 65 |
| Anti-CD3 scFv | 5 | 66 |

TABLE 2

Components and sequences of anti-CD3 Fab/anti-PSMA scFv BsAb

| Name | Nucleic Acid Sequence (SEQ ID NO) | Amino Acid Sequence (SEQ ID NO) |
| --- | --- | --- |
| Signal Peptide | 1 | 63 |
| Anti-CD3 VL-Cκ | 6 | 67 |
| IRES | 3 | — |
| Anti-CD3 VH-CH1 | 7 | 68 |
| Anti-PSMA scFv | 8 | 69 |

TABLE 3

Components and sequences of anti-PSMA scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-PSMAscFv | 9 | 70 |
| Anti-CD3 scFv | 5 | 66 |

TABLE 4

Components and sequences of anti-CD3knob/anti-PSMA hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Ck | 10 | 71 |
| IRES | 3 | — |
| Anti-CD3 VH knob CH1-Fc | 11 | 72 |
| Anti-PSMA hole-Ck | 12 | 73 |
| Anti-PSMA VH hole CH1-Fc | 13 | 74 |

TABLE 5

Components and sequences of anti-EGFR Fab/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-EGFR VL-Cκ | 14 | 75 |
| IRES | 3 | — |
| Anti-EGFR VH-CH1 | 15 | 76 |
| Anti-CD3 scFv | 5 | 66 |

TABLE 6

Components and sequences of anti-CD3 Fab/anti-EGFR scFv BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL-Cκ | 6 | 67 |
| IRES | 3 | — |
| Anti-CD3 VH-CH1 | 7 | 68 |
| Anti-EGFR scFv | 16 | 77 |

TABLE 7

Components and sequences of anti-EGFR scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-EGFR scFv | 17 | 78 |
| Anti-CD3 scFv | 18 | 79 |

TABLE 8

Components and sequences of anti-CD3knob/anti-EGFR hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Ck | 10 | 71 |
| IRES | 3 | — |
| Anti-CD3 VH knob CH1-Fc | 11 | 72 |
| Anti-EGFR hole-Ck | 19 | 80 |
| Anti-EGFR VH hole CH1-Fc | 20 | 81 |

TABLE 9

Components and sequences of anti-PD-L1 Fab/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-PD-L1 VL-Cκ | 21 | 82 |
| IRES | 3 | — |
| Anti-PD-L1 VH-CH1 | 22 | 83 |
| Anti-CD3 scFv | 5 | 66 |

TABLE 10

Components and sequences of anti-CD3 Fab/anti-PD-L1 scFv BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL-Cκ | 6 | 67 |
| IRES | 3 | — |
| Anti-CD3 VH-CH1 | 7 | 68 |
| Anti-PD-L1 scFv | 23 | 84 |

TABLE 11

Components and sequences of anti-PD-L1 scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-PD-L1 scFv | 24 | 85 |
| Anti-CD3 scFv | 18 | 79 |

TABLE 12

Components and sequences of anti-CD3 knob/anti-PD-L1 hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Ck | 10 | 71 |
| IRES | 3 | — |
| Anti-CD3 VH knob CH1-Fc | 11 | 72 |

TABLE 12-continued

Components and sequences of anti-CD3 knob/anti-PD-L1 hole BsAb

| Name | Nucleic Acid Sequence (SEQ ID NO) | Amino Acid Sequence (SEQ ID NO) |
|---|---|---|
| Anti-PD-L1 hole-Ck | 25 | 86 |
| Anti-PD-L1 VH hole CH1-Fc | 26 | 87 |

TABLE 13

Components and sequences of anti-HER2 Fab/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-HER2 VL-Cκ | 27 | 88 |
| IRES | 3 | — |
| Anti-HER2 VH-CH1 | 28 | 89 |
| Anti-CD3 scFv | 5 | 66 |

TABLE 14

Components and sequences of anti-CD3 Fab/anti-HER2 scFv BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL-Cκ | 6 | 67 |
| IRES | 3 | — |
| Anti-CD3 VH-CH1 | 7 | 68 |
| Anti-HER2 scFv | 29 | 90 |

TABLE 15

Components and sequences of anti-HER2 scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-HER2 scFv | 30 | 91 |
| Anti-CD3 scFv | 18 | 79 |

TABLE 16

Components and sequences of anti-CD3 knob/anti-HER2 hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Ck | 10 | 71 |
| IRES | 3 | — |
| Anti-CD3 VH knob CH1-Fc | 11 | 72 |
| Anti-HER2 hole-Ck | 31 | 92 |
| Anti-HER2 VH hole CH1-Fc | 32 | 93 |

TABLE 17

Components and sequences of anti-FAP Fab/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-FAP VL-Cκ | 33 | 94 |
| IRES | 3 | — |
| Anti-FAP VH-CH1 | 34 | 95 |
| Anti-CD3 scFv | 5 | 66 |

TABLE 18

Components and sequences of anti-CD3 Fab/anti-FAP scFv BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL-Cκ | 6 | 67 |
| IRES | 3 | — |
| Anti-CD3 VH-CH1 | 7 | 68 |
| Anti-FAP scFv | 35 | 96 |

TABLE 19

Components and sequences of anti-FAP scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-FAP scFv | 36 | 97 |
| Anti-CD3 scFv | 18 | 79 |

TABLE 20

Components and sequences of anti-CD3 knob/anti-FAP hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Ck | 10 | 71 |
| IRES | 3 | — |
| Anti-CD3 VH knob CH1-Fc | 11 | 72 |
| Anti-FAP hole-Ck | 37 | 98 |
| Anti-FAP VH hole CH1-Fc | 38 | 99 |

TABLE 21

Components and sequences of anti-EpCAM MOC31 Fab/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-EpCAM MOC31 VL-Cκ | 39 | 100 |
| IRES | 3 | — |
| Anti-EpCAM MOC31 VH-CH1 | 40 | 101 |
| Anti-CD3 scFv | 5 | 66 |

TABLE 22

Components and sequences of anti-CD3 Fab/anti-EpCAM MOC31 scFv BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL-Cκ | 6 | 67 |
| IRES | 3 | — |
| Anti-CD3 VH-CH1 | 7 | 68 |
| Anti-EpCAM MOC31 scFv | 41 | 102 |

TABLE 23

Components and sequences of anti-EpCAM MOC31 scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-EpCAM MOC31 scFv | 42 | 103 |
| Anti-CD3 scFv | 18 | 79 |

TABLE 24

Components and sequences of anti-CD3 knob/anti-EpCAM MOC31 hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Cκ | 10 | 71 |
| IRES | 3 | — |
| Anti-CD3 VH knob CH1-Fc | 11 | 72 |
| Anti-EpCAM MOC31 hole-Cκ | 43 | 104 |
| Anti-EpCAM MOC31 VH hole CH1-Fc | 44 | 105 |

TABLE 25

Components and sequences of anti-EpCAM MT201 Fab/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-EpCAM MT201 VL-Cκ | 45 | 106 |
| IRES | 3 | — |
| Anti-EpCAM MT201 VH-CH1 | 46 | 107 |
| Anti-CD3 scFv | 5 | 66 |

TABLE 26

Components and sequences of anti-CD3 Fab/anti-EpCAM MT201 scFv BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL-Cκ | 6 | 67 |
| IRES | 3 | — |
| Anti-CD3 VH-CH1 | 7 | 68 |
| Anti-EpCAM MT201 scFv | 47 | 108 |

TABLE 27

Components and sequences of anti-EpCAM MT201 scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-EpCAM MT201 scFv | 48 | 109 |
| Anti-CD3 scFv | 18 | 79 |

TABLE 28

Components and sequences of anti-CD3 knob/anti-EpCAM MT201 hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Cκ | 10 | 71 |
| IRES | 3 | — |
| Anti-CD3 VH knob CH1-Fc | 11 | 72 |
| Anti-EpCAM MT201 hole-Cκ | 49 | 110 |
| Anti-EpCAM MT201 VH hole CH1-Fc | 50 | 111 |

TABLE 29

Components and sequences of anti-CEA Fab/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-CEA VL-Cκ | 51 | 112 |
| IRES | 3 | — |
| Anti-CEA VH-CH1 | 52 | 113 |
| Anti-CD3 scFv | 5 | 66 |

TABLE 30

Components and sequences of anti-CD3 Fab/anti-CEA scFv BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL-Cκ | 6 | 67 |
| IRES | 3 | — |
| Anti-CD3 VH-CH1 | 7 | 68 |
| Anti-CEA scFv | 53 | 114 |

TABLE 31

Components and sequences of anti-CEA scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-CEA scFv | 54 | 115 |
| Anti-CD3 scFv | 18 | 79 |

TABLE 32

Components and sequences of anti-CD3 knob/anti-CEA hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Ck | 10 | 71 |
| IRES | 3 | — |
| Anti-CD3 VH knob CH1-Fc | 11 | 72 |
| Anti-CEA hole-Ck | 55 | 116 |
| Anti-CEA VH hole CH1-Fc | 56 | 117 |

TABLE 33

Components and sequences of anti-VCAM1 Fab/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-VCAM1 VL-Cκ | 57 | 118 |
| IRES | 3 | — |
| Anti-VCAM1 VH-CH1 | 58 | 119 |
| Anti-CD3 scFv | 5 | 66 |

TABLE 34

Components and sequences of anti-CD3 Fab/anti-VCAM1 scFv BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL-Cκ | 6 | 67 |
| IRES | 3 | — |
| Anti-CD3 VH-CH1 | 7 | 68 |
| Anti-VCAM1 scFv | 59 | 120 |

TABLE 35

Components and sequences of anti-VCAM1 scFv/anti-CD3 scFv BsAb

| Name | Nucleic Acid Sequence (SEQ ID NO) | Amino Acid Sequence (SEQ ID NO) |
|---|---|---|
| Signal Peptide | 1 | 63 |
| Anti-VCAM1 scFv | 60 | 121 |
| Anti-CD3 scFv | 18 | 79 |

TABLE 36

Components and sequences of anti-CD3 knob/anti-VCAM1 hole BsAb

| Name | Nucleic Acid Sequence (SEQ ID NO) | Amino Acid Sequence (SEQ ID NO) |
|---|---|---|
| Signal Peptide | 1 | 63 |
| Anti-CD3 VL knob Ck | 10 | 71 |
| IRES | 3 | — |
| Anti-CD3 VH knob CH1-Fc | 11 | 72 |
| Anti-VCAM1 hole-Ck | 61 | 122 |
| Anti-VCAM1 VH hole CH1-Fc | 62 | 123 |

Figure 4:
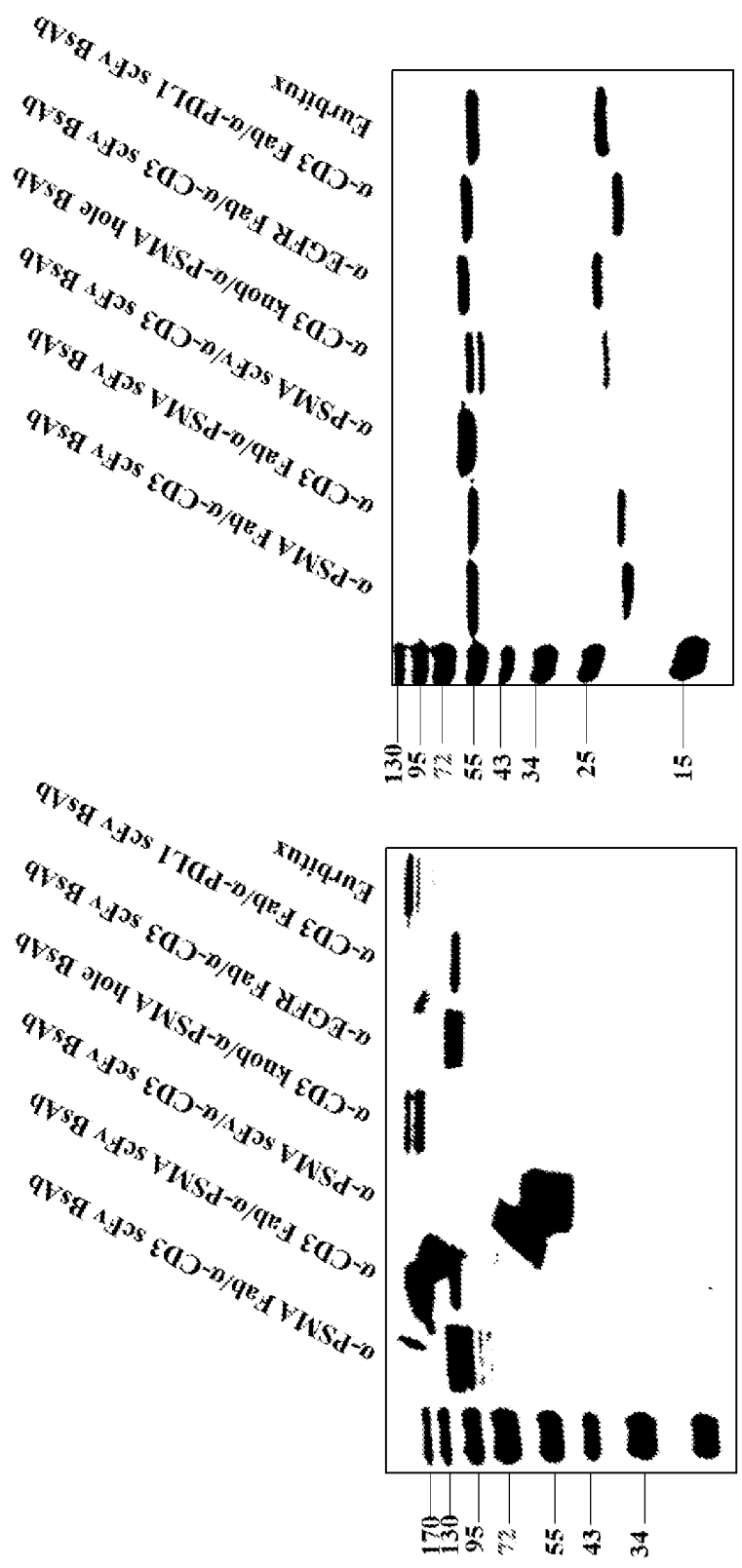
FIG. 4 depicts the results of SDS-PAGE analysis of BsAbs of Example 1.2 in non-reducing condition (left panel) and reducing condition (right panel)

1.2 Characterization of Anti-PSMA Fab/Anti-CD3 scFv, Anti-CD3 Fab/Anti-PSMA scFv, Anti-PSMA scFv/Anti-CD3 scFv and Anti-CD3 Knob/Anti-PSMA Hole BsAbs FIG. 4 depicts the SDS-PAGE analysis on anti-PSMA Fab/anti-CD3 scFv, anti-CD3 Fab/anti-PSMA scFv, anti-EGFR Fab/anti-CD3 scFv, and anti-CD3Fab/anti-PD-L1scFv BsAbs, which respectively composed of an Fab fragment about 95 kDa under reducing condition; on the other hand, a 170 kDa ant-CD3 knob/anti-PSMA hole BsAbs and a 50 kDa anti-PSMAscFv/antiCD3 scFv were respectively observed under non-reducing condition. Anti-EGFR antibody, Erbitux®, was included in the SDS PAGE as a positive control.

Bi-functional activities of the BsAbs were examined in this example by flow cytometry. Results are depicted in FIG. 3.

Figure 5:
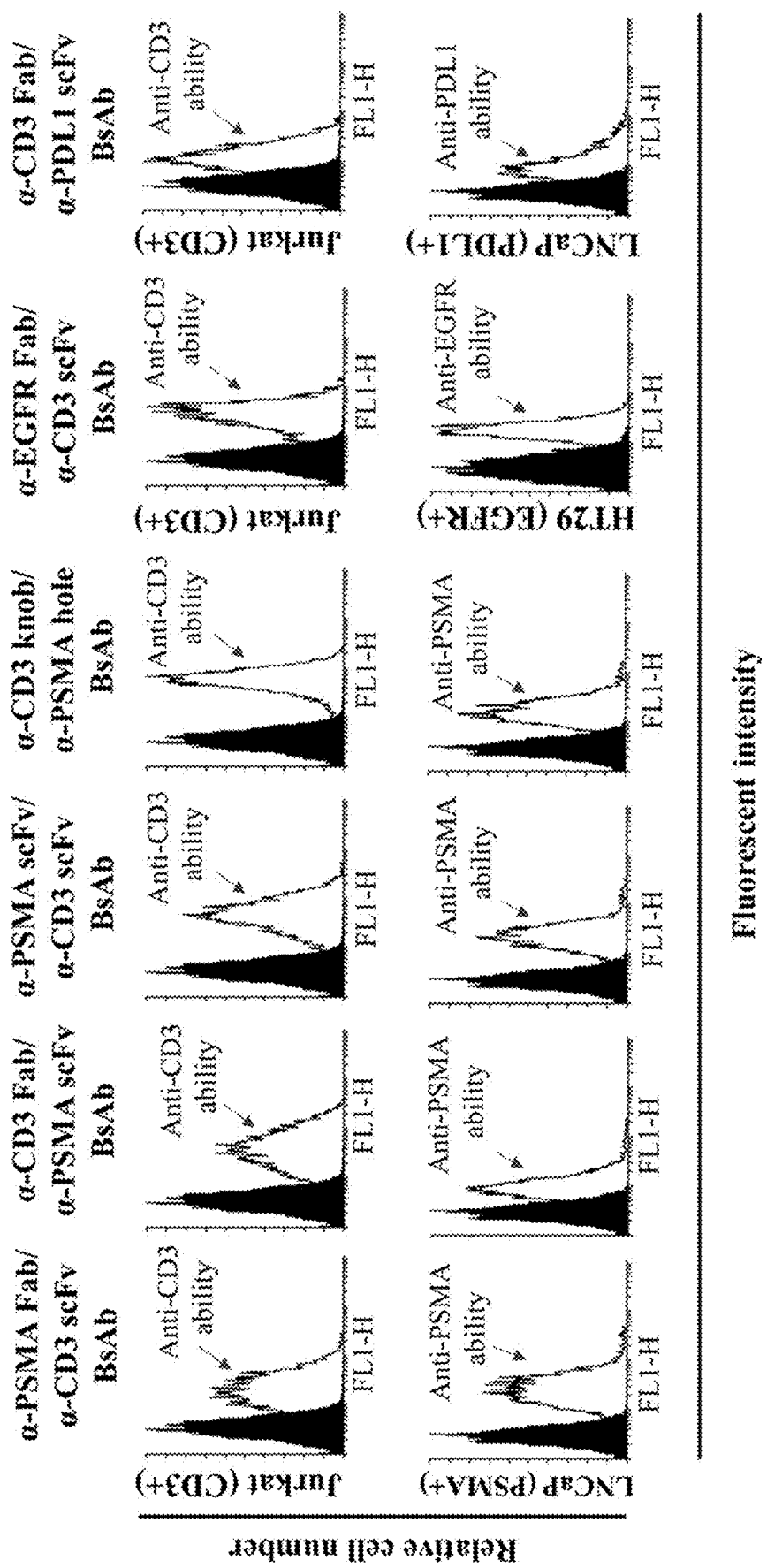
FIG. 5 depicts the flow cytometry analysis of the BsAbs of Example 1.2.

Each of the anti-PSMA Fab/anti-CD3 scFv, anti-CD3 Fab/anti-PSMA scFv, anti-PSMA scFv/anti-CD3 scFv and anti-CD3 knob/anti-PSMA hole BsAbs was capable of binding to CD3-positive T cells (i.e., Jurkat T cells) and to PSMA-positive prostate cancerous cells (i.e., LNCaP cells), while the anti-EGFR Fab/anti-CD3 scFv specifically recognized EGFR-positive cancerous cells (i.e., HT29 cells); and the anti-CD3 Fab/anti-PD-L1 scFv specifically recognized CD3-positive T cells (i.e., Jurkat T cells) and PD-L1-positive prostate cancerous cells (i.e., LNCaP cells). The data in FIG. 5 confirmed that the antibodies of Example 1 indeed possessed specificities to two different antigens.

1.3 Production of Humanized OKT3 Anti-Tumor/Anti-CD3 BsAbs

In this example, recombinant humanized OKT3 VH and VL sequences were produced in accordance with procedures described in the "Material and Methods" section. The humanized OKT3 VH and VL amino acid sequence, and respective CDRs are provided in Tables 37 and 38.

TABLE 37

Amino acid sequences of humanized OKT3 VH and its CDRs

| Name | Amino Acid Sequence (SEQ ID NO) |
|---|---|
| Anti-CD3 VH | 124 |
| HCDR1 | 125 |
| HCDR2 | 126 |
| HCDR3 | 127 |

TABLE 38

Amino acid sequences of humanized OKT3 VL and its CDRs

| Name | Amino Acid Sequence (SEQ ID NO) |
|---|---|
| Anti-CD3 VL | 128 |
| LCDR1 | 129 |
| LCDR2 | 130 |
| LCDR3 | 131 |

The humanized OKT3 VH and VL sequences could then fused with anti-tumor sequences described above in Tables 1 to 36 and thereby constructing desired humanized OKT3 anti-tumor/anti-CD3 BsAbs. Sequences of humanized OKT3 anti-CD3 scFv for constructing anti-tumor Fab/anti-CD3 scFv are provided in Table 39; sequences of humanized OKT3 anti-CD3 VL-Ck and VH-CH1 for constructing anti-CD3 Fab/anti-tumor scFv are provided in Table 40; sequences of humanized OKT3 anti-CD3 scFv for constructing anti-tumor scFv/anti-CD3 scFv are provided in Table 41; and sequences of humanized OKT3 anti-CD3 VL knob and VH knob for constructing anti-CD3 knob/anti-tumor hole are provided in Table 42.

TABLE 39

Sequences of humanized OKT3 anti-CD3 scFv for constructing anti-tumor Fab/anti-CD3 scFv

| Name | Nucleic Acid Sequence (SEQ ID NO) | Amino Acid Sequence (SEQ ID NO) |
|---|---|---|
| Anti-CD3 scFv | 132 | 133 |

TABLE 40

Sequences of humanized OKT3 anti-CD3 VL-Ck and VH-CH1 for constructing anti-CD3 Fab/anti-tumor scFv

| Name | Nucleic Acid Sequence (SEQ ID NO) | Amino Acid Sequence (SEQ ID NO) |
|---|---|---|
| Anti-CD3 VL-Ck | 134 | 135 |
| Anti-CD3 VH-CH1 | 136 | 137 |

TABLE 41

Sequences of humanized OKT3 anti-CD3 scFv for constructing anti-tumor scFv/anti-CD3 scFv

| Name | Nucleic Acid Sequence (SEQ ID NO) | Amino Acid Sequence (SEQ ID NO) |
|---|---|---|
| Anti-CD3 scFv | 138 | 139 |

TABLE 42

Sequences of humanized OKT3 anti-CD3 VL knob and VH knob for constructing anti-CD3 knob/anti-tumor hole

| Name | Nucleic Acid Sequence (SEQ ID NO) | Amino Acid Sequence (SEQ ID NO) |
|---|---|---|
| Anti-CD3 VL knob | 140 | 141 |
| Anti-CD3 VH knob CH1-Fc knob | 142 | 143 |

Example 2 Proliferation and Characterization of $CD3^+/CD8^+$ Cells Differentiated by BsAbs of Example 1

To produce T cells armed with BsAbs of Example 1, peripheral blood mononuclear cells (PBMCs) were isolated from the blood of healthy subjects, and differentiated by culturing in a media containing cytokine IL2 plus murine monoclonal antibody OKT3 or cytokine IL2 plus the BsAbs of Example 1.2 (i.e., anti-PSMA Fab/anti-CD3 scFv, anti-CD3 Fab/anti-PSMA scFv, anti-PSMA scFv/anti-CD3 scFv, and anti-CD3 knob/anti-PSMA hole BsAbs). The cultured cells were respectively harvested on days 7 and 14, and analyzed by flow cytometer with the aid of FITC-conjugated anti-CD3, anti-CD4, and anti-CD8 antibodies. Quantified results are summarized in Table 43 and FIG. 6.

Figure 6:
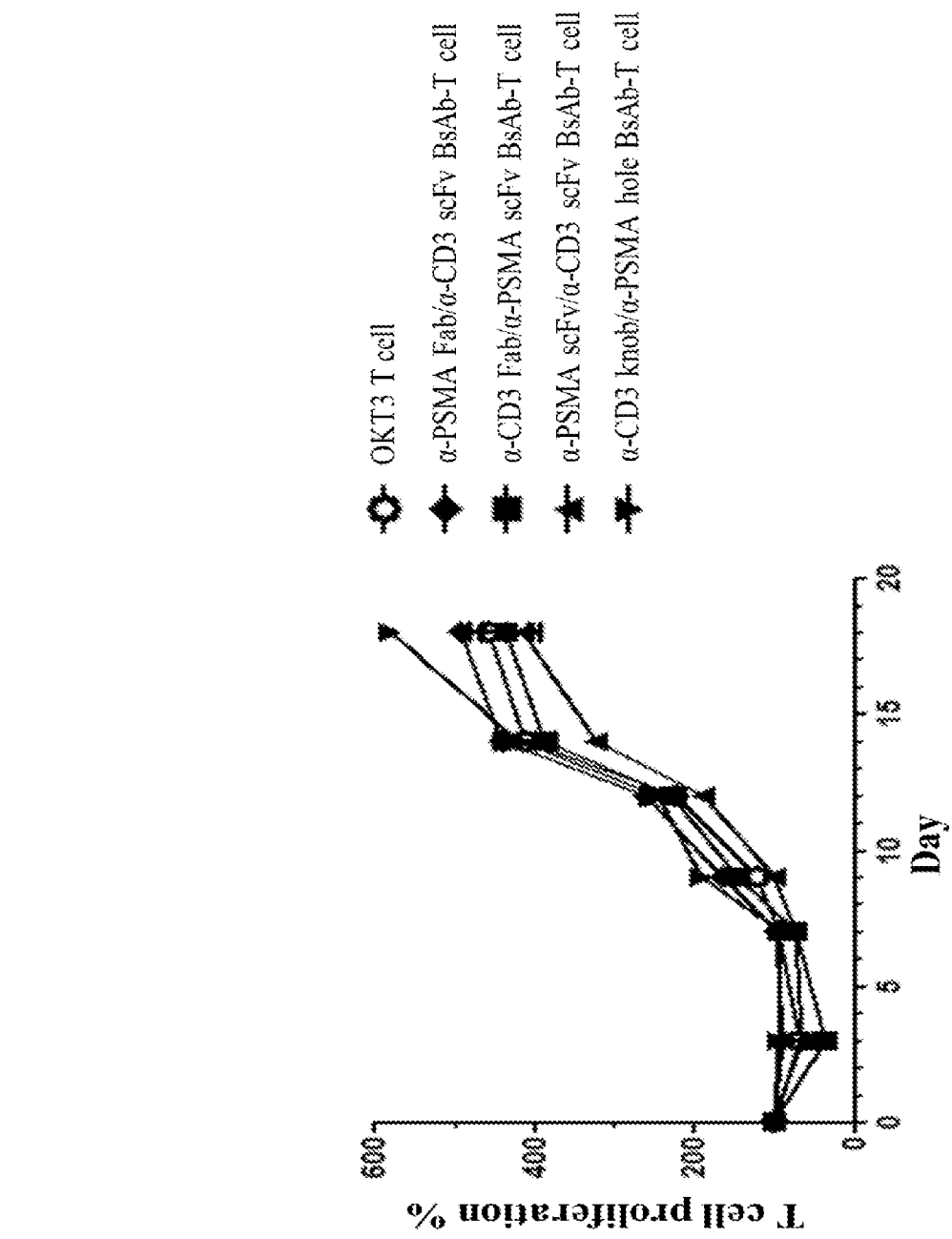
FIG. 6 depicts the differentiation and proliferation of T cells induced by murine OKT3 antibodies and BsAbs of Example 2 of the present disclosure.

The data in Table 43 indicates that the human BsAbs of the Example 1.2 were as effective as murine OKT3 in inducing differentiation of PBMCs into $CD3^+/CD8^+$ cells. Further, except those induced by anti-PSMA scFv/anti-CD3 scFv BsAb, the populations of $CD3^+$ cells induced by the BsAbs of Example 1.2 were over 80% after 7 days in culture, and over 90% after 14 days in culture, and the total numbers of the $CD3^+/CD^{8+}$ cells were about 4-5 folds after 18 days in culture (FIG. 6).

TABLE 43

Induced differentiation of PBMCs into $CD3^+/CD^{8+}$ cells by OKT3 or BsAbs of Example 1.2

| Day 7 T cell population | OKT3 T cell | α-PSMA Fab/ α-CD3 scFv BsAb-T cell | α-CD3 Fab/ α-PSMA scFv BsAb-T cell | α-PSMA scFv/ α-CD3 scFv BsAb-T cell | α-CD3 knob/ α-PSMA hole BsAb-T cell |
|---|---|---|---|---|---|
| CD3 (%) | 91.77 | 96.42 | 80.61 | 65.7 | 89.8 |
| CD4 (%) | 7.96 | 13.66 | 9.5 | 9.69 | 12.31 |
| CD8 (%) | 80.21 | 80.6 | 66.81 | 59.85 | 75.12 |
| Day 14 T cell population | OKT3 T cell | α-PSMA Fab/ α-CD3 scFv BsAb | α-CD3 Fab/ α-PSMA scFv BsAb | α-PSMA scFv/ α-CD3 scFv BsAb | α-CD3 knob/ α-PSMA hole BsAb |
| CD3 (%) | 92.71 | 97.8 | 92.14 | 64.75 | 95.04 |
| CD4 (%) | 2.27 | 9.19 | 2.32 | 4.29 | 14.4 |
| CD8 (%) | 73.02 | 86.4 | 72.51 | 51.95 | 85.06 |

To confirm whether the differentiated T cells indeed were armed with the BsAbs of Example 1.2, the anti-antigen fragments (e.g., anti-PSMA and anti-CD3) on the surfaces of the proliferated T cells were analyzed by flow cytometer with the aid of FITC-conjugated goat anti-human Fab antibody. Results are illustrated in FIG. 7.

Figure 7:
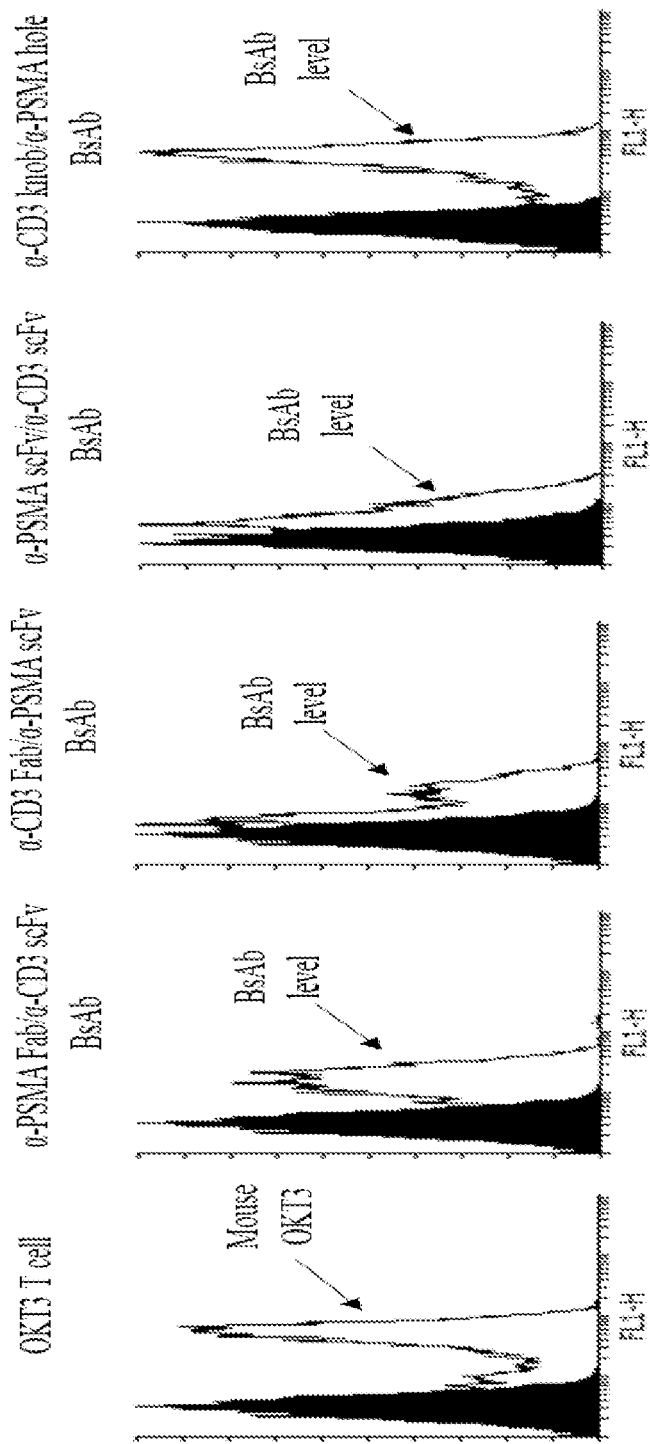
FIG. 7 is the flow cytometry analysis of the anti-antigen fragments on the surfaces of the proliferated T cells in accordance with one embodiment of the present disclosure.

The data in FIG. 7 confirmed that PBMCs after cultured with the BsAbs of Example 1.2 for 14 days were successfully differentiated into PSMA-specific T cells, by arming on their surfaces the anti-PSMA fragment of BsAbs of Example 1.2.

Example 3 Effect of T Cells of Example 2 on Cancerous Cells 3.1 Cytotoxicity Effect of T Cells of Example 2

The cancer cell killing effect of $CD3^+/CD8^+$ T cells respectively differentiated by the murine OKT3 and BsAbs of Example 1.2 were evaluated in LNCaP ($PSMA^+$) cells by CytoTox 96® Non-Radioactive Cytotoxicity Assay (Promega, G1780) in accordance with the manufacture's instruction. Results are summarized in Table 44 and FIG. 8.

Figure 8:
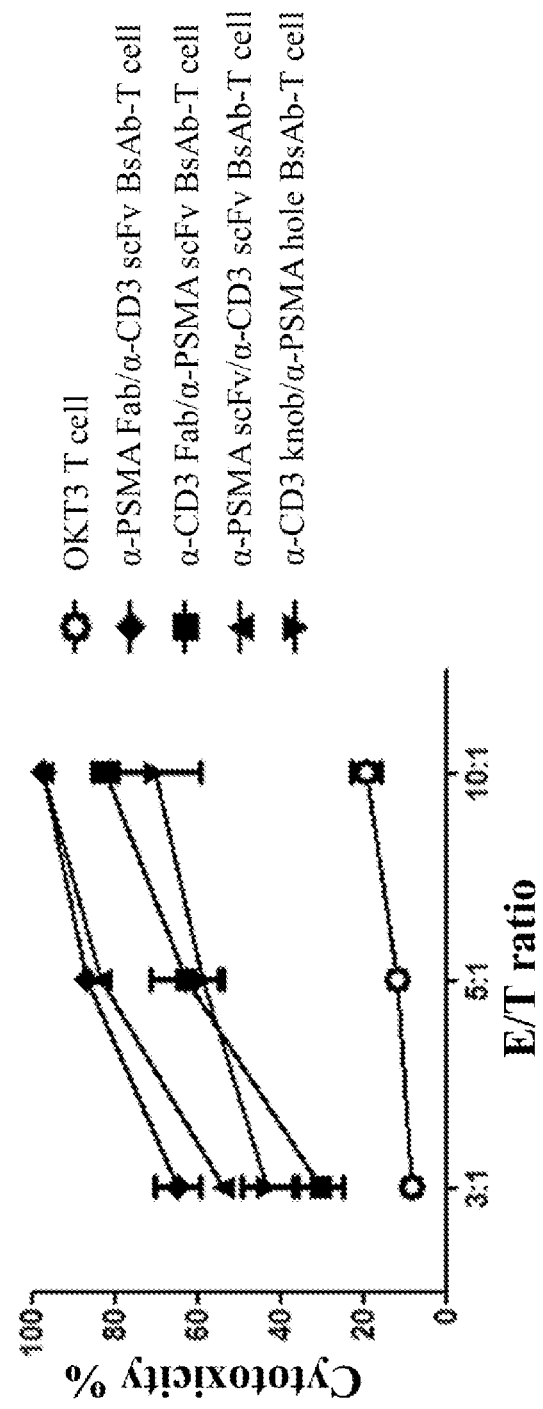
FIG. 8 depicts the cytotoxicity analysis of murine OKT3 T cells and T cells of Example 2 on prostate cancer cell line LNCaP in accordance with one embodiment of the present disclosure.

It was found that about 8.4%, 11.6% and 19.3% of LNCaP cells were killed by $CD3^+/CD8^+$ T cells induced by murine OKT3 at the effect cells to target cells ratio (E/T ratio) of 3:1, 5:1 and 10:1, respectively; whereas about 65%, 87% and 97% of LNCaP cells were killed by T cells armed with anti-PSMAFab/anti-CD3scFv BsAb at the same E/T ratio. Similar improved cytotoxicity effects were also found with T cells armed with anti-CD3 Fab/anti-PSMA scFv, anti-PSMA scFv/anti-CD3 scFv, and anti-CD3 knob/anti-PSMA hole BsAbs (FIG. 8).

Figure 9:
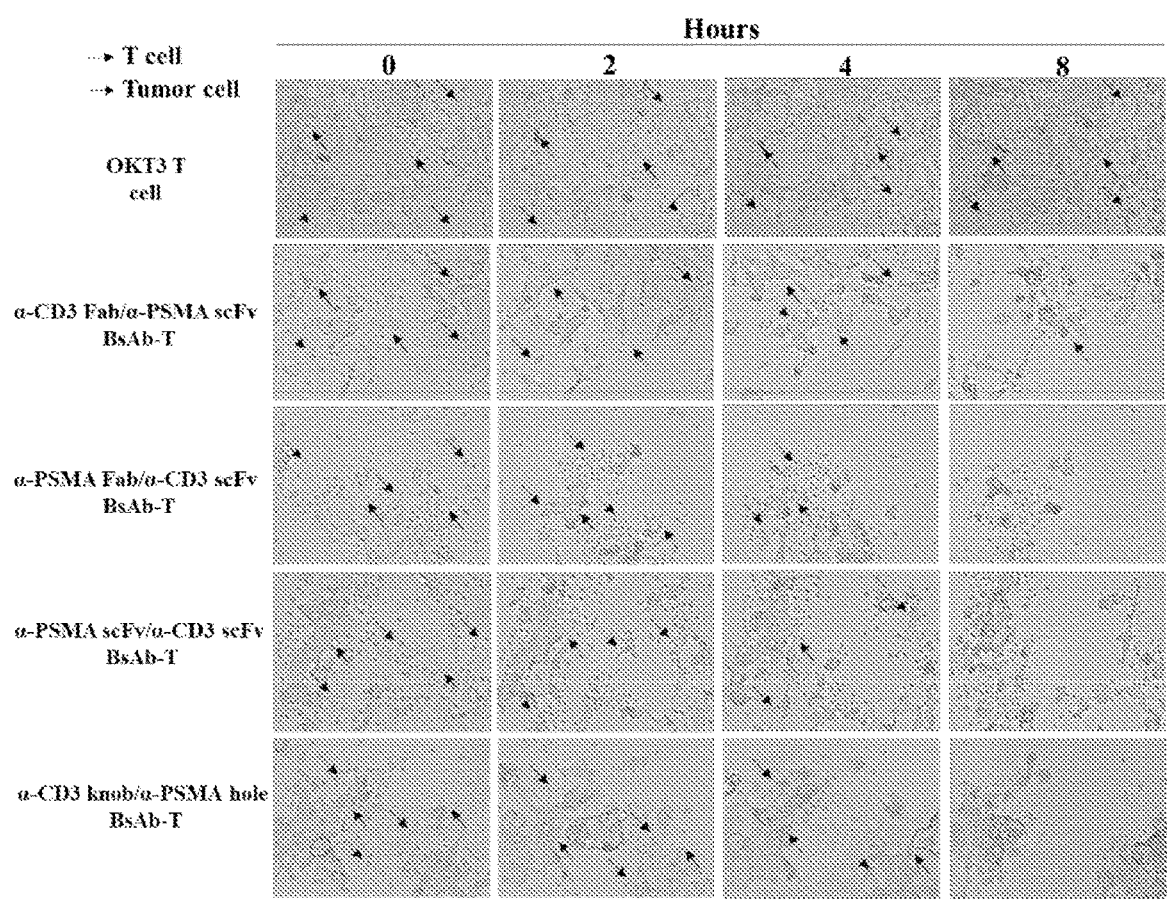
FIG. 9 are photographs depicting respective binding of murine OKT3 T cells and T cells of Example 2 on tumor cells in accordance with one embodiment of the present disclosure.

Imagine analysis further revealed that upon contacting with the tumor cells, significant portion of the T cells of Example 2 (or T cells armed with anti-CD3 Fab/anti-PSMA scFv, anti-PSMA scFv/anti-CD3 scFv, or anti-CD3 knob/anti-PSMA hole BsAbs of Example 1) bound specifically onto the surface of LNCaP cells, whereas T cells differentiated by murine OKT3 remained mostly un-bound even after incubation for 8 hrs (FIG. 9).

then the mixture was added to $PSMA^+$ cancer cells (i.e., LNCaP cells). The cancer cell killing effect was evaluated by cytotoxicity assay as that in Example 3.1, and the levels of cytokines in the supernatant collected from the LNCaP cells were analyzed by ELSA. Results are depicted in FIGS. 11 and 12.

Figure 11:
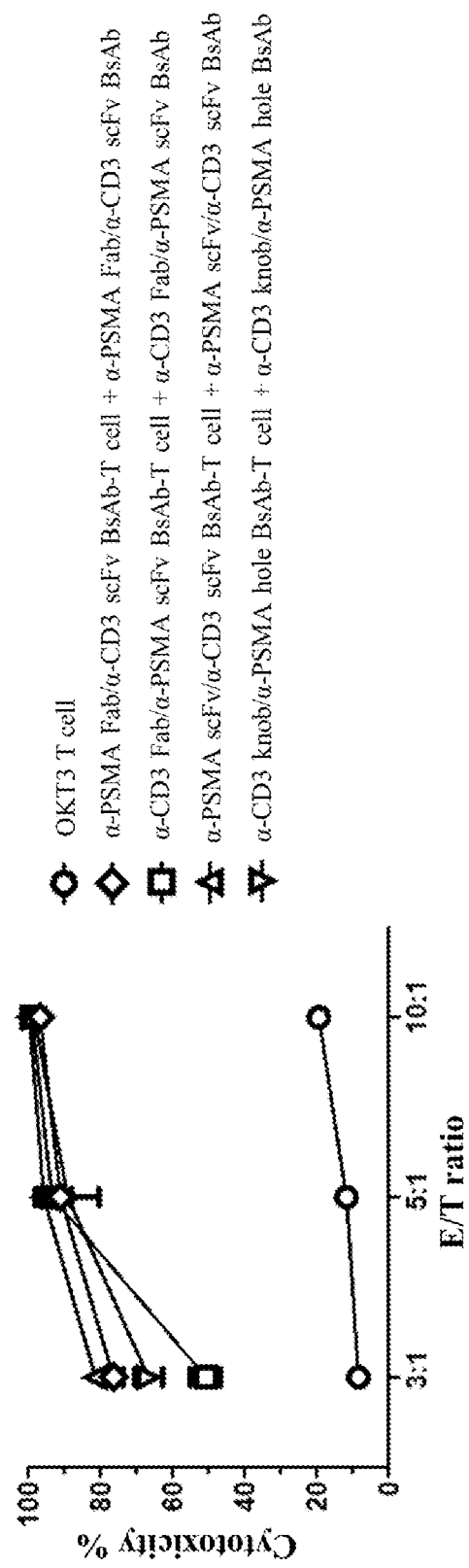
FIG. 11 is a line graph depicting the cytotoxicity analysis of murine OKT3 T cells and T cells of Example 2 further modified by BsAbs of Example 1.2 on LNCaP cells at various E/T ratios in accordance with one embodiment of the present disclosure.
Figure 12:
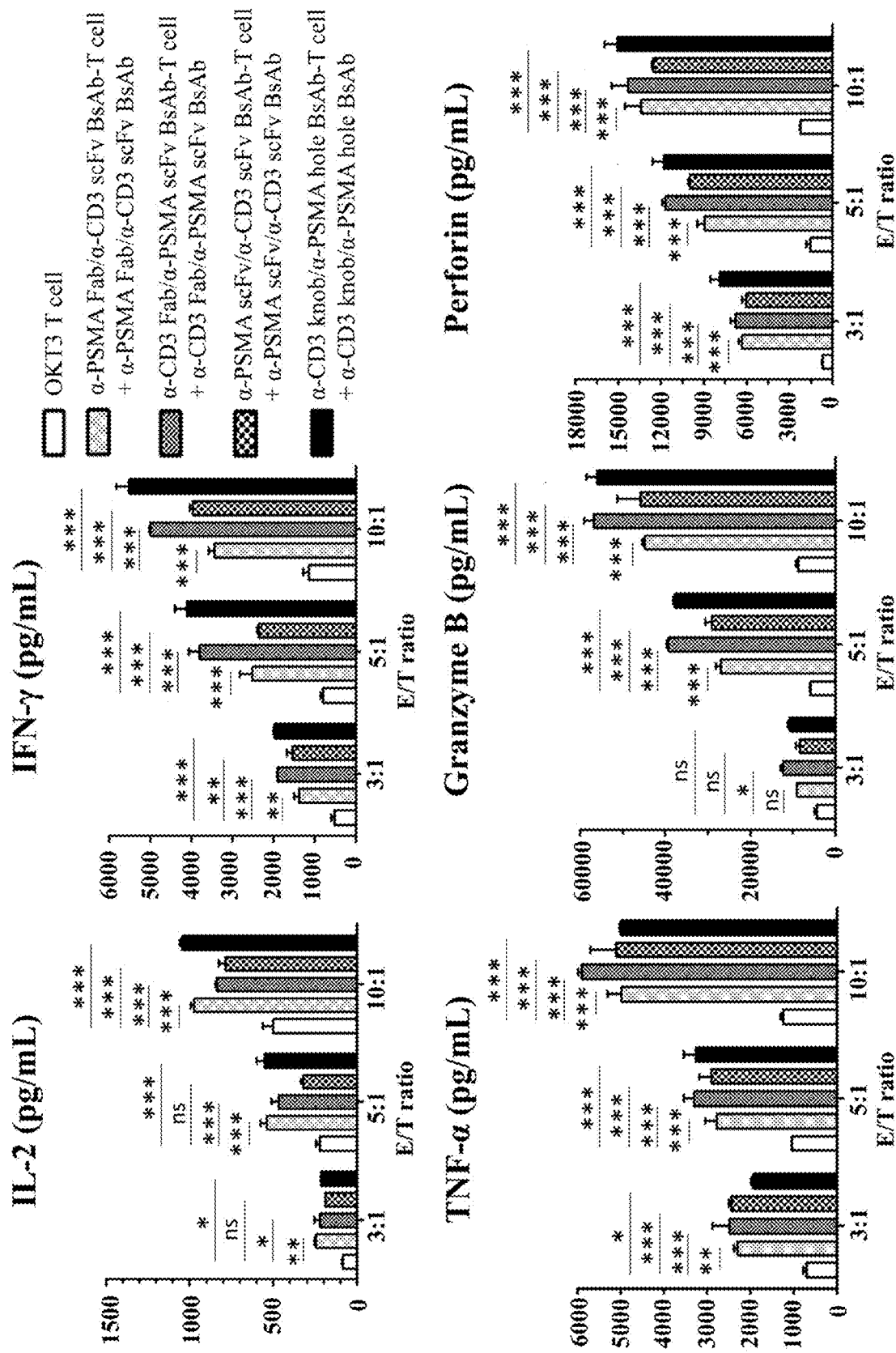
FIG. 12 are bar graphs depicting respective levels of cytokines secreted by murine OKT3 T cells and T cells of Example 2 further modified with BsAbs of Example 1.2 at various E/T ratios in accordance with one embodiment of the present disclosure.

As depicted in FIG. 11, T cells of Example 2 further modified with BsAbs of Example 1.2 exhibited much higher cell killing efficacy, with over 90% killing effect at E/TE/T ratio of 10:1, while T cells differentiated by murine OKT3 had a meager level of about 20% at the same E/TE/T ratio. As expected, the respective cytokine levels including IL-2, INF-γ, TNF-α, Granzyme B, and Perforin were also much higher than that of the control (i.e., T cells differentiated by murine OKT3) (FIG. 12).

3.4 Effect of T Cells Armed with Anti-CD3/Anti-PD-L1 BsAbs of Example 1 on Malignant Pancreatic Cancer or Triple-Negative Breast Cancer (TNBC)

Malignant pancreatic cancer and triple-negative breast cancer (TNBC) are both infamous for their high mortalities and extremely limited chance of being cured. In this example, effects of T cells armed with anti-CD3/anti-PD-L1 BsAbs of Example 1.2 on these two infamous cancers were tested using a malignant pancreatic cell line MIA PaCa-2 and a TNBC cell line MDA-MB-231.

Figure 13:
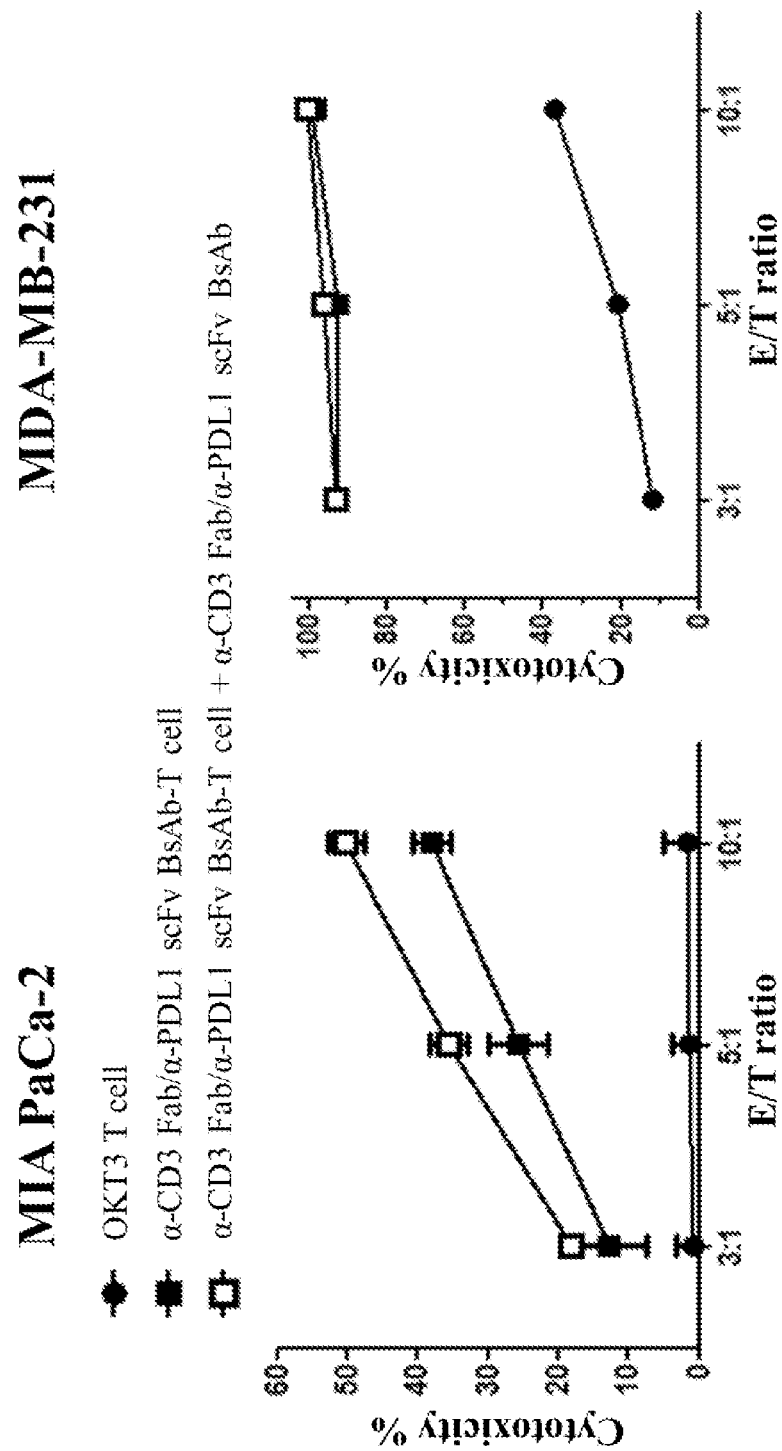
FIG. 13 illustrates the cytotoxicity analysis of murine OKT3 T cells, T cells of Example 2, or T cells of Example 2 further modified with anti-CD3 Fab/anti-PD-L1scFv BsAb on malignant pancreatic cell line MIA PaCa-2 and triple negative breast cancer (TNBC) cell line MDA-MB-231 in accordance with one embodiment of the present disclosure.

In malignant pancreatic cancer cells, T cells armed with anti-CD 3/anti-PD-L1 BsAbs of Example 1.2 exhibited much higher cytotoxic effects, as compared to that of the control T cells (i.e., differentiated T cells induced by murine OKT3), and the killing efficacy was enhanced even more if the T cells were further modified with anti-CD3/anti-PD-L1 BsAbs of Example 1.2. The cancer killing effect of the T cells armed with anti-CD3/anti-PD-L1 BsAbs of Example 1.2 was found to be even more significant in TNBC cells, with nearly 100% killing effect even at a low E/T ratio of 3:1; while the control T cells exhibited merely 10% killing efficacy at the same ratio (FIG. 13).

Imagine analysis revealed that T cells differentiated by murine OKT3 remained mostly un-bond to both MIA

TABLE 44

Cytotoxic effects of T cells respectively differentiated by murine OKT3 and BsAbs of Example 1.2

| Effect cell/<br>Target cell | OKT3<br>T cell | α-PSMA Fab/<br>α-CD3 scFv<br>BsAb T cell | α-CD3 Fab/<br>α-PSMA scFv<br>BsAb T cell | α-PSMA scFv/<br>α-CD3 scFv<br>BsAb T cell | α-CD3 knob/<br>α-PSMA hole<br>BsAb T cell |
|---|---|---|---|---|---|
| 3:1 | 8.4 ± 1.6 | 64.8 ± 4.4 | 30.3 ± 4.5 | 53.8 ± 0.5 | 43.1 ± 5.3 |
| 5:1 | 11.7 ± 1.0 | 87.0 ± 0.8 | 62.6 ± 7.0 | 83.4 ± 1.0 | 58.6 ± 3.3 |
| 10:1 | 19.4 ± 2.7 | 97.3 ± 1.3 | 82.2 ± 2.3 | 97.6 ± 1.4 | 70.4 ± 8.9 |

3.2 Characterization of the Cancer Cell Killing Efficacy of T Cells of Example 2

Figure 10:
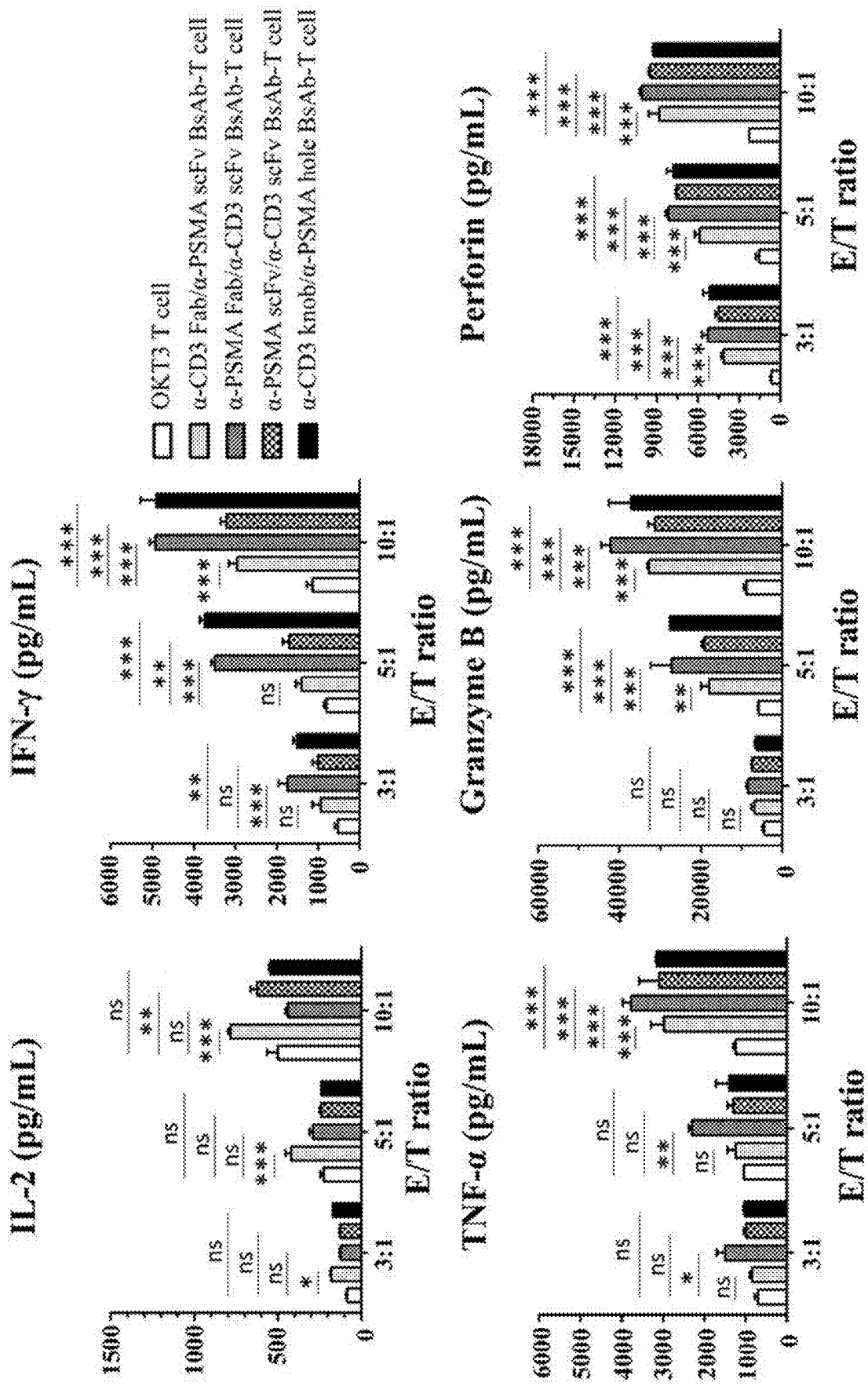
FIG. 10 are bar graphs depicting respective levels of cytokines secreted by murine OKT3 T cells and T cells of Example 2 at various effector:target ratios (E/T ratios) in accordance with one embodiment of the present disclosure.

To further analyze the cancer cell killing efficacy exhibited by T cells of Example 2 (or $CD3^+/CD8^+$ T cells armed with BsAbs of Example 1), the cytokines secreted therefrom were collected and analyzed by ELSA, and the result indicated that the levels of IL-2, INF-γ, TNF-α, Granzyme B, and Perforin were all significantly higher than that secreted from T cells differentiated by murine OKT3 (FIG. 10).

3.3 Enhanced Cancer Cell-Killing Effect by the T Cells of Example 2 Further Modified with BsAbs of Example 1.2

Figure 14A:
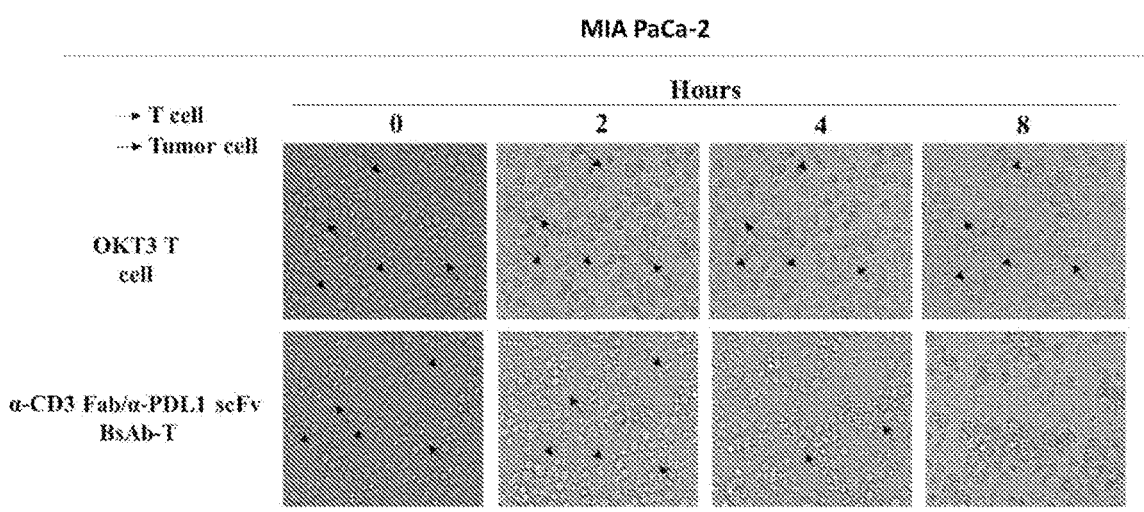
FIG. 14A are photographs illustrating respective binding of murine OKT3 T cells and T cells of Example 2 on MIA PaCa-2 cells in accordance with one embodiment of the present disclosure.
Figure 14B:
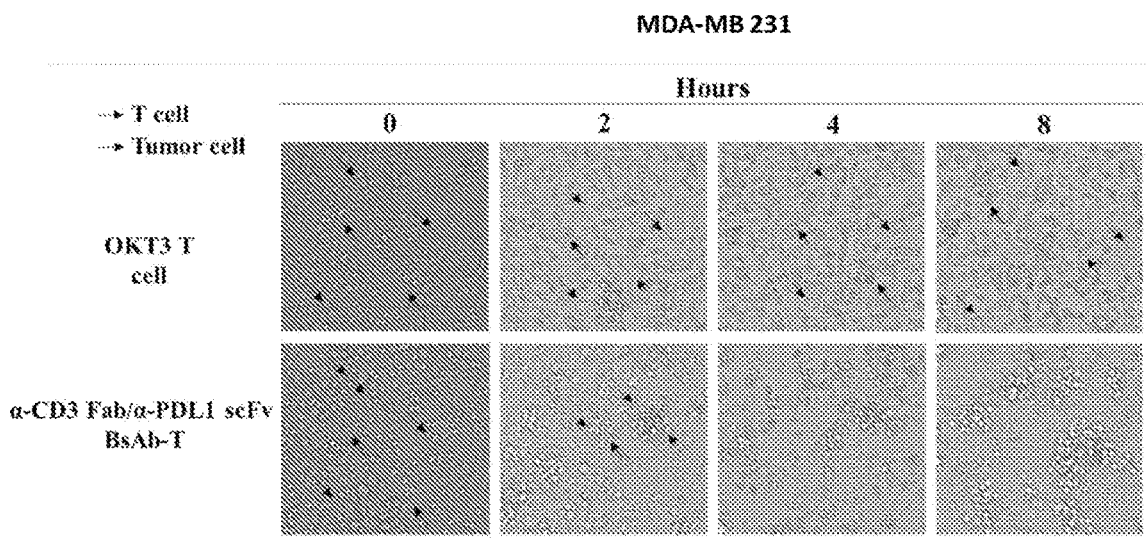
FIG. 14B are photographs illustrating respective binding of murine OKT3 T cells and T cells of Example 2 on MDA-MB-231 cells in accordance with one embodiment of the present disclosure.

In this example, BsAbs of Example 1.2 were further added to the culture media of the T cells of Example 2 at the E/TE/T ration of 3:1, 5:1, and 10:1, and cultivated for 18 hrs, PaCa-2 and MDA-MB-231 cells, while significant portion of MIA PaCa-2 and MDA-MB-231 cells became apoptotic after incubating with T cells that were further modified with anti-CD3/anti-PD-L1 BsAbs of Example 1.2 (FIGS. 14A and 14B).

3.5 Time Effects on the Amounts of BsAbs Remained on the Surfaces of T Cells

Figure 15:
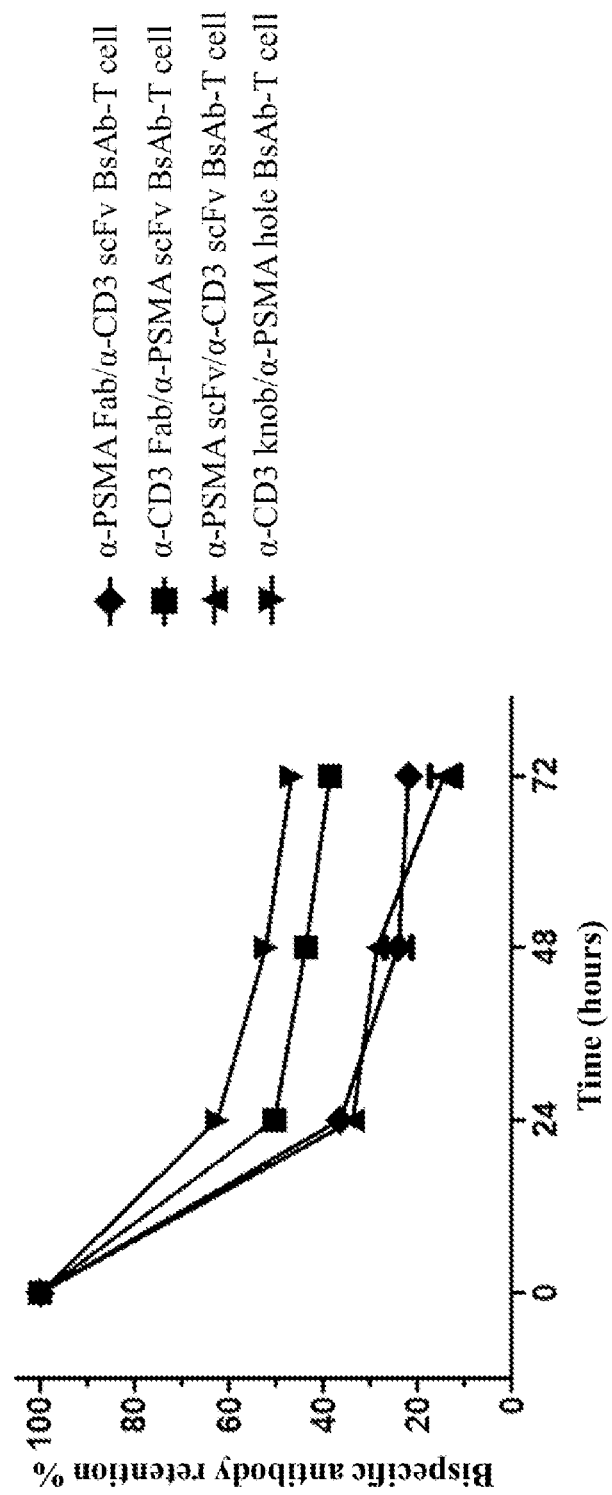
FIG. 15 illustrates the time course of residual amounts of BsAb of Example 1.2 remained on the surfaces of T cells in accordance with one embodiment of the present disclosure.

The anti-PSMA/anti-CD3 BsAbs of Example 1.2 were incubated with serum for various periods of time (i.e., 0, 24, 48 and 72 hrs), and analyzed by flow cytometry to evaluate the residual amounts of the BsAbs remain on the surfaces of T cells. Results are illustrated in FIG. 15.

It appeared that the amounts of BsAbs on the surface of the T cells declined with the time, among the four types or structures of BsAbs, anti-CD3 knob/anti-PSMA hole BsAb was least affected by degradation, about 47% of BsAb still remained on the T cell surface after 72 hrs, while the level of the anti-PSMA scFv/anti-CD3 scFv remained on the T cell surface dropped to a low level of 15%.

Example 4 Effects of Murine OKT3 T Cells Modified with BsAbs of Example 1.2

As the finding provided in Examples 1 to 4, murine OKT3 differentiated T cells were not as effective as the T cells of Example 2 (i.e., T cells armed with BsAbs of Example 1) in terms of the cancer killing effect, due to their low binding affinity to cancer cells and low levels of cytokines secreted therefrom. Accordingly, in this example, murine OKT3 T cells were modified by co-incubating with BsAbs of Example 1.2, then their cytotoxic effects in cancer cells and were evaluated.

4.1 Murine OKT3 T Cells Modified with BsAbs of Example 1.2

To modify the murine OKT3 T cells, about $3 \times 10^5$ murine OKT3 T cells were mixed with various amounts (8, 24, 120, 600 and 3,000 ng) of anti-PSMA/anti-CD3 BsAbs of example 1.2 and analyzed by flow cytometry. Results indicated that about 600 ng BsAbs of example 1.2 was sufficient to load the surfaces of murine OKT3 T cells with BsAbs of example 1.2 (data not shown).

Figure 16:
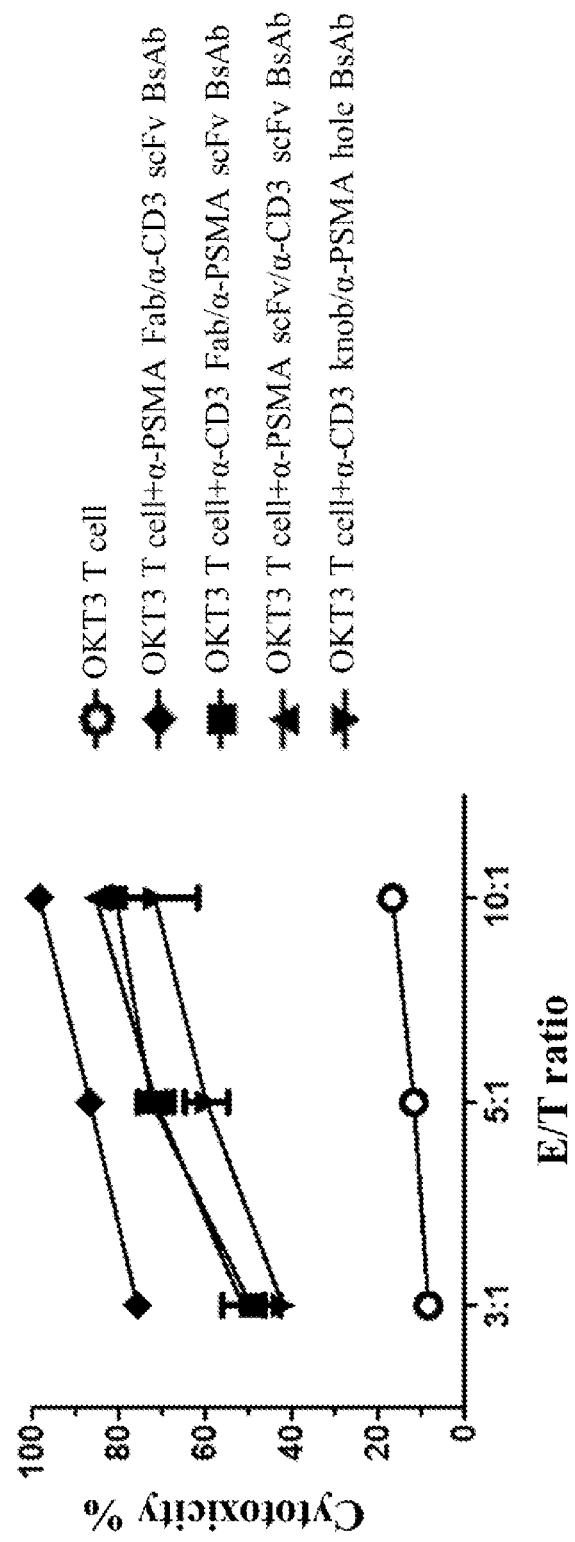
FIG. 16 illustrates the cytotoxicity analysis of murine OKT3 T cells and murine OKT3 T cells further modified with BsAbs of Example 1.2 on prostate cancer cell line LNCaP in accordance with one embodiment of the present disclosure.
Figure 17:
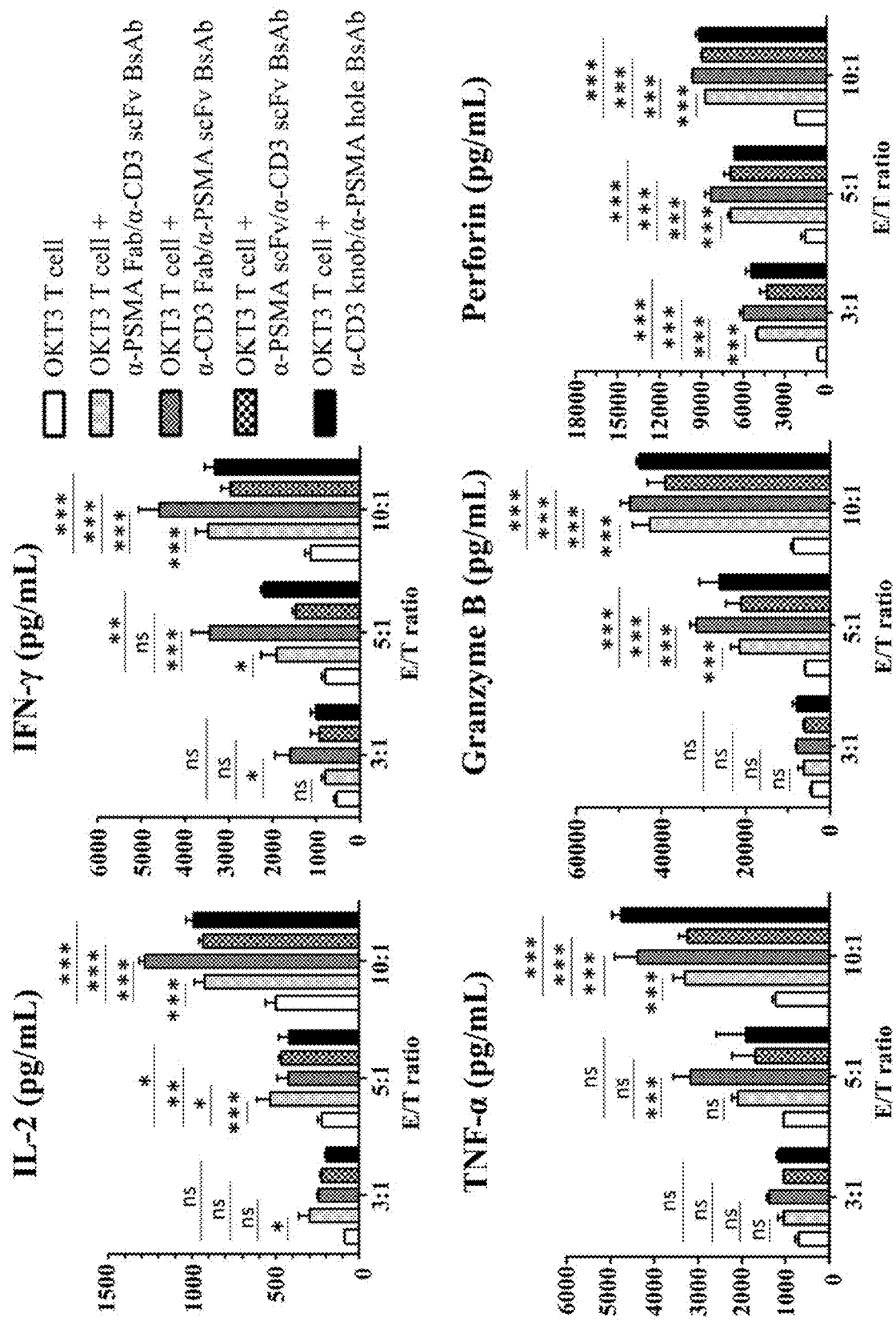
FIG. 17 are bar graphs depicting respective levels of cytokines secreted from murine OKT3 T cells and murine OKT3 T cells further modified with BsAbs of Example 1 in accordance with one embodiment of the present disclosure.

4.2 Effects of Murine OKT3 T Cells Modified with BsAbs of Example 1.2 on PSMA$^+$ Cells As expected, the cancer cell killing ability of murine OKT3 differentiated T cells toward LNCaP cells (PSMA$^+$) increased significantly after being modified with the BsAbs of Example 1, including anti-PSMA Fab/anti-CD3 scFv, anti-CD3 Fab/anti-PSMA scFv, anti-PSMA scFv/anti-CD3 scFv, and anti-CD3 knob/anti-PSMA hole, as compared to that before modification. Among which, murine OKT3 T cells modified with anti-PSMA Fab/anti-CD3 scFv exhibited near 100% cell killing effect at E/T ratio of 10:1 (FIG. 16). The respective cytokine levels including IL-2, INF-γ, TNF-α, Granzyme B, and Perforin secreted from murine OKT3 T cells modified with the BsAbs of Example 1.2 also increased significantly, compared with those of the control unmodified T cells (FIG. 17).

Figure 18:
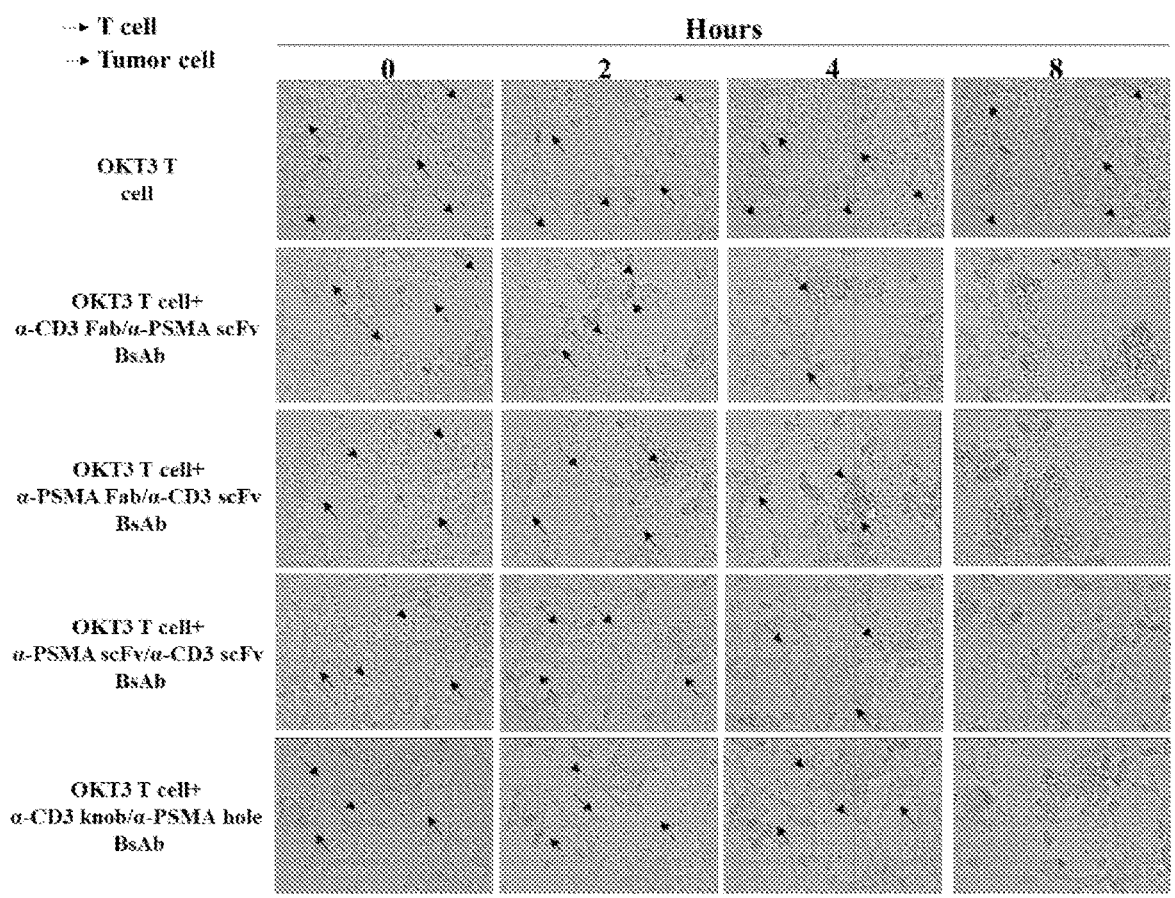
FIG. 18 are photographs depicting respective binding of murine OKT3 T cells and murine OKT3 T cells further modified with BsAbs of Example 1.2 on prostate tumor cells (LNCaP cells) in accordance with one embodiment of the present disclosure.

Imagine analysis revealed that murine OKT3 T cells modified with the anti-PSMA Fab/anti-CD3 scFv, anti-CD3 Fab/anti-PSMA scFv, anti-PSMA scFv/anti-CD3 scFv, or anti-CD3 knob/anti-PSMA hole BsAbs were more specifically bound to the surfaces of LNCaP cells, as compared with that of the unmodified OKT3 T cells (FIG. 18).

4.3 Effects of Murine OKT3 T Cells Modified with BsAbs of Example 1.2 on EGFR$^+$ Cells In this example, murine OKT3 T cells were modified with anti-EGFR Fab/anti-CD3 scFv BsAb of Example 1.2, and subjected to analysis to evaluate their capability in killing EGFR$^+$ cancer cells (i.e., HT29 cells).

Figure 19A:
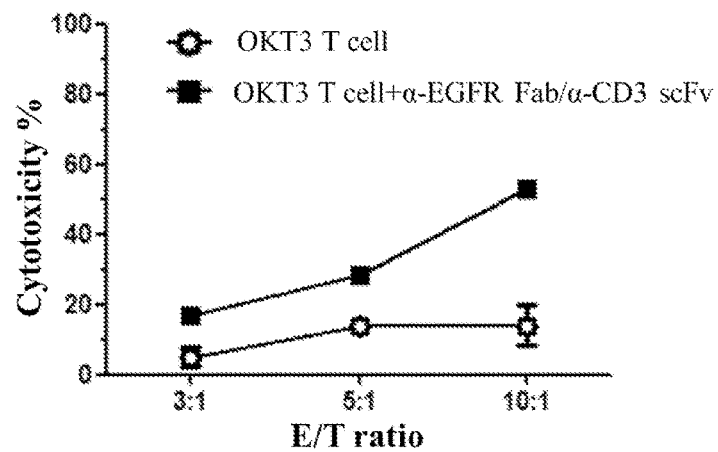
FIG. 19A illustrates the cytotoxicity analysis of murine OKT3 T cells and murine OKT3 T cells further modified with anti-EGFR Fab/anti-CD3 scFv of Example 1.2 on HT29 cells in accordance with one embodiment of the present disclosure.
Figure 19B:
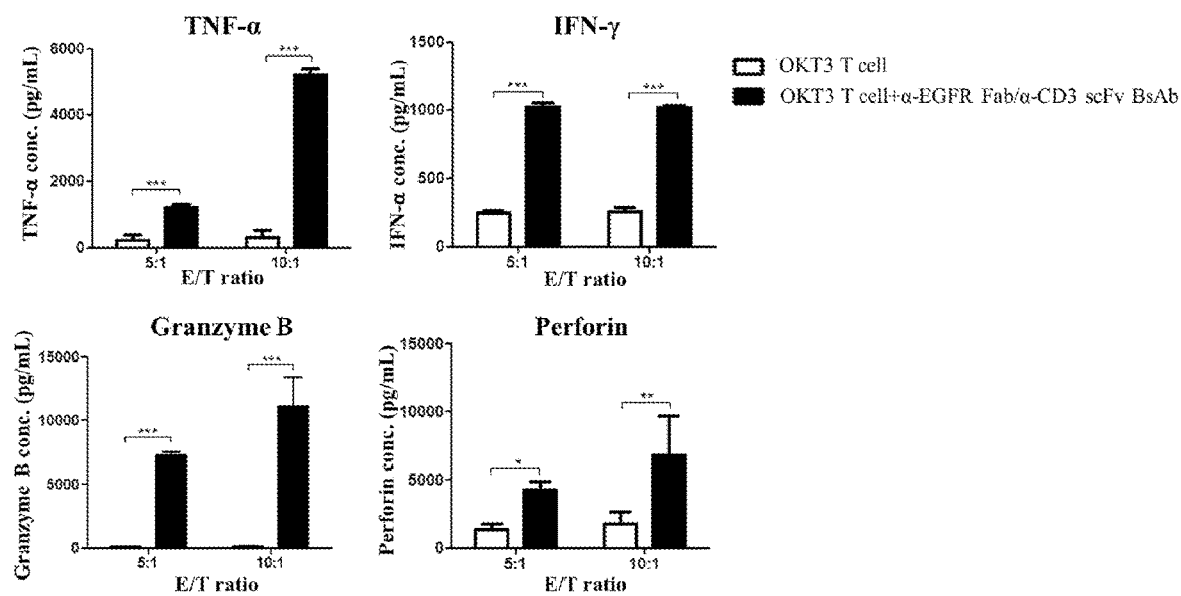
FIG. 19B are bar graphs depicting respective levels of cytokines secreted from murine OKT3 T cells and murine OKT3 T cells further modified with anti-EGFR Fab/anti-CD3 scFv of Example 1 in accordance with one embodiment of the present disclosure.

Similar to finding in Example 5.1, after being modified with anti-EGFR Fab/anti-CD3 scFv BsAb of Example 1.2, murine OKT3 T cells exhibited an enhanced cytotoxic effect, with about 50% cell killing effect at the E/T ratio of 10:1 (FIG. 19A), and enhanced cytokine levels in INF-γ, TNF-α, Granzyme B, and Perforin (FIG. 19B).

Figure 20:
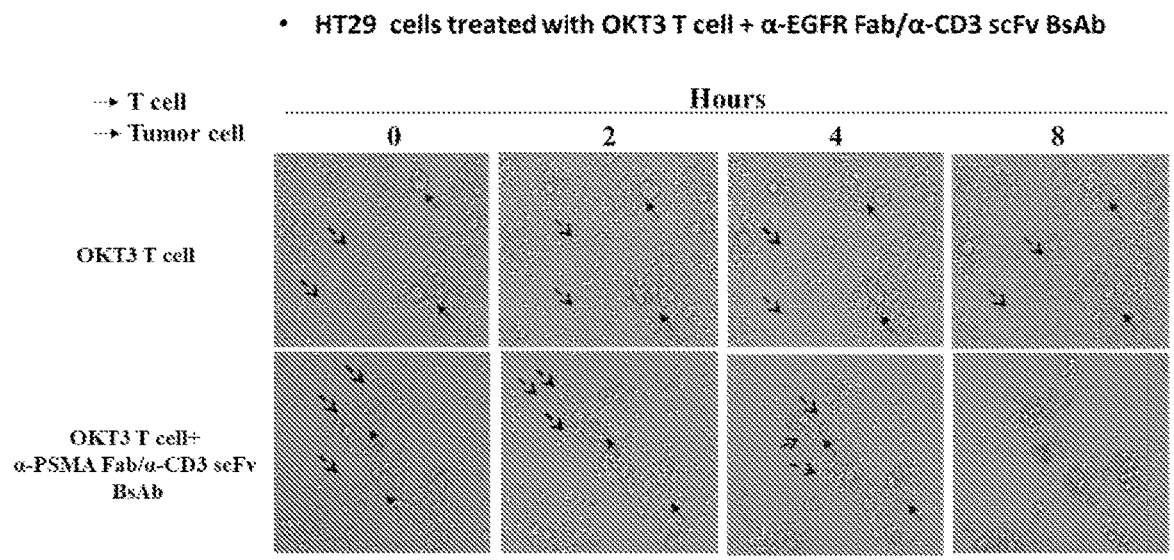
FIG. 20 are photographs depicting respective binding of murine OKT3 T cells and murine OKT3 T cells further modified with anti-EGFR Fab/anti-CD3 scFv of Example 1.2 on HT29 cells in accordance with one embodiment of the present disclosure.

Imagine analysis revealed that murine OKT3 T cells modified with the anti-EGFR Fab/anti-CD3 scFv BsAbs were more specifically bound to the surfaces of HT29 cells, as compared with that of the unmodified OKT3 T cells (FIG. 20).

4.4 Effects of Murine OKT3 T Cells Modified with BsAbs of Example 1.2 on PD-L1$^+$ Cells In this example, murine OKT3 T cells were modified with anti-CD3 Fab/anti-PD-L1 scFv BsAb of Example 1.2, and subjected to analysis to evaluate their capability in killing PD-L1$^+$ cancer cells (i.e., LNCaP cells).

Figure 21A:
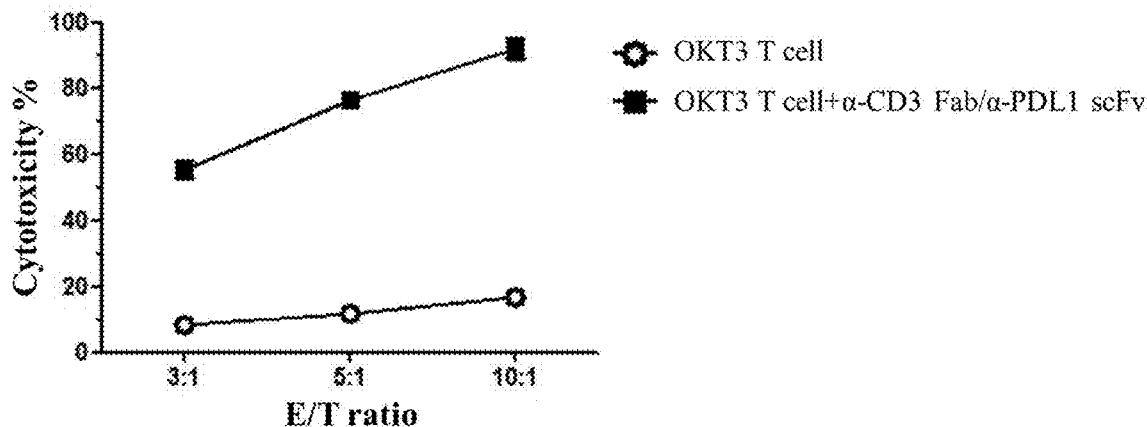
FIG. 21A illustrates the cytotoxicity analysis of murine OKT3 T cells and murine OKT3 T cells further modified with anti-CD3 Fab/anti-PD-L1 scFv of Example 1.2 on LNCaP cells in accordance with one embodiment of the present disclosure.
Figure 21B:
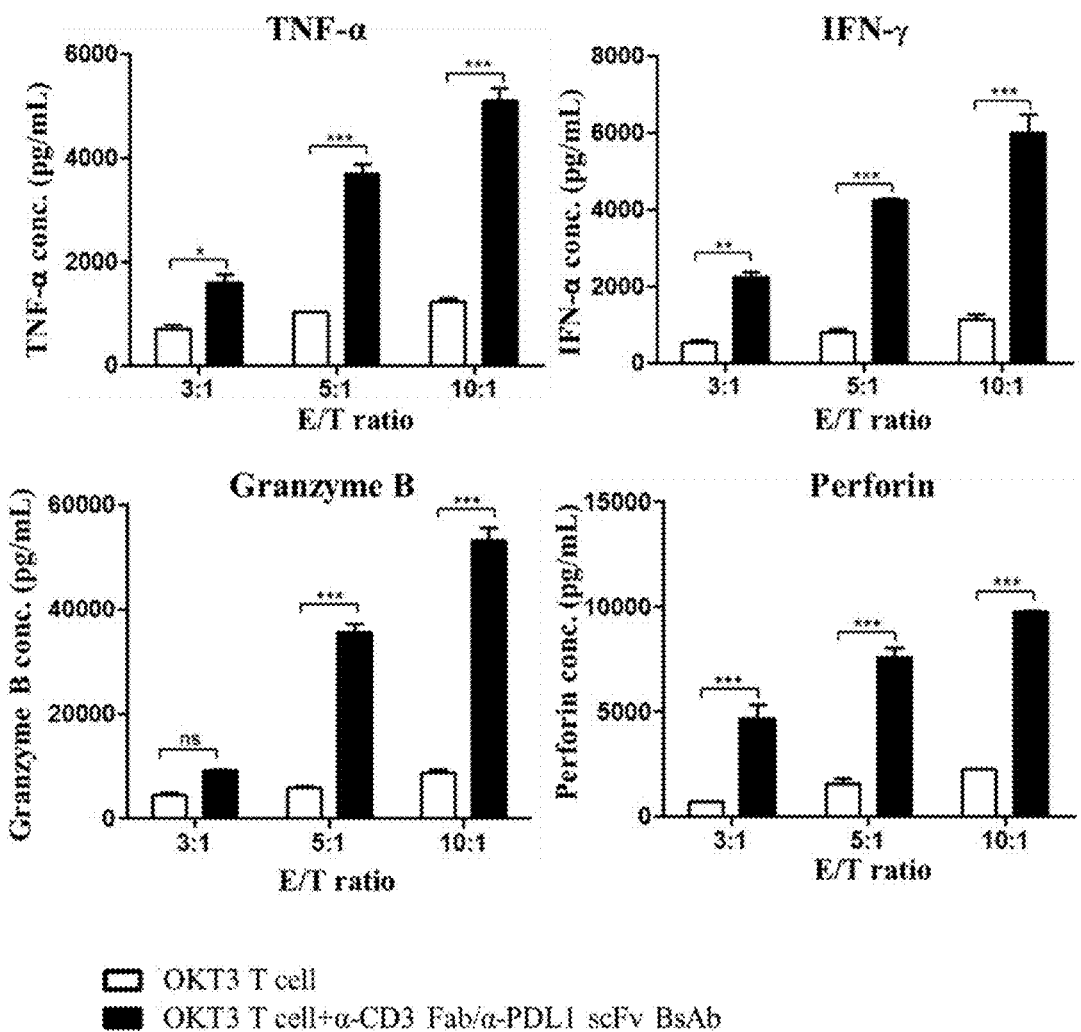
FIG. 21B are bar graphs depicting respective levels of cytokines secreted from murine OKT3 T cells and murine OKT3 T cells further modified with anti-CD3 Fab/anti-PD-L1 scFv of Example 1.2 in accordance with one embodiment of the present disclosure.

Similar to findings in Example 5.1 and 5.2, after being modified with anti-CD3 Fab/anti-PD-L1 scFv BsAb of Example 1.2, murine OKT3 T cells exhibited an enhanced cytotoxic effect, with about 92% cell killing effect at the E/T ratio of 10:1 (FIG. 21A), and enhanced cytokine levels in INF-γ, TNF-α, Granzyme B, and Perforin (FIG. 21B).

Figure 22:
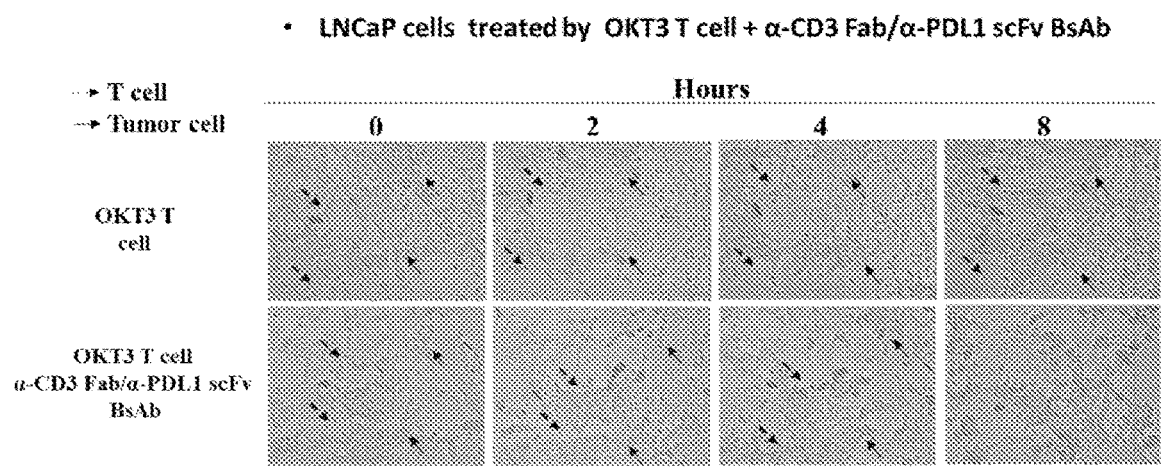
FIG. 22 are photographs depicting respective binding of murine OKT3 T cells and murine OKT3 T cells further modified with anti-CD3 Fab/anti-PD-L1 scFv of Example 1.2 on LNCaP cells in accordance with one embodiment of the present disclosure.

Imagine analysis revealed that murine OKT3 T cells modified with the anti-CD3 Fab/anti-PD-L1 scFv BsAb were more specifically bound to the surfaces of LNCaP cells, as compared with that of the unmodified OKT3 T cells (FIG. 22).

4.5 Effects of Murine OKT3 T Cells Modified with Anti-CD3 Fab/Anti-PD-L1 scFv of Example 1.2 on Malignant Pancreatic Cancer Cells and TNBC Cells In this example, the cancer killing effect of murine OKT3 T cells modified with anti-CD3 Fab/anti-PD-L1 scFv BsAbs of Example 1.2 were tested on malignant pancreatic cancer cell line MIA PaCa-2 (PD-L1$^+$ cells) and TNBC cells (MDA-MB-231 cells) in accordance with similar procedures described in Example 3.4.

Figure 23:
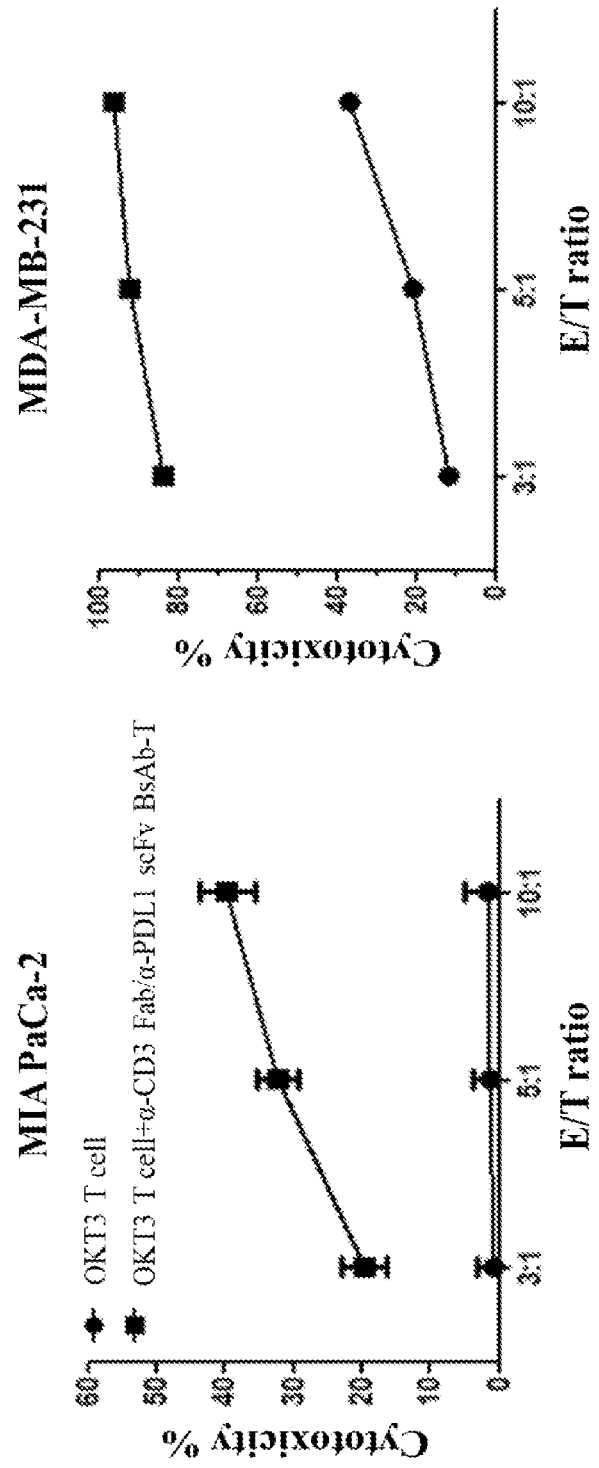
FIG. 23 illustrates the cytotoxicity analysis of murine OKT3 T cells, and murine OKT3 T cells further modified with anti-CD3 Fab/anti-PD-L1scFv BsAb on malignant pancreatic cell line MIA PaCa-2 and triple negative breast cancer (TNBC) cell line MDA-MB-231 in accordance with one embodiment of the present disclosure.

In malignant pancreatic cancer cells, murine OKT3 T cells modified with anti-CD3Fab/anti-PD-L1 scFv BsAbs of Example 1 exhibited much higher cytotoxic effect (about 40% cancer cells were killed), as compared to that of the control T cells (i.e., unmodified murine OKT3 T cells). The cancer killing effect was more significant in TNBC cells, with nearly 80% cancer cells were killed even at a low E/T ratio of 3:1; while the control T cells exhibited merely 20-30% killing efficacy at the same ratio (FIG. 23).

Figure 24A:
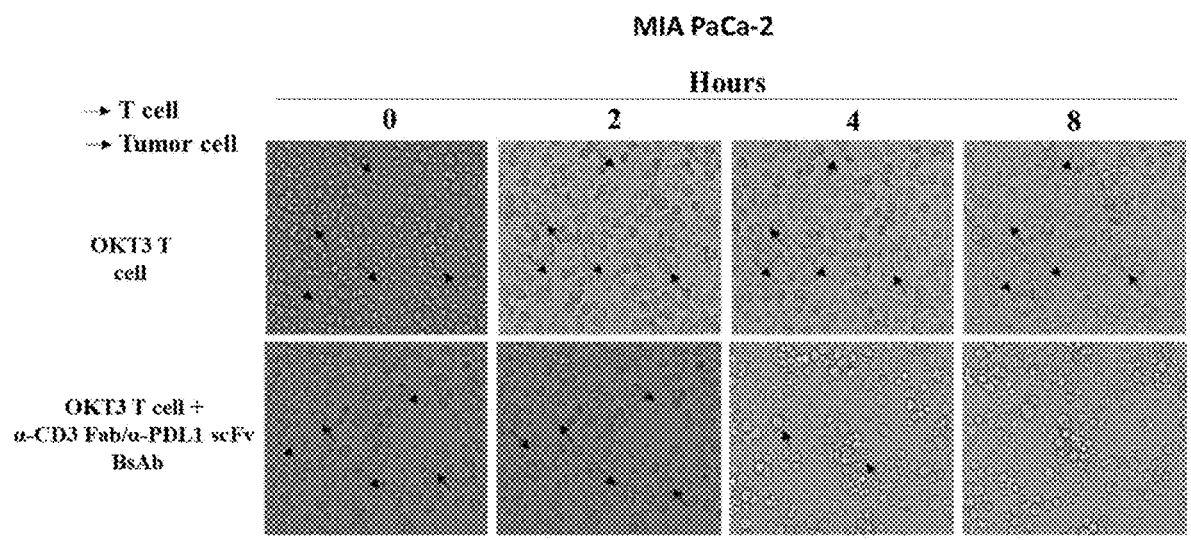
FIG. 24A are photographs depicting respective binding of murine OKT3 T cells and murine OKT3 T cells further modified with anti-CD3 Fab/anti-PD-L1 scFv of Example 1.2 on MIA PaCa-2 cells in accordance with one embodiment of the present disclosure.
Figure 24B:
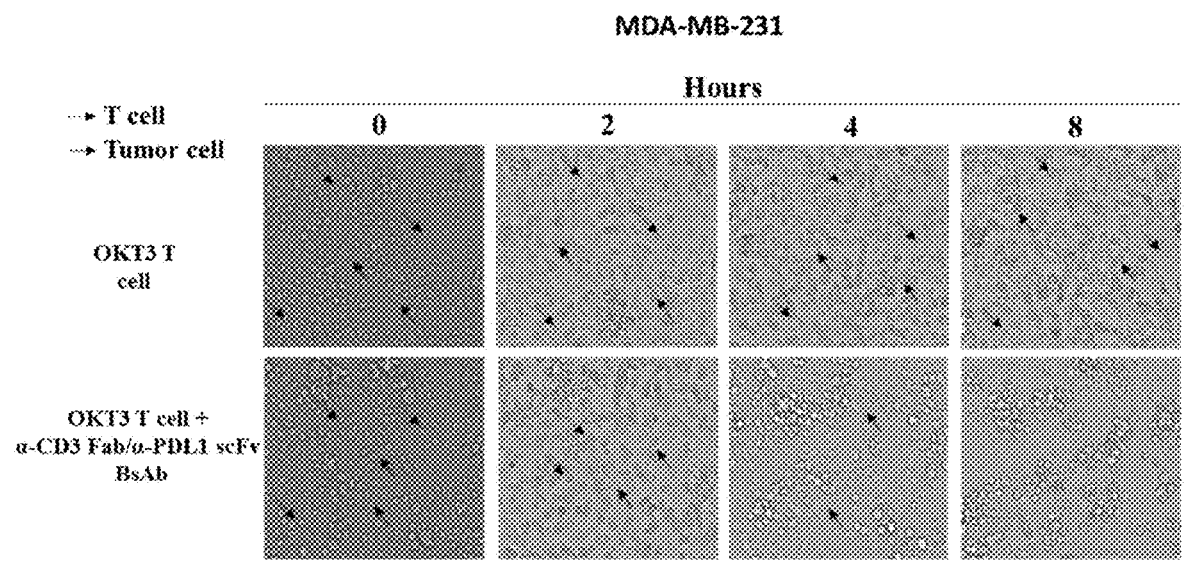
FIG. 24B are photographs depicting respective binding of murine OKT3 T cells and murine OKT3 T cells further modified with anti-CD3 Fab/anti-PD-L1 scFv of Example 1.2 on MDA-MB-231 cells in accordance with one embodiment of the present disclosure.

Imagine analysis revealed that murine OKT3 T cells modified with the anti-CD3 Fab/anti-PD-L1 scFv BsAb specifically bound to the surfaces of MIA PaCa-2 cells (FIG. 24A) and MDA-MB-231 cells (FIG. 24B), and resulted in enhanced cancer cell apoptosis, as compared with that of the unmodified OKT3 T cells.

Example 5 In Vivo Effects of Murine OKT3 T Cells Modified with BsAbs of Example 1

To investigate whether the BsAbs of Example 1 could improve the targeting effect of the murine OKT3 T cells, the murine OKT3 T cells were modified with anti-EGFR/anti-CD3 BsAb of Example 1.2, while at the same time labeling with a fluorescent indicator—NIR797. Then, the modified and labeled murine OKT3 T cells were injected into SCID mice bearing a heterogeneous EGFR$^+$ tumor (HT29 cells) through IV injection, and live images were taken respectively at 4 and 24 hrs using IVIS imaging system. The animals were sacrificed after 24 hrs, and the tumor per se and organs including heart, lung, kidney, spleen, liver, stomach, muscle, bone, large intestine, small intestine, pancreas, and blood, were harvested and analyzed by IVIS imaging system, respectively. Results are depicted in FIGS. 25 and 26.

Figure 25:
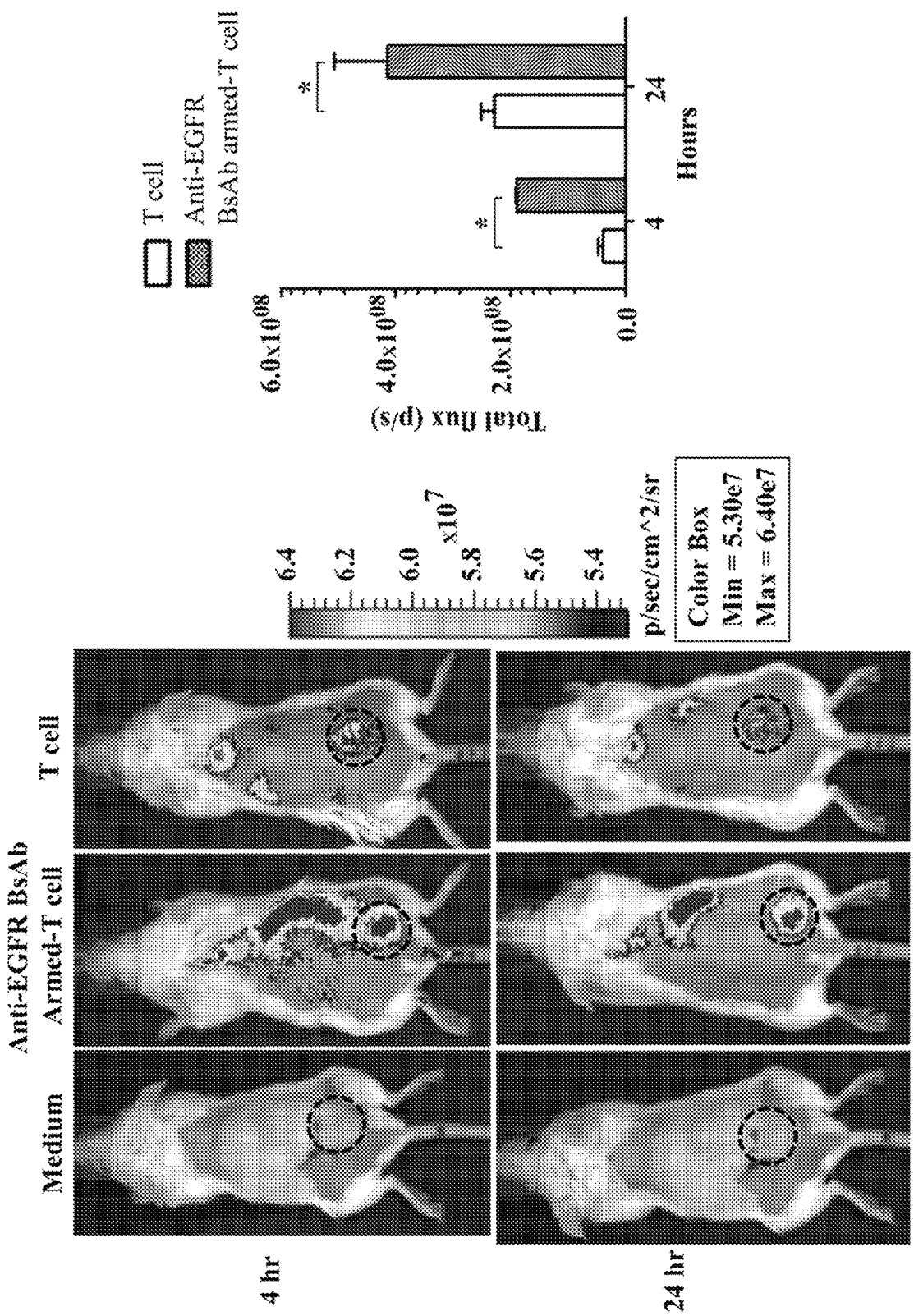
FIG. 25 illustrates the quantified fluorescent intensity in animals treated with the modified OKT3 T cells or the murine OKT3 T cells further modified with anti-EGFR Fab/anti-CD3 scFv of Example 1.2 in accordance with one embodiment of the present disclosure.

The photos in FIG. 25 revealed that fluorescent intensity in animals treated with the modified OKT3 T cells was found mainly concentrated on the tumor site, as compared to that treated with un-modified murine OKT3 T cells. The result confirmed that the murine OKT3 T cells modified with BsAbs of example 1 were indeed being targeted to the tumor, thereby resulted in an enhanced fluorescent intensity at the tumor site.

Figure 26:
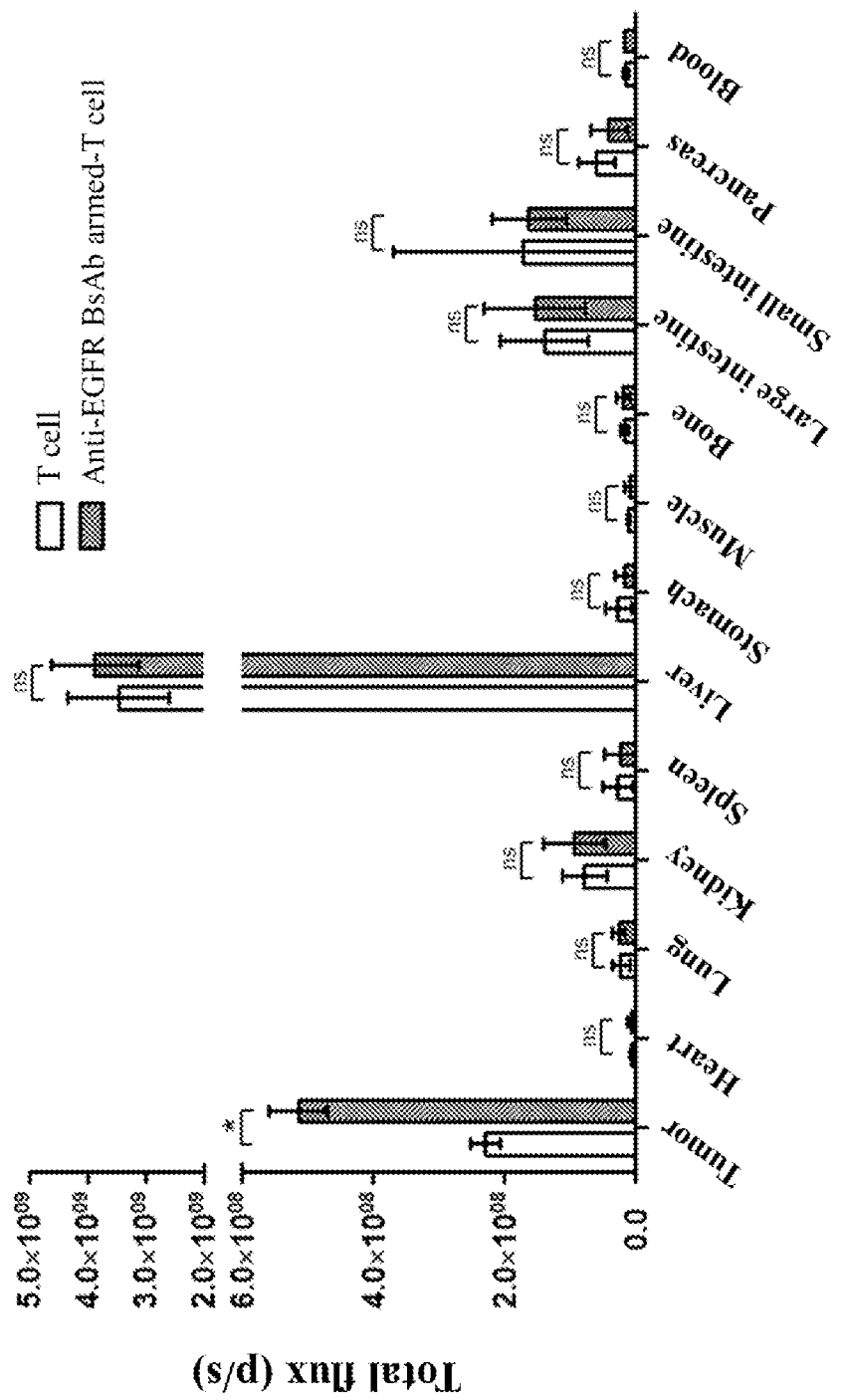
FIG. 26 illustrates the distribution pattern of the modified OKT3 T cells or the murine OKT3 T cells further modified with anti-EGFR Fab/anti-CD3 scFv of Example 1.2 in various organs of the test animal in accordance with one embodiment of the present disclosure.

Further, the modified T cells were found to be concentrated in the EGFR+ tumor per se, while the in vivo distribution pattern of these modified T cells was similar to that of a normal healthy animal (FIG. 26).

Figure 27A:
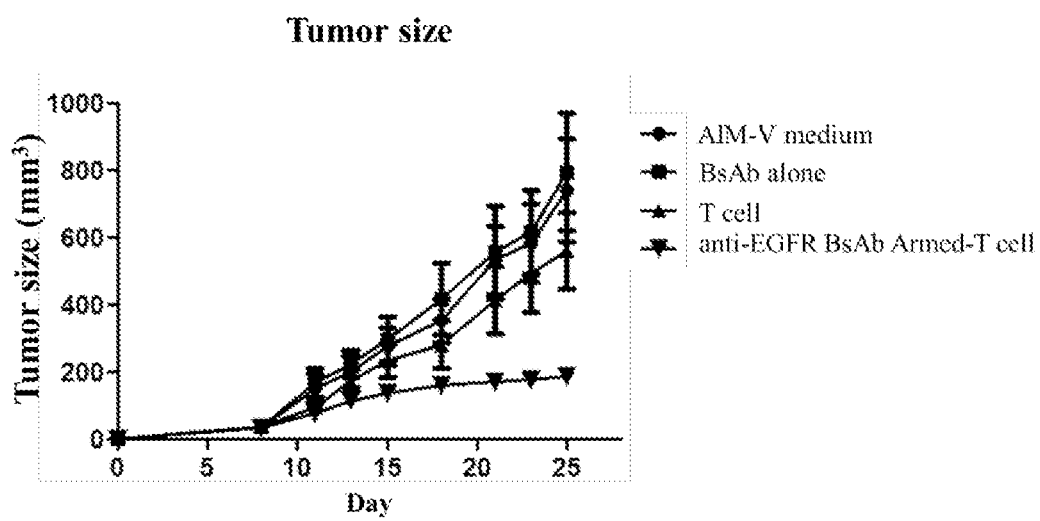
FIG. 27A is a line graph depicting changes in the size of a tumor treated by BsAb of Example 1.2, murine OKT3 T cells, or murine OKT3 T cells modified with anti-EGFR Fab/anti-CD3 scFv of Example 1.2 in accordance with one embodiment of the present disclosure.
Figure 27B:
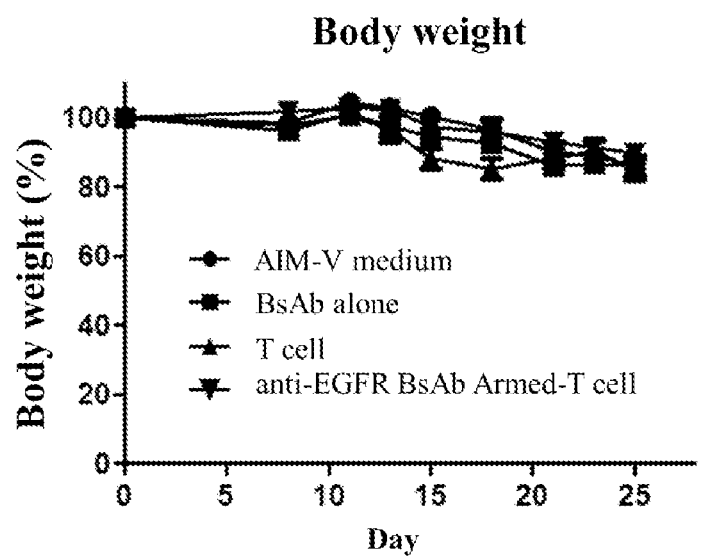
FIG. 27B is a line graph depicting changes in the body weight of the test animal treated by BsAb of Example 1.2, murine OKT3 T cells, or murine OKT3 T cells modified with anti-EGFR Fab/anti-CD3 scFv of Example 1.2 in accordance with one embodiment of the present disclosure.
Figure 27C:
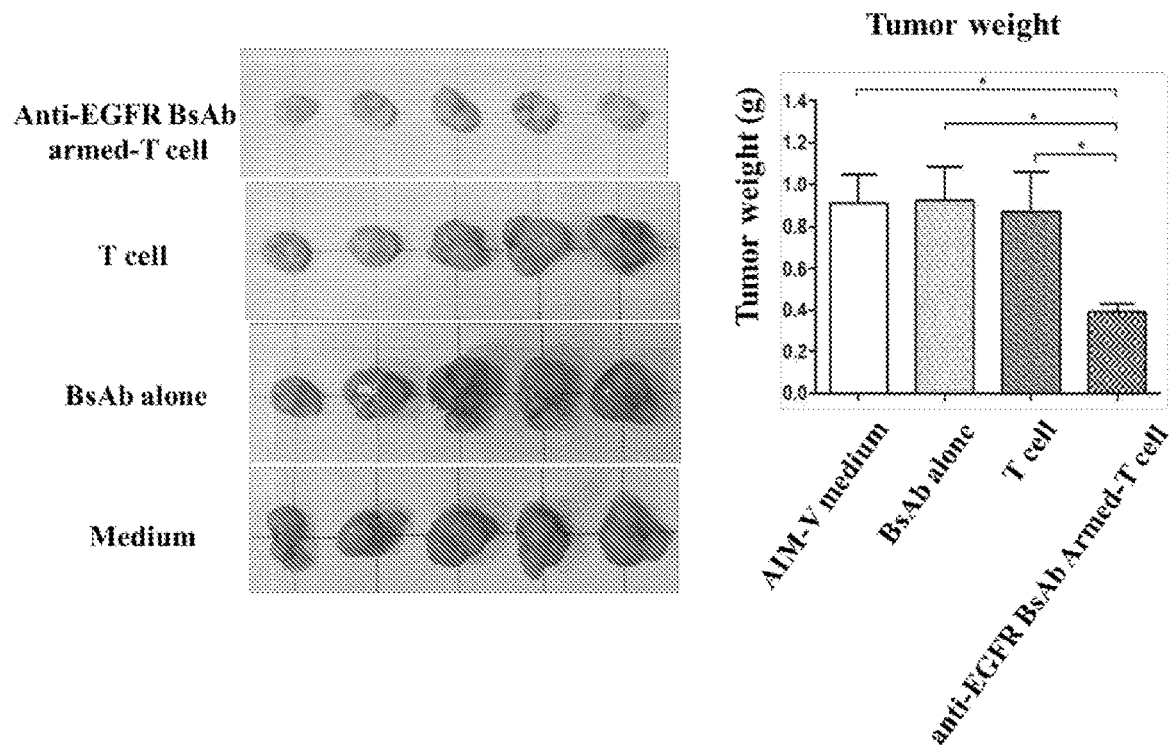
FIG. 27C illustrates the weight of a tumor treated by BsAb of Example 1.2, murine OKT3 T cells, or murine OKT3 T cells modified with anti-EGFR Fab/anti-CD3 scFv of Example 1.2 in accordance with one embodiment of the present disclosure.

In addition, the tumor size and its weight were suppressed significantly when treated with the modified murine OKT3 T cells (FIG. 27, panels A and C), while the body weight of the animals decreased only slightly along the 25-days treatment time course (FIG. 27, panel B).

Figure 28:
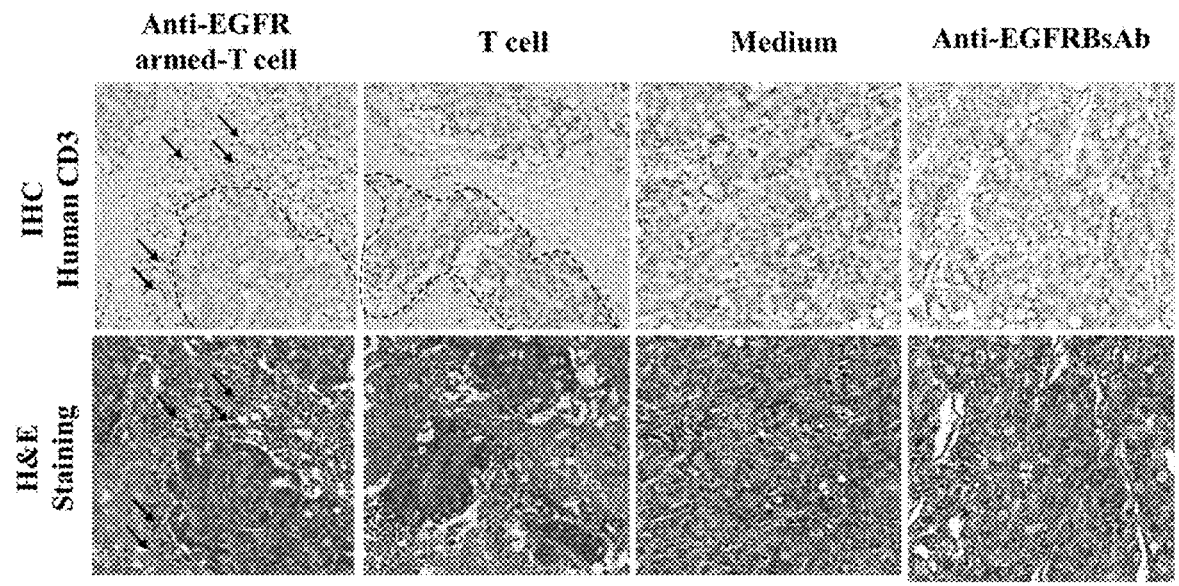
FIG. 28 are photographs of immunohistochemical (IHC) staining and H & E staining of a tumor treated by BsAb of Example 1.2, murine OKT3 T cells, or murine OKT3 T cells modified with anti-EGFR Fab/anti-CD3 scFv of Example 1.2 in accordance with one embodiment of the present disclosure.

The tumors harvested from the animals were further analyzed by immunohistochemical (IHC) staining and H&E staining, and results are depicted in FIG. 28. It was found that the modified murine OKT3 T cells were mainly concentrated in the neighboring area of the tumor.

Example 6 Comparable Studies on T Cells of Example 2 and the Modified Murine OKT3 Cells of Example 4

In this example, the differentiation and proliferation of T cells induced by the BsAbs of Example 1.2 (i.e., anti-PSMA Fab/anti-CD3 scFv and anti-PSMA scFv/anti-CD3 scFv) and murine OKT3 were compared. Results are depicted in FIGS. 29 to 32.

Figure 29B:
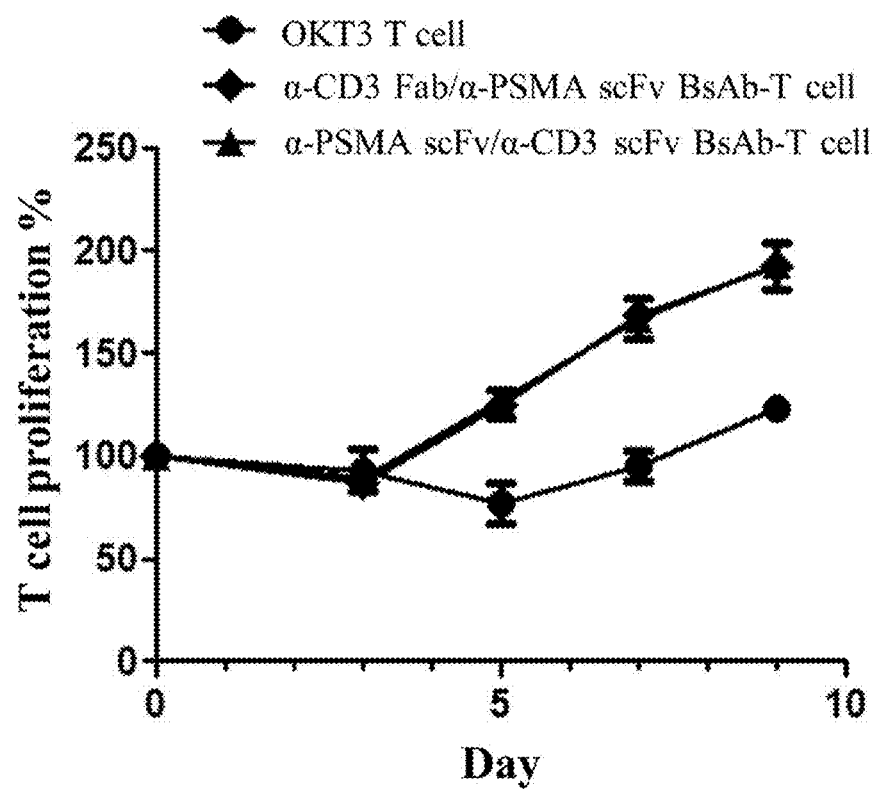
FIG. 29B illustrates the proliferation of T cells respectively differentiated by murine OKT3, and anti-CD3 Fab/anti-PSMA scFv, or anti-PSMA scFv/anti-CD3 scFv in accordance with one embodiment of the present disclosure.
Figure 29A:
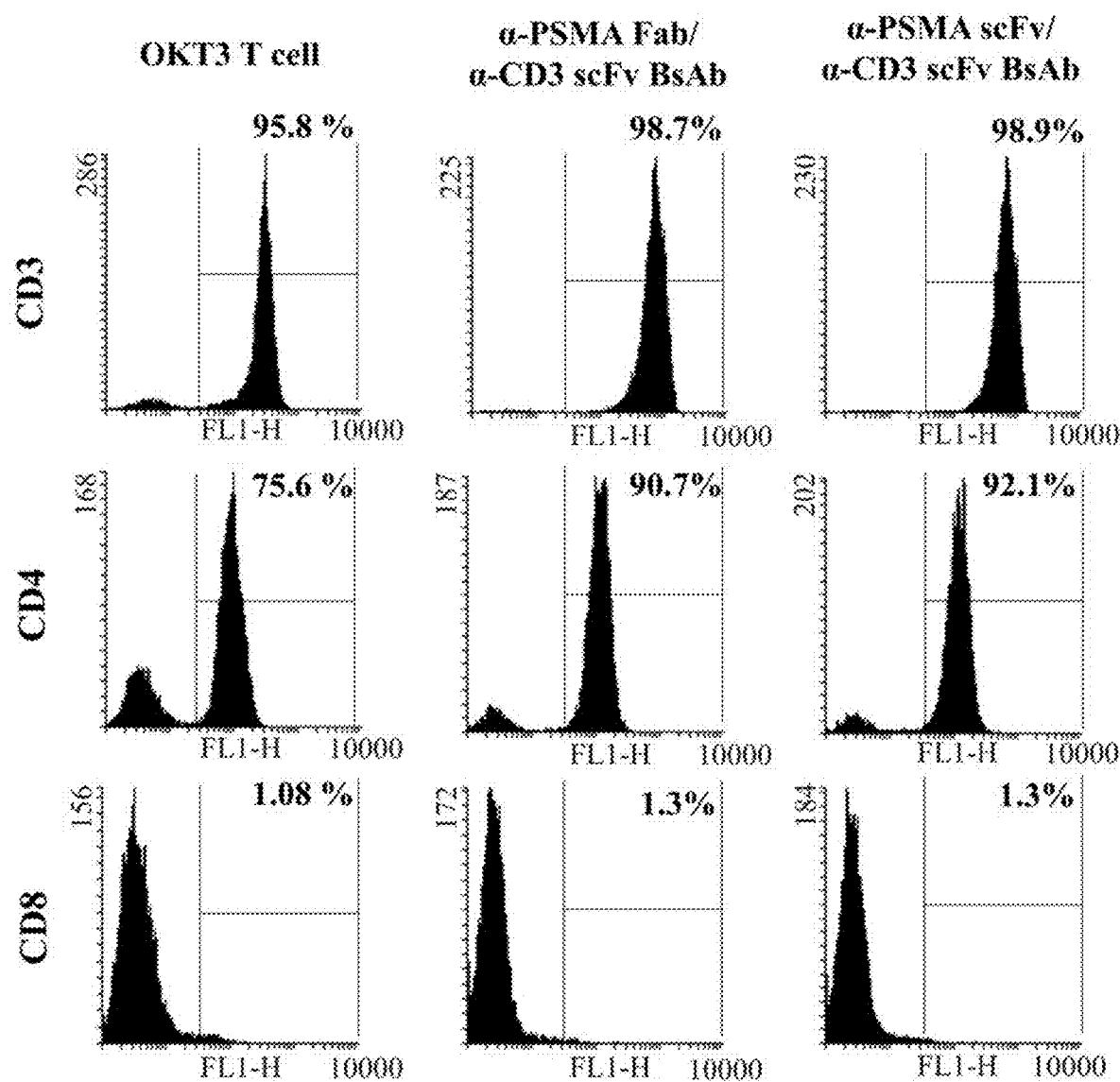
FIG. 29A illustrates flow cytometry analysis on the T cells differentiated by murine OKT3, and anti-PSMA Fab/anti-CD3 scFv, or anti-PSMA scFv/anti-CD3 scFv in accordance with one embodiment of the present disclosure.
Figure 30:
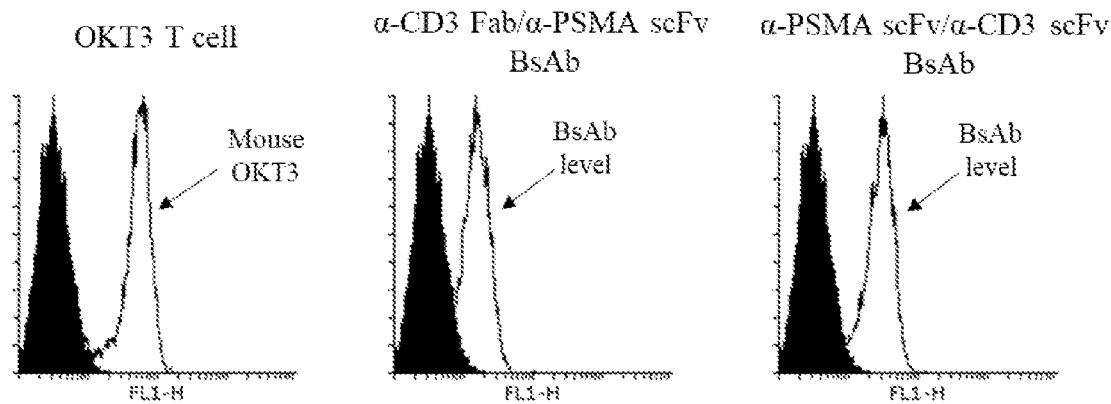
FIG. 30 illustrates the flow cytometry analysis on two types antibody fragments carried by OKT3 T cells or by T cells armed with anti-CD3 Fab/anti-PSMA scFv or anti-PSMA scFv/anti-CD3 scFv in accordance with one embodiment of the present disclosure.

As depicted in FIG. 29A, both the BsAbs of Example 1.2 (i.e., anti-PSMA Fab/anti-CD3 scFv and anti-PSMA scFv/anti-CD3 scFv) and murine OKT3 were capable of inducing differentiation of PBMCs into CD3+ cells, with over 95% of cells being CD3+ cells. As to the CD4+ cells, the BsAbs of Example 1.2 (i.e., anti-PSMA Fab/anti-CD3 scFv and anti-PSMA scFv/anti-CD3 scFv) were more effective than murine OKT3 in inducing the differentiation of PBMCs into CD4+ T cells, in which over 90% of PBMCs were differentiated into CD4+ cells after being treated with BsAbs of Example 1.2, while only about 75% PBMCs turned into CD4+ cells after murine OKT3 treatment. Further, the proliferation ratio of T cells induced by BsAbs of Example 1.2 was also higher than that by murine OKT3 T cells (FIG. 29B). Flow cytometry analysis further confirmed that similar to T cells induced by murine OKT3 Abs, which appeared on the surfaces of OKT3 T cells; the two types antibody fragments carried by each BsAbs of Example 1.2 also appeared on the surfaces of the T cells induced therefrom (FIG. 30).

Figure 31:
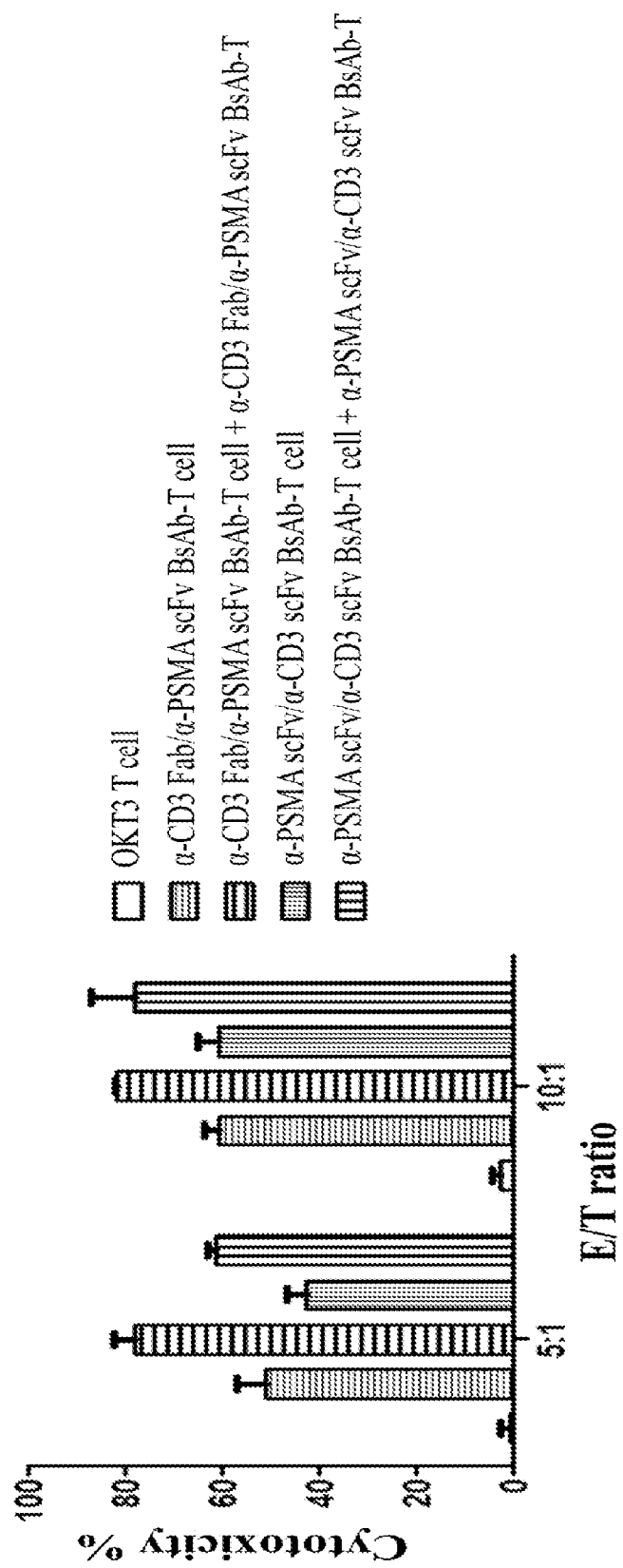
FIG. 31 illustrates the respective cytotoxicities of murine OKT3 T cells and T cells of example 2 on LNCaP cells in accordance with one embodiment of the present disclosure.

The comparative study on the cytotoxicity of murine OKT3 T cells and T cells of example 2 is provided in FIG. 31. As depicted, OKT3 T cells were incapable of killing PSMA+ cells (LNCaP cells), whereas the T cells of example 2 (or T cells induced by BsAbs of example 1) exhibited at least 50% cytotoxicity, and the cytotoxicity of the T cells would increase further if they were further modified with corresponding BsAbs of example 1.2. For example, the cytotoxicity of T cells differentiated by anti-CD3 Fab/anti-PSMA scFv was independently about 51.32% and 60.97% at the E/T ratio of 5:1 and 10:1; which increased to about 78.15% and 81.75% at the E/T ratio of 5:1 and 10:1, if they were further modified with anti-CD3 Fab/anti-PSMA scFv. Similar observation were found for T cells induced by anti-PSMA scFv/anti-CD3 scFv.

Example 7 One-Step Differentiation, Proliferation of Regulatory T Cells by BsAbs of Example 1.2

Figure 32:
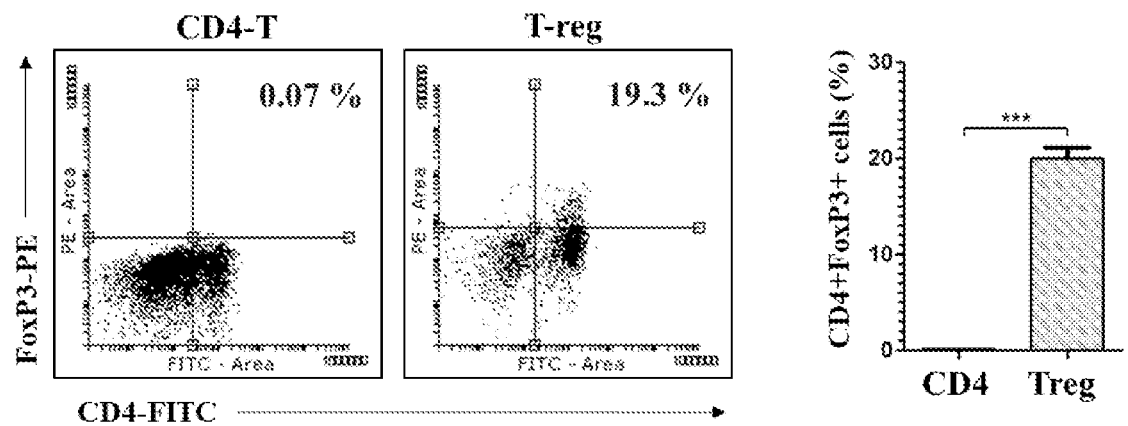
FIG. 32 illustrates the induction of $CD4^+FoxP3^+$ regulator T cells by anti-CD3 Fab/anti-PSMA scFv BsAb and anti-PSMA scFv/anti-CD3 scFv in accordance with one embodiment of the present disclosure.
Figure 32:
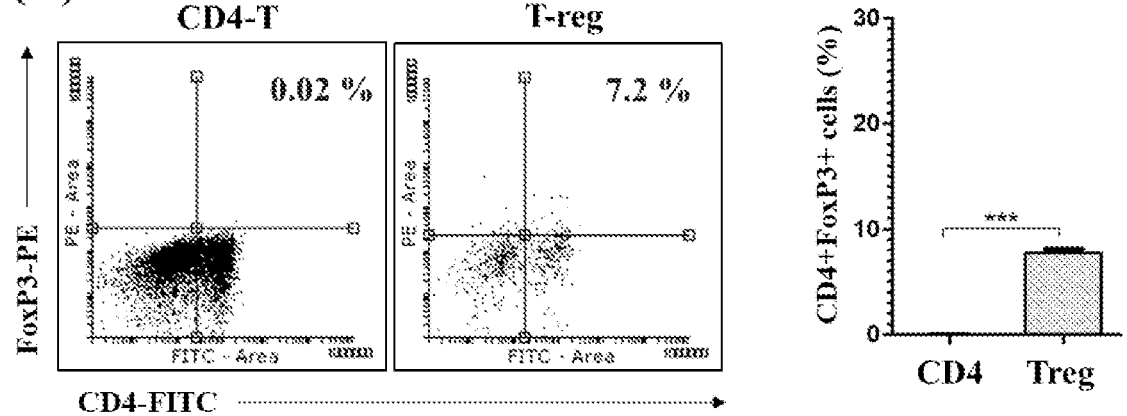

In this example, regulatory T cells were induced and formed by use of BsAbs of Example 1.2. Briefly, PBMCs from healthy human subjects were isolated and cultured with anti-CD3 Fab/anti-PSMA scFv or anti-PSMA scFv/anti-CD3 scFv of Example 1.2 for 7 days, in either case, the culture medium also contained IL2, TGF-β, and anti-CD28 antibodies. Then, differentiated T cells were harvested and subjected to flow cytometry analysis. Results are depicted in FIG. 32.

The data indicated that anti-CD3 Fab/anti-PSMA scFv BsAb and anti-PSMA scFv/anti-CD3 scFv could respectively induce the formation of about 19.3% (FIG. 32, panel A) and 7.2% (FIG. 32, panel B) of CD4+FoxP3+ regulator T cells.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of producing a tumor antigen-specific T cell from peripheral blood mononuclear cells (PBMCs) of a human subject, comprising:

culturing the PBMCs with a bi-specific antibody (BsAb) in a culture medium so as to produce the tumor antigen-specific T cell from the PBMCs, wherein the BsAb comprises a tumor antigen binding site and a CD3 binding site, wherein the tumor antigen binding site comprises an anti-tumor antigen scFv 100% identical to SEQ ID NO: 69; and the CD3 binding site comprises an anti-CD3 VL-Ck domain 100% identical to SEQ ID NO: 67, and an anti-CD3 VH-CH1 domain 100% identical to SEQ ID NO: 68.

2. The method of claim 1, wherein the culture medium comprises IL2 and does not comprise TGF-β, and the tumor antigen-specific T cell is a CD3+ and CD8+ T cell.

* * * * *

SEQUENCE LISTING

```
<160> NUMBER OF SEQ ID NOS: 143

<210> SEQ ID NO 1
<211> LENGTH: 63
<212> TYPE: DNA
<213> ORGANISM: Artificial Sequence
<220> FEATURE:
<223> OTHER INFORMATION: Synthetic

<400> SEQUENCE: 1
atggagacag acacactcct gctatgggta ctgctgctct gggttccagg ttccactggt      60
gac                                                                    63

<210> SEQ ID NO 2
<211> LENGTH: 645
<212> TYPE: DNA
<213> ORGANISM: Artificial Sequence
<220> FEATURE:
<223> OTHER INFORMATION: Synthetic
```

<400> SEQUENCE: 2

```
gacatcgtga tgacccagag ccccagcagc ctgagcgcca gcgtgggcga cagagtgacc    60
atcacctgca aggccagcca ggacgtgggc accgccgtgg actggtacca gcagaagccc   120
ggcaaggccc ccaagctgct gatctactgg gccagcacca gacacaccgg cgtgcccgac   180
agattcaccg gcagcggcag cggcaccgac ttcaccctga ccatcagcag cctgcagccc   240
gaggacttcg ccgactactt ctgccagcag tacaacagct accccctgac cttcggcggc   300
ggcaccaagc tggagatcaa gagaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540
ctgagcaaag cagactacga gaaacacaaa ctctacgcct gcgaagtcac ccatcagggc   600
ctgagctcgc ccgtcacaaa gagcttcaac aggggagagt gctga                   645
```

<210> SEQ ID NO 3
<211> LENGTH: 585
<212> TYPE: DNA
<213> ORGANISM: Artificial Sequence
<220> FEATURE:
<223> OTHER INFORMATION: Synthetic

<400> SEQUENCE: 3

```
gcccctctcc ctccccccccc cctaacgtta ctggccgaag ccgcttggaa taaggccggt    60
gtgcgtttgt ctatatgtta ttttccacca tattgccgtc ttttggcaat gtgagggccc   120
ggaaacctgg ccctgtcttc ttgacgagca ttcctagggg tctttcccct ctcgccaaag   180
gaatgcaagg tctgttgaat gtcgtgaagg aagcagttcc tctggaagct tcttgaagac   240
aaacaacgtc tgtagcgacc ctttgcaggc agcggaaccc cccacctggc gacaggtgcc   300
tctgcggcca aaagccacgt gtataagata cacctgcaaa ggcggcacaa ccccagtgcc   360
acgttgtgag ttggatagtt gtggaaagag tcaaatggct ctcctcaagc gtattcaaca   420
aggggctgaa ggatgcccag aaggtacccc attgtatggg atctgatctg ggcctcggt   480
gcacatgctt tacatgtgtt tagtcgaggt taaaaaaacg tctaggcccc ccgaaccacg   540
gggacgtggt tttcctttga aaaacacgat gataatatgg ccaca                   585
```

<210> SEQ ID NO 4
<211> LENGTH: 660
<212> TYPE: DNA
<213> ORGANISM: Artificial Sequence
<220> FEATURE:
<223> OTHER INFORMATION: Synthetic

<400> SEQUENCE: 4

```
gaggtgcagc tggtgcagag cggcgccgag gtgaagaagc ccggcgccag cgtgaagatc    60
agctgcaaga ccagcggcta caccttcacc gagtacacca tccactgggt gaagcaggcc   120
agcggcaagg gcctggagtg gatcggcaac atcaacccca caacggcgg caccacctac   180
aaccagaagt tcgaggacag agccaccctg accgtggaca gagcaccag caccgcctac   240
atggagctga gcagcctgag aagcgaggac accgccgtgt actactgcgc cgccggctgg   300
aacttcgact actggggcca gggcaccacc gtgaccgtga gcagcgcctc caccaagggc   360
ccatcggtct tccccctggc accctcctcc aagagcacct ctgggggcac agcggccctg   420
```

```
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660

<210> SEQ ID NO 5
<211> LENGTH: 774
<212> TYPE: DNA
<213> ORGANISM: Artificial Sequence
<220> FEATURE:
<223> OTHER INFORMATION: Synthetic

<400> SEQUENCE: 5
ggtggcggct caggtggagg cgacatcaag ctgcagcaga gcggcgccga gctggccaga     60
cccggcgcca gcgtgaagat gagctgcaag accagcggct acaccttcac cagatacacc    120
atgcactggg tgaagcagag acccggccag ggcctggagt ggatcggcta catcaacccc    180
agcagaggct acaccaacta caaccagaag ttcaaggaca aggccaccct gaccaccgac    240
aagagcagca gcaccgccta catgcagctg agcagcctga ccagcgagga cagcgccgtg    300
tactactgcg ccagatacta cgacgaccac tactgcctgg actactgggg ccagggcacc    360
accctgaccg tgagcagcgt ggagggcggc agcggcggca gcggcggcag cggcggcagc    420
ggcggcgtgg acgacatcca gctgacccag agccccgcca tcatgagcgc cagccccggc    480
gagaaggtga ccatgacctg cagagccagc agcagcgtga gctacatgaa ctggtaccag    540
cagaagagcg gcaccagccc caagagatgg atctacgaca ccagcaaggt ggccagcggc    600
gtgccctaca gattcagcgg cagcggcagc ggcaccagct acagcctgac catcagcagc    660
atggaggccg aggacgccgc cacctactac tgccagcagt ggagcagcaa ccccctgacc    720
ttcggcgctg gcaccaagct ggagctgaag agacaccacc accaccacca ctga          774

<210> SEQ ID NO 6
<211> LENGTH: 642
<212> TYPE: DNA
<213> ORGANISM: Artificial Sequence
<220> FEATURE:
<223> OTHER INFORMATION: Synthetic

<400> SEQUENCE: 6
gacatccagc tgacccagag ccccgccatc atgagcgcca gccccggcga aggtgacc       60 atgacctgca gagccagcag cagcgtgagc tacatgaact ggtaccagca gaagagcggc    120
accagcccca agagatggat ctacgacacc agcaaggtgg ccagcggcgt gccctacaga    180
ttcagcggca gcggcagcgg caccagctac agcctgacca tcagcagcat ggaggccgag    240
gacgccgcca cctactactg ccagcagtgg agcagcaacc ccctgacctt cggcgctggc    300
accaagctgg agctgaagag aactgtggct gcaccatctg tcttcatctt cccgccatct    360
gatgagcagt tgaaatctgg aactgcctct gttgtgtgcc tgctgaataa cttctatccc    420
agagaggcca agtacagtgg aaggtggat aacgccctcc aatcgggtaa ctcccaggag    480
agtgtcacag agcaggacag caaggacagc acctacagcc tcagcagcac cctgacgctg    540
agcaaagcag actacgagaa acacaaactc tacgcctgcg aagtcaccca tcagggcctg    600
agctcgcccg tcacaaagag cttcaacagg ggagagtgct ga                       642

<210> SEQ ID NO 7
<211> LENGTH: 651
```

<212> TYPE: DNA
<213> ORGANISM: Artificial Sequence
<220> FEATURE:
<223> OTHER INFORMATION: Synthetic

<400> SEQUENCE: 7

```
gacatcaagc tgcagcagag cggcgccgag ctggccagac ccggcgccag cgtgaagatg      60
agctgcaaga ccagcggcta caccttcacc agatacacca tgcactgggt gaagcagaga     120
cccggccagg gcctggagtg gatcggctac atcaaccccta gcagaggcta caccaactac    180
aaccagaagt tcaaggacaa ggccaccctg accaccgaca gagcagcag caccgcctac      240
atgcagctga gcagcctgac cagcgaggac agcgccgtgt actactgcgc cagatactac    300
gacgaccact actgcctgga ctactggggc cagggcacca ccctgaccgt gagcagcgcc   360
tccaccaaag gtccatcggt cttccccctg gcgccctgct ccaggagcac ctccgagagc   420
acagcggccc tgggctgcct ggtcaaggac tacttccccg aaccggtgac ggtgtcgtgg   480
aactcaggcg ctctgaccag cggcgtgcac accttcccag ctgtcctaca gtcctcagga   540
ctctactccc tcagcagcgt ggtgaccgtg ccctccagca cttcggcac ccagacctac    600
acctgcaacg tagatcacaa gcccagtaac accaaggtgg acaagacagt t            651
```

<210> SEQ ID NO 8
<211> LENGTH: 759
<212> TYPE: DNA
<213> ORGANISM: Artificial Sequence
<220> FEATURE:
<223> OTHER INFORMATION: Synthetic

<400> SEQUENCE: 8

```
ggcggcggca gcggcggcgg cgaggtgcag ctggtgcaga gcggcgccga ggtgaagaag      60
cccggcgcca gcgtgaagat cagctgcaag accagcggct acaccttcac cgagtacacc    120
atccactggg tgaagcaggc cagcggcaag ggcctggagt ggatcggcaa catcaacccc    180
aacaacggcg gcaccaccta caaccagaag ttcgaggaca gagccaccct gaccgtggac    240
aagagcacca gcaccgccta catggagctg agcagcctga aagcgagga caccgccgtg    300
tactactgcg ccgccggctg gaacttcgac tactggggcc agggcaccac cgtgaccgtg    360
agcagcgccg tggaggcgg ttcaggcgga ggtggctctg gcggtggcgg atcggacatc      420
gtgatgaccc agagcccag cagcctgagc gccagcgtgg gcgacagagt gaccatcacc      480
tgcaaggcca gcaggacgt gggcaccgcc gtggactggt accagcagaa gcccggcaag      540
gcccccaagc tgctgatcta ctgggccagc accagacaca ccggcgtgcc cgacagattc     600
accggcagcg gcagcggcac cgacttcacc ctgaccatca gcagcctgca gcccgaggac     660
ttcgccgact acttctgcca gcagtacaac agctaccccc tgaccttcgg cggcggcacc    720
aagctggaga tcaagagaca ccaccaccac caccactga                           759
```

<210> SEQ ID NO 9
<211> LENGTH: 717
<212> TYPE: DNA
<213> ORGANISM: Artificial Sequence
<220> FEATURE:
<223> OTHER INFORMATION: Synthetic

<400> SEQUENCE: 9

```
gacatcgtga tgacccagag ccccagcagc ctgagcgcca cgtgggcga cagagtgacc       60
atcacctgca aggccagcca ggacgtgggc accgccgtgg actggtacca gcagaagccc     120
```

| | |
|---|---:|
| ggcaaggccc ccaagctgct gatctactgg gccagcacca gacacaccgg cgtgcccgac | 180 |
| agattcaccg gcagcggcag cggcaccgac ttcacccctg accatcagca cctgcagccc | 240 |
| gaggacttcg ccgactactt ctgccagcag tacaacagct accccctgac cttcggcggc | 300 |
| ggcaccaagc tggagatcaa agaggtggaa ggcggttcag gcggaggtgg ctctggcggt | 360 |
| ggcggatcgg aggtgcagct ggtgcagagc ggcgccgagg tgaagaagcc cggcgccagc | 420 |
| gtgaagatca gctgcaagac cagcggctac accttcaccg agtacaccat ccactgggtg | 480 |
| aagcaggcca gcggcaaggg cctggagtgg attggcaaca tcaaccccaa caacggcggc | 540 |
| accacctaca accagaagtt cgaggacaga gccaccctga ccgtggacaa gagcaccagc | 600 |
| accgcctaca tggagctgag cagcctgaga agcgaggaca ccgccgtgta ctactgcgcc | 660 |
| gctggctgga acttcgacta ctggggccag ggcaccaccg tgaccgtgag cagcgcc | 717 |

```
<210> SEQ ID NO 10
<211> LENGTH: 672
<212> TYPE: DNA
<213> ORGANISM: Artificial Sequence
<220> FEATURE:
<223> OTHER INFORMATION: Synthetic

<400> SEQUENCE: 10
```

| | |
|---|---:|
| gacatccagc tgacccagag cccagcaatc atgtctgcca gcccaggaga gaaggtgacc | 60 |
| atgacatgcc gggccagcag cagcgtgagc tacatgaact ggtatcagcg gaagagcggc | 120 |
| acctccccta agagatggat ctacgacaca tctaaggtgg ccagcggcgt gccatatagg | 180 |
| ttctccggct ctggcagcgg cacctcctac tctctgacaa tcagctccat ggaggccgag | 240 |
| gatgccgcca cctactattg ccagcagtgg tctagcaatc ccctgacctt tggcgccggc | 300 |
| acaaagctgg agctgaagag gaccgtggca gcacctagcg tgttcatctt tccccttcc | 360 |
| gacgagcagc tgaagtccgg cacagcctct gtggtgtgcc tgctgaacaa tttctatcca | 420 |
| cgcgaggcca aggtgcagtg gaaggtggat aacgccctgc agtctggcaa tagccaggag | 480 |
| tccgtgaccg agcaggactc taaggatagc acatactccc tgtcctctac cctgacactg | 540 |
| agcaaggccg attacgagaa gcacaagctg tatgcatgcg aggtgaccca ccagggcctg | 600 |
| agctccccag tgacaaagtc ttttaaccgg ggcgagtgtg gcggcggctc ccaccaccac | 660 |
| caccaccact ga | 672 |

```
<210> SEQ ID NO 11
<211> LENGTH: 1350
<212> TYPE: DNA
<213> ORGANISM: Artificial Sequence
<220> FEATURE:
<223> OTHER INFORMATION: Synthetic

<400> SEQUENCE: 11
```

| | |
|---|---:|
| gacatcaagc tgcagcagag cggagcagag ctggccaggc ccggagcctc tgtgaagatg | 60 |
| agctgcaaga cctccggcta caccttcaca cggtatacaa tgcactgggt gaagtacaga | 120 |
| cctggccagg gcctggagtg gatcggctat atcaacccat cccgcggcta caccaactat | 180 |
| aatcagaagt ttaaggacaa ggccaccctg accacagata gagcctcctc tacagcctac | 240 |
| atgcagctga gctccctgac ctctgaggac agcgccgtgt actattgcgc ccggtactat | 300 |
| gacgatcact actgtctgga ttattggggc cagggcacca cactgaccgt gtctagcgcc | 360 |
| tctacaaagg gacctagcgt gttcccactg gcaccctcct ctaagtccac ctctggagga | 420 |
| acagccgccc tggatgcct ggtgaaggat tacttcccag agcccgtgac cgtgtcctgg | 480 |

```
aactctggcg ccctgaccag cggagtgcac acatttcctg ccgtgctgca gagctccggc    540
ctgtactccc tgtctagcgt ggtgacagtg ccatcctcta gcctgggcac ccagacatat    600
atctgcaacg tgaatcacaa gccaagcaat accaaggtcg acaagaaggt ggagcccaag    660
tcctgtgata gacccacaca tgccccccct tgtcctgcac cagagctgct gggaggacca    720
agcgtgttcc tgtttccacc caagcctaag acaccctga tgatctctcg acccccagag    780
gtgacatgcg tggtggtgga cgtgagccac gaggatcccg aggtgaagtt taactggtac    840
gtggatggcg tggaggtgca caatgccaag accaagccca gggaggagca gtacaattcc    900
acctatcgcg tggtgtctgt gctgacagtg ctgcaccagg actggctgaa cggcaaggag    960
tataagtgca aggtgtccaa taaggccctg cccgccccta tcgagaagac aatctctaag    1020
gcaaagggac agcctcggga gccacaggtg tacaccctgc ctccatccag agatgagctg    1080
accaagaacc aggtgtctct gacatgtctg gtgaagggct ctatccctc tgacatcgcc    1140 gtggagtggg agagcaatgg ccagcctgag aacaattacg ataccacacc ccctgtgctg    1200
gacagcgatg gctccttctt tctgtatagc gacctgacag tggataagtc cagatggcag    1260
cagggcaacg tgtttagctg ttccgtgatg cacgaggccc tgcacaatca ctacacccag    1320
aagtctctga gcctgtcccc cggcaagtaa                                    1350

<210> SEQ ID NO 12
<211> LENGTH: 684
<212> TYPE: DNA
<213> ORGANISM: Artificial Sequence
<220> FEATURE:
<223> OTHER INFORMATION: Synthetic

<400> SEQUENCE: 12
aggatcgtga tgacccagtc tcctagctcc ctgagcgcct ccgtgggcga ccgcgtgacc     60
atcacatgca aggccagcca ggatgtggga accgcagtgg actggtacca ggataagcca    120
ggcaaggccc ccaagctgct gatctattgg gcctccacca ggcacacagg agtgccagac    180
agattcaccg gctctggcag cggcacagac ttcaccctga caatctctag cctgcagccc    240
gaggacttcg ccgattactt ttgccagcag tacaacagct atcctctgac cttcggcggc    300
ggcacaaagc tggagatcaa gaggaccgtg gcagcaccat ccgtgttcat ctttcccct    360 tctgacgagc agctgaagtc tggcacagcc agcgtggtgt gctacctgaa caacttctac    420
cccagggagg ccaaggtgca gtggaaggtg ataacgccc tgcagtccgg caattctcag    480
gagagcgtga ccgagcagga ctccaaggat tctacataca gcctgtggtc caccctgaca    540
ctgtccaagg ccgactacga gaagcacaag ctgtatgcat gcgaggtgac ccaccagggc    600
ctgtcctctc ccgtgacaaa gagcttcaat aggggagagt gtggaggagg atcctaccct    660
tatgacgtgc cagattatgc ctaa                                          684

<210> SEQ ID NO 13
<211> LENGTH: 1338
<212> TYPE: DNA
<213> ORGANISM: Artificial Sequence
<220> FEATURE:
<223> OTHER INFORMATION: Synthetic

<400> SEQUENCE: 13
gaggtgcagc tggtgcagtc cggagcagag gtgaagaagc ctggagcctc tgtgaagatc     60
agctgcaaga cctccggcta caccttcaca gagtatacaa tccactgggt gaagaaggcc    120
```

```
agcggcaagg gcctggagtg gatcggcaac atcaatccaa acaatggcgg caccacatac      180
aaccaggagt tgaggaccg ggccaccctg acagtggata agtccacctc tacagcctat      240
atggagctga gctccctgag atccgaggac accgccgtgt actattgcgc cgccggctgg      300
aatttcgatt actggggcca gggcaccaca gtgaccgtgt ctagcgcctc tacaaaggga      360
ccaagcgtgt tccactggc accctcctct aagagcacct ccggaggaac agccgccctg      420
ggctgtctgg tgaaggacta tttcccagag cccgtgaccg tgtcctggaa ctctggcgcc      480
ctgacctccg gagtggcaac aggaccagcc gtgctgcaga gctccggcct gtacagcctg      540
tctagcgtgg tgaccgtgcc ctcctctagc ctgggcaccc agacatatat ctgcaacgtg      600
aatcacaagc caagcaatac aaaggtcgac aagaaggtgg agcccaagtc ctgtgataag      660
acccacacat gccccccttg tcctgcacca gagctgctgg gaggaccaag cgtgttcctg      720
tttccaccca gcctaagga caccctgatg atctctagga cccccgaggt gacatgcgtg      780
gtggtggacg tgagccacga ggatcctgag gtgaagttta actggtacgt ggatggcgtg      840
gaggtgcaca atgccaagac caagcccgg gaggagcagt acaactccac ctatagagtg      900
gtgtctgtgc tgacagtgct gcaccaggac tggctgaacg gcaaggagta taagtgcaag      960
gtgtccaata aggccctgcc cgcccctatc gagaagacca tctctaaggc caagggccag     1020
cctagggagc cacaggtgta cacactgcct ccatcccgca aggagctgac caagaaccag     1080
gtgtctctga catgtctggt gaagggcttc tatccttctg atatcgccgt gagtgggag       1140 agcaatggcc agccagagaa caattacaag accacacccc ctgtgctgaa gagcgacggc     1200
tccttctttc tgtatagcaa gctgaccgtg gataagtcca gatggcagca gggcaacgtg     1260
ttttcttgta gcgtgatgca cgaggccctg cacaatcact acacacagaa gtccctgtct     1320
ctgagccctg gcaagtaa                                                    1338
```

<210> SEQ ID NO 14
<211> LENGTH: 645
<212> TYPE: DNA
<213> ORGANISM: Artificial Sequence
<220> FEATURE:
<223> OTHER INFORMATION: Synthetic

<400> SEQUENCE: 14

```
gatattctgc tgacccagag cccggttatt ctgagcgtta gcccgggtga acgtgttagc        60
tttagctgtc gtgcaagcca gagcattggt accaatattc attggtatca gcagcgtacc       120
aatggtagcc cgcgtctgct gattaaatat gcaagcgaaa gcattagcgg tattccgagc       180
cgttttagcg gtagcggtag cggtaccgat tttaccctga gcattaatag cgttgaaagc       240
gaagatattg cagattatta ttgtcagcag aataataatt ggccgaccac ctttggtgca       300
ggtaccaaac tggaactgaa acgtactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag cacctgacg       540 ctgagcaaag cagactacga gaaacacaaa ctctacgcct cgaagtcac ccatcagggc       600 ctgagctcgc ccgtcacaaa gagcttcaac aggggagagt gctga                      645
```

<210> SEQ ID NO 15
<211> LENGTH: 672
<212> TYPE: DNA
<213> ORGANISM: Artificial Sequence

```
<220> FEATURE:
<223> OTHER INFORMATION: Synthetic

<400> SEQUENCE: 15
caggttcagc tgaaacagag cggtccgggt ctggttcagc cgagccagag cctgagcatt      60
acctgtaccg ttagcggttt tagcctgacc aattatggtg ttcattgggt tcgtcagagc     120
ccgggtaaag gtctggaatg gctgggtgtt atttggagcg gtggtaatac cgattataat     180
accccgttta ccagccgtct gagcattaat aaagataata gcaaaagcca ggttttttt     240
aaaatgaata gcctgcagag caatgatacc gcaatttatt attgtgcacg tgcactgacc     300
tattatgatt atgaatttgc atattggggt cagggtaccc tggttaccgt tagcgcagcc     360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aa                                                        672

<210> SEQ ID NO 16
<211> LENGTH: 768
<212> TYPE: DNA
<213> ORGANISM: Artificial Sequence
<220> FEATURE:
<223> OTHER INFORMATION: Synthetic

<400> SEQUENCE: 16
ggcggcggca gcggcggcgg ccaggttcag ctgaaacaga gcggtccggg tctggttcag      60
ccgagccaga gcctgagcat tacctgtacc gttagcggtt ttagcctgac caattatggt     120
gttcattggg ttcgtcagag cccgggtaaa ggtctggaat ggctgggtgt tatttggagc     180
ggtggtaata ccgattataa taccccgttt accagccgtc tgagcattaa taaagataat     240
agcaaaagcc aggtttttt taaaatgaat agcctgcaga gcaatgatac cgcaatttat     300
tattgtgcac gtgcactgac ctattatgat tatgaatttg catattgggg tcagggtacc     360
ctggttaccg ttagcgcagg cggcggcggc agcggcggcg gcggcagcgg cggcggcggc     420
agcgatattc tgctgaccca gagcccggtt attctgagcg ttagcccggg tgaacgtgtt     480
agctttagct gtcgtgcaag ccagagcatt ggtaccaata ttcattggta tcagcagcgt     540
accaatggta gcccgcgtct gctgattaaa tatgcaagcg aaagcattag cggtattccg     600
agccgtttta gcggtagcgg tagcggtacc gatttacccc tgagcattaa tagcgttgaa     660
agcgaagata ttgcagatta ttattgtcag cagaataata ttggccgac cacctttggt     720
gcaggtacca aactggaact gaaacgtcac caccaccacc accactga                 768

<210> SEQ ID NO 17
<211> LENGTH: 726
<212> TYPE: DNA
<213> ORGANISM: Artificial Sequence
<220> FEATURE:
<223> OTHER INFORMATION: Synthetic

<400> SEQUENCE: 17
gatattctgc tgacccagag cccggttatt ctgagcgtta gcccgggtga acgtgttagc      60
tttagctgtc gtgcaagcca gagcattggt accaatattc attggtatca gcagcgtacc     120
```

```
aatggtagcc cgcgtctgct gattaaatat gcaagcgaaa gcattagcgg tattccgagc      180
cgttttagcg gtagcggtag cggtaccgat tttacccctga gcattaatag cgttgaaagc     240
gaagatattg cagattatta ttgtcagcag aataataatt ggccgaccac ctttggtgca     300
ggtaccaaac tggaactgaa acgtggtgga ggcggttcag cgcgaggtgg ctctggcggt     360
ggcggatcgc aggttcagct gaaacagagc ggtccgggtc tggttcagcc gagccagagc     420
ctgagcatta cctgtaccgt tagcggtttt agcctgacca attatggtgt tcattgggtt     480
cgtcagagcc cgggtaaagg tctggaatgg ctgggtgtta tttggagcgg tggtaatacc     540
gattataata ccccgtttac cagccgtctg agcattaata aagataatag caaaagccag     600 gttttttttta aaatgaatag cctgcagagc aatgataccg caatttatta ttgtgcacgt     660
gcactgacct attatgatta tgaatttgca tattggggtc agggtaccct ggttaccgtt     720
agcgca                                                                726

<210> SEQ ID NO 18
<211> LENGTH: 765
<212> TYPE: DNA
<213> ORGANISM: Artificial Sequence
<220> FEATURE:
<223> OTHER INFORMATION: Synthetic

<400> SEQUENCE: 18
ggcggtggat cagacatcaa gctgcagcag agcggcgccg agctggccag acccggcgcc      60
agcgtgaaga tgagctgcaa gaccagcggc tacaccttca ccagatacac catgcactgg     120
gtgaagcaga cccgggcca gggcctggag tggatcggct acatcaaccc cagcagaggc     180
tacaccaact acaaccagaa gttcaaggac aaggccaccc tgaccaccga caagagcagc     240
agcaccgcct acatgcagct gagcagcctg accagcgagg acagcgccgt gtactactgc     300
gccagatact acgacgacca ctactgcctg gactactggg gccagggcac caccctgacc     360
gtgagcagcg tggagggcgg cagcggcggc agcggcggca gcggcggcag cggcggcgtg     420
gacgacatcc agctgaccca gagccccgcc atcatgagcg ccagccccgg cgagaaggtg     480
accatgacct gcagagccag cagcagcgtg agctacatga actggtacca gcagaagagc     540
ggcaccagcc ccaagagatg gatctacgac accagcaagg tggccagcgg cgtgccctac     600
agattcagcg gcagcggcag cggcaccagc tacagcctga ccatcagcag catggaggcc     660
gaggacgccg ccacctacta ctgccagcag tggagcagca acccctgac cttcggcgct     720 ggcaccaagc tggagctgaa agagacacca caccaccacc actga                    765

<210> SEQ ID NO 19
<211> LENGTH: 684
<212> TYPE: DNA
<213> ORGANISM: Artificial Sequence
<220> FEATURE:
<223> OTHER INFORMATION: Synthetic

<400> SEQUENCE: 19
aggattctgc tgacccagag cccggttatt ctgagcgtta gcccgggtga acgtgttagc      60
tttagctgtc gtgcaagcca gagcattggt accaatattc attggtatca ggatcgtacc     120
aatggtagcc cgcgtctgct gattaaatat gcaagcgaaa gcattagcgg tattccgagc     180
cgttttagcg gtagcggtag cggtaccgat tttacccctga gcattaatag cgttgaaagc     240
gaagatattg cagattatta ttgtcagcag aataataatt ggccgaccac ctttggtgca     300
ggtaccaaac tggaactgaa acgtaccgtg gcagcaccat ccgtgttcat ctttccccct     360
```

```
tctgacgagc agctgaagtc tggcacagcc agcgtggtgt gctacctgaa caacttctac    420
cccagggagg ccaaggtgca gtggaaggtg gataacgccc tgcagtccgg caattctcag    480
gagagcgtga ccgagcagga ctccaaggat tctacataca gcctgtggtc caccctgaca    540
ctgtccaagg ccgactacga aagcacaag ctgtatgcat gcgaggtgac ccaccagggc     600
```
(note: line 540→600 as printed)

```
ctgtccaagg ccgactacga aagcacaag  ctgtatgcat gcgaggtgac ccaccagggc    600
ctgtcctctc ccgtgacaaa gagcttcaat aggggagagt gtggaggagg atcctaccct    660
tatgacgtgc cagattatgc ctaa                                           684
```

<210> SEQ ID NO 20
<211> LENGTH: 1350
<212> TYPE: DNA
<213> ORGANISM: Artificial Sequence
<220> FEATURE:
<223> OTHER INFORMATION: Synthetic

<400> SEQUENCE: 20

```
caggttcagc tgaaacagag cggtccgggt ctggttcagc cgagccagag cctgagcatt     60
acctgtaccg ttagcggttt tagcctgacc aattatggtg ttcattgggt tcgtaagagc    120
ccgggtaaag gtctggaatg gctgggtgtt atttggagcg gtggtaatac cgattataat    180 accgagtttta ccagccgtct gagcattaat aaagataata gcaaaagcca ggttttttt    240 aaaatgaata gcctgcagag caatgatacc gcaatttatt attgtgcacg tgcactgacc    300
tattatgatt atgaatttgc atattggggt cagggtaccc tggttaccgt tagcgcagcc    360
tctacaaagg gaccaagcgt gtttccactg gcaccctcct ctaagagcac ctccggagga    420
acagccgccc tgggctgtct ggtgaaggac tatttcccag agcccgtgac cgtgtcctgg    480
aactctggcg ccctgacctc cggagtggca acaggaccag ccgtgctgca gagctccggc    540
ctgtacagcc tgtctagcgt ggtgaccgtg ccctcctcta gcctgggcac ccagacatat    600
atctgcaacg tgaatcacaa gccaagcaat acaaaggtcg acaagaaggt ggagcccaag    660
tcctgtgata agacccacac atgcccccct tgtcctgcac cagagctgct gggaggacca    720
agcgtgttcc tgtttccacc caagcctaag gacaccctga tgatctctag gacccccgag    780
gtgacatgcg tggtggtgga cgtgagccac gaggatcctg aggtgaagtt taactggtac    840
gtggatggcg tggaggtgca caatgccaag accaagcccc gggaggagca gtacaactcc    900
acctatagag tggtgtctgt gctgacagtg ctgcaccagg actggctgaa cggcaaggag    960
tataagtgca aggtgtccaa taaggccctg cccgcccta tcgagaagac catctctaag   1020
gccaagggcc agcctaggga gccacaggtg tacacactgc ctccatcccg caaggagctg   1080
accaagaacc aggtgtctct gacatgtctg gtgaagggct tctatccttc tgatatcgcc   1140
gtggagtggg agagcaatgg ccagccagag aacaattaca agaccacacc cctgtgctg    1200 aagagcgacg gctccttctt tctgtatagc aagctgaccg tggataagtc cagatggcag   1260
cagggcaacg tgttttcttg tagcgtgatg cacgaggccc tgcacaatca ctacacacag   1320
aagtccctgt ctctgagccc tggcaagtaa                                    1350
```

<210> SEQ ID NO 21
<211> LENGTH: 645
<212> TYPE: DNA
<213> ORGANISM: Artificial Sequence
<220> FEATURE:
<223> OTHER INFORMATION: Synthetic

<400> SEQUENCE: 21

```
gatatccaga tgacccagag ccctagctcc ctgagcgcct ccgtgggcga cagggtgacc      60
atcacatgta gggcatccca ggacgtgagc accgcagtgg cctggtatca gcagaagccc     120
ggcaaggccc ctaagctgct gatctactct gccagcttcc tgtatagcgg cgtgccttcc     180
agattttccg gatctggaag cggaaccgac ttcaccctga caatctctag cctgcagcca     240
gaggattttg ccacatacta ttgccagcag tacctgtatc acccagcaac cttcggacag     300
ggcacaaaag tggaaatcaa gcggactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa ctctacgcct gcgaagtcac ccatcagggc     600
ctgagctcgc ccgtcacaaa gagcttcaac aggggagagt gctga                    645
```

<210> SEQ ID NO 22
<211> LENGTH: 669
<212> TYPE: DNA
<213> ORGANISM: Artificial Sequence
<220> FEATURE:
<223> OTHER INFORMATION: Synthetic

<400> SEQUENCE: 22

```
gaggtgcagc tggtggaaag cggggggagga ctggtgcagc ctgggggggtc actgagactg     60
agttgcgccg cctccggctt cacctttttcc gactcttgga tccactgggt gaggcaggca    120
ccaggcaagg gcctggagtg ggtggcctgg atctctccct acggcggcag cacctactat    180
gccgactccg tgaagggccg gtttacaatc tctgccgata ccagcaagaa cacagcctat    240
ctgcagatga attctctgag agccgaggac accgccgtgt actattgcgc acggagacac    300
tggccaggag gattcgatta ctggggacag ggcacccctgg tgacagtgtc cgccgcctcc    360
accaagggcc catcggtctt ccccctggca cccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacccca gacctacatc    600
tgcaacgtga atcacaagcc cagcaacacc aaggtggaca gagagttga gcccaaatct    660
tgtgacaaa                                                            669
```

<210> SEQ ID NO 23
<211> LENGTH: 774
<212> TYPE: DNA
<213> ORGANISM: Artificial Sequence
<220> FEATURE:
<223> OTHER INFORMATION: Synthetic

<400> SEQUENCE: 23

```
gggggcggga gcggggggcgg cgaggtgcag ctggtggaaa gcgggggagg actggtgcag     60
cctgggggggt cactgagact gagttgcgcc gcctccggct tcacctttttc cgactcttgg    120
atccactggg tgaggcaggc accaggcaag ggcctggagt gggtggcctg gatctctccc    180
tacggcggca gcacctacta tgccgactcc gtgaagggcc ggtttacaat ctctgccgat    240
accagcaaga acacagccta tctgcagatg aattctctga gagccgagga caccgccgtg    300
```

| | |
|---|---|
| tactattgcg cacggagaca ctggccagga ggattcgatt actggggaca gggcaccctg | 360 |
| gtgacagtgt ccgccgtgga gggaggatcc ggaggatctg gaggaagcgg cggctccggc | 420 |
| ggcgtggacg atatccagat gacccagagc cctagctccc tgagcgcctc cgtgggcgac | 480 |
| agggtgacca tcacatgtag ggcatcccag gacgtgagca ccgcagtggc ctggtatcag | 540 |
| cagaagcccg gcaaggcccc taagctgctg atctactctg ccagcttcct gtatagcggc | 600 |
| gtgccttcca gattttccgg atctggaagc ggaaccgact tcaccctgac aatctctagc | 660 |
| ctgcagccag aggattttgc cacatactat tgccagcagt acctgtatca cccagcaacc | 720 |
| ttcggacagg gcacaaaagt ggaaatcaag cggcatcatc atcatcacca ttaa | 774 |

```
<210> SEQ ID NO 24
<211> LENGTH: 723
<212> TYPE: DNA
<213> ORGANISM: Artificial Sequence
<220> FEATURE:
<223> OTHER INFORMATION: Synthetic

<400> SEQUENCE: 24
```

| | |
|---|---|
| gatatccaga tgacccagag ccctagctcc ctgagcgcct ccgtgggcga cagggtgacc | 60 |
| atcacatgta gggcatccca ggacgtgagc accgcagtgg cctggtatca gcagaagccc | 120 |
| ggcaaggccc ctaagctgct gatctactct gccagcttcc tgtatagcgg cgtgccttcc | 180 |
| agattttccg gatctggaag cggaaccgac ttcaccctga caatctctag cctgcagcca | 240 |
| gaggattttg ccacatacta ttgccagcag tacctgtatc acccagcaac cttcggacag | 300 |
| ggcacaaaag tggaaatcaa gcggggtgga ggcggttcag gcggaggtgg ctctggcggt | 360 |
| ggcggatcgg aggtgcagct ggtggaaagc gggggaggac tggtgcagcc tggggggtca | 420 |
| ctgagactga gttgcgccgc ctccggcttc accttttccg actcttggat ccactgggtg | 480 |
| aggcaggcac caggcaaggg cctggagtgg gtggcctgga tctctcccta cggcggcagc | 540 |
| acctactatg ccgactccgt gaagggccgg tttacaatct ctgccgatac cagcaagaac | 600 |
| acagcctatc tgcagatgaa ttctctgaga gccgaggaca ccgccgtgta ctattgcgca | 660 |
| cggagacact ggccaggagg attcgattac tggggacagg gcaccctggt gacagtgtcc | 720 |
| gcc | 723 |

```
<210> SEQ ID NO 25
<211> LENGTH: 684
<212> TYPE: DNA
<213> ORGANISM: Artificial Sequence
<220> FEATURE:
<223> OTHER INFORMATION: Synthetic

<400> SEQUENCE: 25
```

| | |
|---|---|
| aggatccaga tgacccagag ccctagctcc ctgagcgcct ccgtgggcga cagggtgacc | 60 |
| atcacatgta gggcatccca ggacgtgagc accgcagtgg cctggtatca ggataagccc | 120 |
| ggcaaggccc ctaagctgct gatctactct gccagcttcc tgtatagcgg cgtgccttcc | 180 |
| agattttccg gatctggaag cggaaccgac ttcaccctga caatctctag cctgcagcca | 240 |
| gaggattttg ccacatacta ttgccagcag tacctgtatc acccagcaac cttcggacag | 300 |
| ggcacaaaag tggaaatcaa gcggaccgtg gcagcaccat ccgtgttcat ctttccccct | 360 |
| tctgacgagc agctgaagtc tggcacagcc agcgtggtgt gctacctgaa caacttctac | 420 |
| cccagggagg ccaaggtgca gtggaaggtg gataacgccc tgcagtccgg caattctcag | 480 |
| gagagcgtga ccgagcagga ctccaaggat tctacataca gcctgtggtc caccctgaca | 540 |

```
ctgtccaagg ccgactacga gaagcacaag ctgtatgcat gcgaggtgac ccaccagggc    600
ctgtcctctc ccgtgacaaa gagcttcaat aggggagagt gtggaggagg atcctaccct    660
tatgacgtgc cagattatgc ctaa                                           684
```

<210> SEQ ID NO 26
<211> LENGTH: 1347
<212> TYPE: DNA
<213> ORGANISM: Artificial Sequence
<220> FEATURE:
<223> OTHER INFORMATION: Synthetic

<400> SEQUENCE: 26

```
gaggtgcagc tggtggaaag cggggagga ctggtgcagc ctgggggtc actgagactg       60 agttgcgccg cctccggctt cacctttcc gactcttgga tccactgggt gaggaaggca    120
ccaggcaagg gcctggagtg ggtggcctgg atctctccct acggcggcag cacctactat    180
gccgactccg tgaagggcga gtttacaatc tctgccgata ccagcaagaa cacagcctat    240
ctgcagatga attctctgag agccgaggac accgccgtgt actattgcgc acggagacac    300
tggccaggag gattcgatta ctggggacag ggcaccctgg tgacagtgtc cgccgcctct    360
acaaagggac caagcgtgtt tccactggca ccctcctcta gagcacctc cggaggaaca    420 gccgccctgg gctgtctggt gaaggactat ttcccagagc ccgtgaccgt gtcctggaac    480
tctggcgccc tgacctccgg agtggcaaca ggaccagccg tgctgcagag ctccggcctg    540
tacagcctgt ctagcgtggt gaccgtgccc tcctctagcc tgggcaccca gacatatatc    600
tgcaacgtga atcacaagcc aagcaataca aaggtcgaca agaaggtgga gcccaagtcc    660
tgtgataaga cccacacatg ccccccttgt cctgcaccag agctgctggg aggaccaagc    720
gtgttcctgt ttccacccaa gcctaaggac accctgatga tctctaggac ccccgaggtg    780
acatgcgtgg tggtggacgt gagccacgag gatcctgagg tgaagtttaa ctggtacgtg    840
gatggcgtgg aggtgcacaa tgccaagacc aagccccggg aggagcagta caactccacc    900
tatagagtgg tgtctgtgct gacagtgctg caccaggact ggctgaacgg caaggagtat    960
aagtgcaagg tgtccaataa ggccctgccc gcccctatcg agaagaccat ctctaaggcc   1020
aagggccagc ctagggagcc acaggtgtac acactgcctc catcccgcaa ggagctgacc   1080
aagaaccagg tgtctctgac atgtctggtg aagggcttct atccttctga tatcgccgtg   1140
gagtgggaga gcaatggcca gccagagaac aattacaaga ccacacccc tgtgctgaag   1200 agcgacggct ccttctttct gtatagcaag ctgaccgtgg ataagtccag atggcagcag   1260
ggcaacgtgt tttcttgtag cgtgatgcac gaggccctgc acaatcacta cacacagaag   1320
tccctgtctc tgagccctgg caagtaa                                        1347
```

<210> SEQ ID NO 27
<211> LENGTH: 645
<212> TYPE: DNA
<213> ORGANISM: Artificial Sequence
<220> FEATURE:
<223> OTHER INFORMATION: Synthetic

<400> SEQUENCE: 27

```
gacatccaga tgacccagag ccccagcagc ctgagcgcca gcgtgggcga cagagtgacc     60
atcacctgca gagccagcca ggacgtgaac accgccgtgg cctggtacca gcagaagccc    120
ggcaaggccc ccaagctgct gatctacagc gccagcttcc tgtacagcgg cgtgcccagc    180
```

| agattcagcg gcagcagaag cggcaccgac ttcaccctga ccatcagcag cctgcagccc | 240 |
| gaggacttcg ccacctacta ctgccagcag cactacacca cccccccac cttcggccag | 300 |
| ggcaccaagg tggagatcaa gagaactgtg ctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gctga | 645 |

<210> SEQ ID NO 28
<211> LENGTH: 675
<212> TYPE: DNA
<213> ORGANISM: Artificial Sequence
<220> FEATURE:
<223> OTHER INFORMATION: Synthetic

<400> SEQUENCE: 28

| gaggtgcagc tggtggagag cggcggcggc ctggtgcagc ccggcggcag cctgagactg | 60 |
| agctgcgccg ccagcggctt caacatcaag gacacctaca tccactgggt gagacaggcc | 120 |
| cccggcaagg gcctggagtg ggtggccaga atctacccca ccaacggcta caccagatac | 180 |
| gccgacagcg tgaagggcag attcaccatc agcgccgaca ccagcaagaa caccgcctac | 240 |
| ctgcagatga acagcctgag agccgaggac accgccgtgt actactgcag cagatggggc | 300 |
| ggcgacggct tctacgccat ggactactgg ggccagggca ccctggtgac cgtgagcagc | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttgagccc | 660 |
| aaatcttgtg acaaa | 675 |

<210> SEQ ID NO 29
<211> LENGTH: 759
<212> TYPE: DNA
<213> ORGANISM: Artificial Sequence
<220> FEATURE:
<223> OTHER INFORMATION: Synthetic

<400> SEQUENCE: 29

| ggcggcggca gcggcggcgg cgaggtgcag ctggtgcaga gcggcgccga ggtgaagaag | 60 |
| cccggcgcca gcgtgaagat cagctgcaag accagcggct acaccttcac cgagtacacc | 120 |
| atccactggg tgaagcaggc cagcggcaag ggcctggagt ggatcggcaa catcaacccc | 180 |
| aacaacggcg gcaccaccta caaccagaag ttcgaggaca gagccaccct gaccgtggac | 240 |
| aagagcacca gcaccgccta catggagctg agcagcctga aagcgagga caccgccgtg | 300 |
| tactactgcg ccgccggctg gaacttcgac tactggggcc agggcaccac cgtgaccgtg | 360 |
| agcagcgccg gtgaggcgg ttcaggcgga ggtggctctg gcggtggcgg atcggacatc | 420 |
| gtgatgaccc agagcccag cagcctgagc gccagcgtgg gcgacagagt gaccatcacc | 480 |
| tgcaaggcca gccaggacgt gggcaccgcc gtggactggt accagcagaa gcccggcaag | 540 |
| gcccccaagc tgctgatcta ctgggccagc accagacaca ccggcgtgcc cgacagattc | 600 |

```
accggcagcg gcagcggcac cgacttcacc ctgaccatca gcagcctgca gcccgaggac    660
ttcgccgact acttctgcca gcagtacaac agctaccccc tgaccttcgg cggcggcacc    720
aagctggaga tcaagagaca ccaccaccac caccactga                           759
```

<210> SEQ ID NO 30
<211> LENGTH: 729
<212> TYPE: DNA
<213> ORGANISM: Artificial Sequence
<220> FEATURE:
<223> OTHER INFORMATION: Synthetic

<400> SEQUENCE: 30

```
gacatccaga tgacccagag ccccagcagc ctgagcgcca gcgtgggcga cagagtgacc     60
atcacctgca gagccagcca ggacgtgaac accgccgtgg cctggtacca gcagaagccc    120
ggcaaggccc ccaagctgct gatctacagc gccagcttcc tgtacagcgg cgtgcccagc    180
agattcagcg gcagcagaag cggcaccgac ttcaccctga ccatcagcag cctgcagccc    240
gaggacttcg ccacctacta ctgccagcag cactacacca ccccccccac cttcggccag    300
ggcaccaagg tggagatcaa gagaggtgga ggcggttcag gcggaggtgg ctctggcggt    360
ggcggatcgg aggtgcagct ggtggagagc ggcggcggcc tggtgcagcc cggcggcagc    420
ctgagactga gctgcgccgc cagcggcttc aacatcaagg acacctacat ccactgggtg    480
agacaggccc ccggcaaggg cctggagtgg gtggccagaa tctaccccac caacggctac    540
accagatacg ccgacagcgt gaagggcaga ttcaccatca gcgccgacac cagcaagaac    600
accgcctacc tgcagatgaa cagcctgaga gccgaggaca ccgccgtgta ctactgcagc    660
agatggggcg gcgacggctt ctacgccatg gactactggg gccagggcac cctggtgacc    720
gtgagcagc                                                            729
```

<210> SEQ ID NO 31
<211> LENGTH: 684
<212> TYPE: DNA
<213> ORGANISM: Artificial Sequence
<220> FEATURE:
<223> OTHER INFORMATION: Synthetic

<400> SEQUENCE: 31

```
aggatccaga tgacccagag ccccagcagc ctgagcgcca gcgtgggcga cagagtgacc     60
atcacctgca gagccagcca ggacgtgaac accgccgtgg cctggtacca ggataagccc    120
ggcaaggccc ccaagctgct gatctacagc gccagcttcc tgtacagcgg cgtgcccagc    180
agattcagcg gcagcagaag cggcaccgac ttcaccctga ccatcagcag cctgcagccc    240
gaggacttcg ccacctacta ctgccagcag cactacacca ccccccccac cttcggccag    300
ggcaccaagg tggagatcaa gagaaccgtg gcagcaccat ccgtgttcat ctttcccct     360 tctgacgagc agctgaagtc tggcacagcc agcgtggtgt gctacctgaa caacttctac    420
cccagggagg ccaaggtgca gtggaaggtg ataacgccc tgcagtccgg caattctcag     480
gagagcgtga ccgagcagga ctccaaggat tctacataca gcctgtggtc caccctgaca    540
ctgtccaagg ccgactacga aagcacaag ctgtatgcat gcgaggtgac ccaccagggc     600
ctgtcctctc ccgtgacaaa gagcttcaat aggggagagt gtgaggagg atcctaccct     660 tatgacgtgc cagattatgc ctaa                                           684
```

<210> SEQ ID NO 32

```
<211> LENGTH: 1353
<212> TYPE: DNA
<213> ORGANISM: Artificial Sequence
<220> FEATURE:
<223> OTHER INFORMATION: Synthetic

<400> SEQUENCE: 32
gaggtgcagc tggtggagag cggcggcggc ctggtgcagc ccggcggcag cctgagactg      60
agctgcgccg ccagcggctt caacatcaag gacacctaca tccactgggt gagaaaggcc     120
cccggcaagg gcctggagtg ggtggccaga atctacccca ccaacggcta caccagatac     180
gccgacagcg tgaagggcag gttcaccatc agcgccgaca ccagcaagaa caccgcctac     240
ctgcagatga acagcctgag agccgaggac accgccgtgt actactgcag cagatggggc     300
ggcgacggct tctacgccat ggactactgg ggccagggca ccctggtgac cgtgagcagc     360
gcctctacaa agggaccaag cgtgtttcca ctggcaccct cctctaagag cacctccgga     420
ggaacagccg ccctgggctg tctggtgaag gactatttcc cagagcccgt gaccgtgtcc     480
tggaactctg gcgccctgac ctccggagtg cacaccttca ccagccgtgct gcagagctcc     540
ggcctgtaca gcctgtctag cgtggtgacc gtgccctcct ctagcctggg cacccagaca     600
tatatctgca acgtgaatca caagccaagc aatacaaagg tcgacaagaa ggtggagccc     660
aagtcctgtg ataagaccca cacatgcccc ccttgtcctg caccagagct gctgggagga     720
ccaagcgtgt tcctgtttcc acccaagcct aaggacaccc tgatgatctc taggacccca     780
gaggtgacat gcgtggtggt ggacgtgagc cacgaggatc ctgaggtgaa gtttaactgg     840
tacgtggatg gcgtggaggt gcacaatgcc aagaccaagc ccgggaggga gcagtacaac     900
tccacctata gagtggtgtc tgtgctgaca gtgctgcacc aggactggct gaacggcaag     960
gagtataagt gcaaggtgtc caataaggcc ctgcccgccc ctatcgagaa gaccatctct    1020
aaggccaagg gccagcctag ggagccacag gtgtacacac tgcctccatc ccgcaaggag    1080
ctgaccaaga accaggtgtc tctgacatgt ctggtgaagg gcttctatcc ttctgatatc    1140
gccgtggagt gggagagcaa tggccagcca gagaacaatt acaagaccac ccccctgtg    1200
ctgaagagcg acggctcctt ctttctgtat agcaagctga ccgtggataa gtccagatgg    1260
cagcagggca acgtgttttc ttgtagcgtg atgcacgagg ccctgcacaa tcactacaca    1320
cagaagtccc tgtctctgag ccctggcaag taa                                 1353

<210> SEQ ID NO 33
<211> LENGTH: 660
<212> TYPE: DNA
<213> ORGANISM: Artificial Sequence
<220> FEATURE:
<223> OTHER INFORMATION: Synthetic

<400> SEQUENCE: 33
gacattgtga tgacccagtc ccctgacagc ctggctgtga gcctgggaga gagggccacc      60
atcaactgca agagcagcca gagcctgctg tacagcagaa accagaaaaa ctacctggcc     120
tggtaccagc agaaacccgg ccagcctccc aagctgctga tcttctgggc cagcaccaga     180
gagagcggcg tgcctgacag attcagcggc tccggcttcg gcaccgactt cacccctgacc   240
atcagcagcc tccaggccga ggatgtcgcc gtgtattact gccagcagta cttctcctat     300
cccctcacct tcggccaagg caccaaggtg gagatcaaga ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
```

| | |
|---|---|
| tcgggtaact cccaggagag tgtcacagag caggacagca aggacagcac ctacagcctc | 540 |
| agcagcaccc tgacgctgag caaagcagac tacgagaaac acaaactcta cgcctgcgaa | 600 |
| gtcacccatc agggcctgag ctcgcccgtc acaaagagct tcaacagggg agagtgctga | 660 |

<210> SEQ ID NO 34
<211> LENGTH: 687
<212> TYPE: DNA
<213> ORGANISM: Artificial Sequence
<220> FEATURE:
<223> OTHER INFORMATION: Synthetic

<400> SEQUENCE: 34

| | |
|---|---|
| caagtgcagc tggtgcagtc cggcgctgag gtgaagaagc ccggagcctc cgtgaaggtg | 60 |
| tcctgcaaga cctccaggta caccttcaca gagtacacca tccactgggt gagacaggct | 120 |
| cccggccaga ggctggagtg gattggcggc attaacccca caacggcat ccccaactac | 180 |
| aaccagaagt tcaagggcag ggtgaccatc acagttgata catccgccag cacagcctat | 240 |
| atggaactga gctccctgag gagcgaggac acagccgtgt actactgcgc caggaggagg | 300 |
| attgcctacg gctatgatga gggccatgcc atggactact ggggacaggg caccctggtg | 360 |
| acagtctcca gcgcctccac caagggccca tcggtcttcc ccctggcacc ctcctccaag | 420 |
| agcacctctg ggggcacagc ggccctgggc tgcctggtca aggactactt ccccgaaccg | 480 |
| gtgacggtgt cgtggaactc aggcgccctg accagcggcg tgcacacctt cccggctgtc | 540 |
| ctacagtcct caggactcta ctccctcagc agcgtggtga ccgtgccctc agcagcttg | 600 |
| ggcacccaga cctacatctg caacgtgaat cacaagccca gcaacaccaa ggtggacaag | 660 |
| agagttgagc ccaaatcttg tgacaaa | 687 |

<210> SEQ ID NO 35
<211> LENGTH: 807
<212> TYPE: DNA
<213> ORGANISM: Artificial Sequence
<220> FEATURE:
<223> OTHER INFORMATION: Synthetic

<400> SEQUENCE: 35

| | |
|---|---|
| ggcggcggca gcggcggcgg ccaagtgcag ctggtgcagt ccggcgctga ggtgaagaag | 60 |
| cccggagcct ccgtgaaggt gtcctgcaag acctccaggt acaccttcac agagtacacc | 120 |
| atccactggg tgagacaggc tcccggccag aggctggagt ggattggcgg cattaacccc | 180 |
| aacaacggca tccccaacta caaccagaag ttcaagggca gggtgaccat cacagttgat | 240 |
| acatccgcca gcacagccta tatggaactg agctccctga ggagcgagga cacagccgtg | 300 |
| tactactgcg ccaggaggag gattgcctac ggctatgatg agggccatgc catggactac | 360 |
| tggggacagg gcaccctggt gacagtctcc agcggcagca ccagcggatc cggaaagcct | 420 |
| ggcagcggag agggaagcac caagggcgac attgtgatga cccagtcccc tgacagcctg | 480 |
| gctgtgagcc tgggagagag ggccaccatc aactgcaaga gcagccagag cctgctgtac | 540 |
| agcagaaacc agaaaaacta cctggcctgg taccagcaga aacccggcca gcctcccaag | 600 |
| ctgctgatct tctgggccag caccagagag agcggcgtgc ctgacagatt cagcggctcc | 660 |
| ggcttcggca ccgacttcac cctgaccatc agcagcctcc aggccgagga tgtcgccgtg | 720 |
| tattactgcc agcagtactt ctcctatccc ctcaccttcg gccaaggcac caaggtggag | 780 |
| atcaagcacc accaccacca ccactga | 807 |

<210> SEQ ID NO 36
<211> LENGTH: 756
<212> TYPE: DNA
<213> ORGANISM: Artificial Sequence
<220> FEATURE:
<223> OTHER INFORMATION: Synthetic

<400> SEQUENCE: 36

| | | | | | | |
|---|---|---|---|---|---|---|
| gacattgtga | tgacccagtc | ccctgacagc | ctggctgtga | gcctgggaga | gagggccacc | 60 |
| atcaactgca | agagcagcca | gagcctgctg | tacagcagaa | accagaaaaa | ctacctggcc | 120 |
| tggtaccagc | agaaacccgg | ccagcctccc | aagctgctga | tcttctgggc | cagcaccaga | 180 |
| gagagcggcg | tgcctgacag | attcagcggc | tccggcttcg | gcaccgactt | caccctgacc | 240 |
| atcagcagcc | tccaggccga | ggatgtcgcc | gtgtattact | gccagcagta | cttctcctat | 300 |
| cccctcacct | tcggccaagg | caccaaggtg | gagatcaagg | gtggaggcgg | ttcaggcgga | 360 |
| ggtggctctg | gcggtggcgg | atcgcaagtg | cagctggtgc | agtccggcgc | tgaggtgaag | 420 |
| aagcccggag | cctccgtgaa | ggtgtcctgc | aagacctcca | ggtacacctt | cacagagtac | 480 |
| accatccact | gggtgagaca | ggctcccggc | cagaggctgg | agtggattgg | cggcattaac | 540 |
| cccaacaacg | gcatcccaa | ctacaaccag | aagttcaagg | gcagggtgac | catcacagtt | 600 |
| gatacatccg | ccagcacagc | ctatatggaa | ctgagctccc | tgaggagcga | ggacacagcc | 660 |
| gtgtactact | gcgccaggag | gaggattgcc | tacggctatg | atgagggcca | tgccatggac | 720 |
| tactggggac | agggcaccct | ggtgacagtc | tccagc | | | 756 |

<210> SEQ ID NO 37
<211> LENGTH: 699
<212> TYPE: DNA
<213> ORGANISM: Artificial Sequence
<220> FEATURE:
<223> OTHER INFORMATION: Synthetic

<400> SEQUENCE: 37

| | | | | | | |
|---|---|---|---|---|---|---|
| aggattgtga | tgacccagtc | ccctgacagc | ctggctgtga | gcctgggaga | gagggccacc | 60 |
| atcaactgca | agagcagcca | gagcctgctg | tacagcagaa | accagaaaaa | ctacctggcc | 120 |
| tggtaccagg | ataaacccgg | ccagcctccc | aagctgctga | tcttctgggc | cagcaccaga | 180 |
| gagagcggcg | tgcctgacag | attcagcggc | tccggcttcg | gcaccgactt | caccctgacc | 240 |
| atcagcagcc | tccaggccga | ggatgtcgcc | gtgtattact | gccagcagta | cttctcctat | 300 |
| cccctcacct | tcggccaagg | caccaaggtg | gagatcaaga | ccgtggcagc | accatccgtg | 360 |
| ttcatctttc | ccccttctga | cgagcagctg | aagtctggca | cagccagcgt | ggtgtgctac | 420 |
| ctgaacaact | tctaccccag | ggaggccaag | gtgcagtgga | aggtggataa | cgccctgcag | 480 |
| tccggcaatt | ctcaggagag | cgtgaccgag | caggactcca | aggattctac | atacagcctg | 540 |
| tggtccaccc | tgacactgtc | caaggccgac | tacgagaagc | acaagctgta | tgcatgcgag | 600 |
| gtgacccacc | agggcctgtc | ctctcccgtg | acaaagagct | tcaataggg | agagtgtgga | 660 |
| ggaggatcct | acccttatga | cgtgccagat | tatgcctaa | | | 699 |

<210> SEQ ID NO 38
<211> LENGTH: 1365
<212> TYPE: DNA
<213> ORGANISM: Artificial Sequence
<220> FEATURE:
<223> OTHER INFORMATION: Synthetic

<400> SEQUENCE: 38

```
caagtgcagc tggtgcagtc cggcgctgag gtgaagaagc ccggagcctc cgtgaaggtg      60
tcctgcaaga cctccaggta caccttcaca gagtacacca tccactgggt gagaaaggct     120
cccggccaga ggctggagtg gattggcggc attaaccccca acaacggcat ccccaactac    180
```
*Note: line 3 as printed: `cccggccaga ggctggagtg gattggcggc attaaccccca acaacggcat ccccaactac`*

```
caagtgcagc tggtgcagtc cggcgctgag gtgaagaagc ccggagcctc cgtgaaggtg      60
tcctgcaaga cctccaggta caccttcaca gagtacacca tccactgggt gagaaaggct     120
cccggccaga ggctggagtg gattggcggc attaacccca acaacggcat ccccaactac     180
aaccagaggt tcaagggcag ggtgaccatc acagttgata catccgccag cacagcctat     240
atggaactga gctccctgag gagcgaggac acagccgtgt actactgcgc caggaggagg     300
attgcctacg gctatgatga gggccatgcc atggactact ggggacaggg caccctggtg     360
acagtctcca gcgcctctac aaagggacca agcgtgtttc cactggcacc ctcctctaag     420
agcacctccg gaggaacagc cgccctgggc tgtctggtga aggactattt cccagagccc     480
gtgaccgtgt cctggaactc tggcgccctg acctccggag tggcaacagg accagccgtg     540
ctgcagagct ccgcctgtat cagcctgtct agcgtggtga ccgtgccctc ctctagcctg     600
ggcacccaga catatatctg caacgtgaat cacaagccaa gcaatacaaa ggtcgacaag     660
aaggtggagc ccaagtcctg tgataagacc cacacatgcc ccccttgtcc tgcaccagag     720
ctgctgggag gaccaagcgt gttcctgttt ccacccaagc ctaaggacac cctgatgatc     780
tctaggaccc ccgaggtgac atgcgtggtg gtggacgtga gccacgagga tcctgaggtg     840
aagtttaact ggtacgtgga tggcgtggag gtgcacaatg ccaagaccaa gccccgggag     900
gagcagtaca actccaccta tagagtggtg tctgtgctga cagtgctgca ccaggactgg     960
ctgaacggca aggagtataa gtgcaaggtg tccaataagg ccctgcccgc ccctatcgag    1020
aagaccatct ctaaggccaa gggccagcct agggagccac aggtgtacac actgcctcca    1080
tcccgcaagg agctgaccaa gaaccaggtg tctctgacat gtctggtgaa gggcttctat    1140
ccttctgata tcgccgtgga gtgggagagc aatggccagc cagagaacaa ttacaagacc    1200
acacccccctg tgctgaagag cgacggctcc ttctttctgt atagcaagct gaccgtggat    1260
aagtccagat ggcagcaggg caacgtgttt tcttgtagcg tgatgcacga ggccctgcac    1320
aatcactaca cacagaagtc cctgtctctg agccctggca agtaa                    1365
```

<210> SEQ ID NO 39
<211> LENGTH: 657
<212> TYPE: DNA
<213> ORGANISM: Artificial Sequence
<220> FEATURE:
<223> OTHER INFORMATION: Synthetic

<400> SEQUENCE: 39

```
gatattcaga tgacccagag cccttcaagc ctgtccgcca gcgtcgggga tagagtgacc      60
attacttgcc ggagcaccaa gtccctgctg cactccaacg gcatcacata cctgtattgg     120
taccagcaga agcccggcaa ggcccctaag ctgctgatct atcagatgtc caatctggcc     180
tctggcgtgc caagcagatt cagctcctct ggcagcggca ccgactttac cctgacaatc     240
agctccctgc agcccgagga tttcgccaca tactattgcg cccagaacct ggagatccct     300
aggaccttg ccagggcac aaaggtggag ctgaagactg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
```

```
agcaccctga cgctgagcaa agcagactac gagaaacaca aactctacgc ctgcgaagtc    600
acccatcagg gcctgagctc gcccgtcaca aagagcttca cagggga gtgctga         657

<210> SEQ ID NO 40
<211> LENGTH: 663
<212> TYPE: DNA
<213> ORGANISM: Artificial Sequence
<220> FEATURE:
<223> OTHER INFORMATION: Synthetic

<400> SEQUENCE: 40
gaggtgcagc tggtgcagtc cggacctggc ctggtgcagc caggaggctc cgtgaggatc     60
tcttgtgccg ccagcggcta taccttcaca aactacggca tgaattgggt gaagcaggca    120
cctggcaagg gcctggagtg gatgggctgg atcaacacct atacaggcga gtccacctac    180
gccgactctt ttaagggcag attcaccttt tctctggata catccgcctc tgccgcctac    240
ctgcagatca atagcctgcg ggccgaggac acagccgtgt actattgtgc cagattcgcc    300
atcaaagggg actactgggg acagggcaca ctgctgaccg tctcaagcgc ctccaccaag    360
ggcccatcgg tcttcccct ggcaccctcc tccaagagca cctctggggg cacagcggcc     420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagagag ttgagcccaa atcttgtgac    660
aaa                                                                   663

<210> SEQ ID NO 41
<211> LENGTH: 771
<212> TYPE: DNA
<213> ORGANISM: Artificial Sequence
<220> FEATURE:
<223> OTHER INFORMATION: Synthetic

<400> SEQUENCE: 41
ggcggcggca gcggcggcgg cgaggtgcag ctggtgcagt ccggacctgg cctggtgcag     60
ccaggaggct ccgtgaggat ctcttgtgcc gccagcggct ataccttcac aaactacggc    120
atgaattggg tgaagcaggc acctggcaag ggcctggagt ggatgggctg gatcaacacc    180
tatacaggcg agtccaccta cgccgactct tttaagggca gattcacctt ttctctggat    240
acatccgcct ctgccgccta cctgcagatc aatagcctgc gggccgagga cacagccgtg    300
tactattgtg ccagattcgc catcaaaggg gactactggg gacagggcac actgctgacc    360
gtctcaagcg gtgaggcgg ttcaggcgga ggtggctctg gcggtggcgg atcggatatt    420
cagatgaccc agagcccttc aagcctgtcc gccagcgtcg gggatagagt gaccattact    480
tgccggagca ccaagtccct gctgcactcc aacggcatca catacctgta ttggtaccag    540
cagaagcccg gcaaggcccc taagctgctg atctatcaga tgtccaatct ggcctctggc    600
gtgccaagca gattcagctc ctctggcagc ggcaccgact ttaccctgac aatcagctcc    660
ctgcagcccg aggatttcgc cacatactat tgcgcccaga acctggagat ccctaggacc    720
tttggccagg gcacaaaggt ggagctgaag caccaccacc accaccactg a              771

<210> SEQ ID NO 42
<211> LENGTH: 762
<212> TYPE: DNA
```

<213> ORGANISM: Artificial Sequence
<220> FEATURE:
<223> OTHER INFORMATION: Synthetic

<400> SEQUENCE: 42

```
gatattcaga tgacccagag cccttcaagc ctgtccgcca gcgtcgggga tagagtgacc      60
attacttgcc ggagcaccaa gtccctgctg cactccaacg gcatcacata cctgtattgg    120
taccagcaga agcccggcaa ggcccctaag ctgctgatct atcagatgtc caatctggcc    180
tctggcgtgc caagcagatt cagctcctct ggcagcggca ccgactttac cctgacaatc    240
agctccctgc agcccgagga tttcgccaca tactattgcg cccagaacct ggagatccct    300
aggacctttg gcagggcac aaaggtggag ctgaagcgcg ccaccccctc tcacaacagc    360
caccaggtgc aagcgccgg aggaccaacc gccaattccg gcatctctgg aagcgaggtg    420
cagctggtgc agtccggacc tggcctggtg cagccaggag gctccgtgag gatctcttgt    480
gccgccagcg gctatacctt cacaaactac ggcatgaatt gggtgaagca ggcacctggc    540
aagggcctgg agtggatggg ctggatcaac acctatacag gcgagtccac ctacgccgac    600
tcttttaagg gcagattcac ctttttctctg gatacatccg cctctgccgc ctacctgcag    660
atcaatagcc tgcgggccga ggacacagcc gtgtactatt gtgccagatt cgccatcaaa    720
ggggactact ggggacaggg cacactgctg accgtctcaa gc                      762
```

<210> SEQ ID NO 43
<211> LENGTH: 696
<212> TYPE: DNA
<213> ORGANISM: Artificial Sequence
<220> FEATURE:
<223> OTHER INFORMATION: Synthetic

<400> SEQUENCE: 43

```
aggattcaga tgacccagag cccttcaagc ctgtccgcca gcgtcgggga tagagtgacc      60
attacttgcc ggagcaccaa gtccctgctg cactccaacg gcatcacata cctgtattgg    120
taccaggata agcccggcaa ggcccctaag ctgctgatct atcagatgtc caatctggcc    180
tctggcgtgc caagcagatt cagctcctct ggcagcggca ccgactttac cctgacaatc    240
agctccctgc agcccgagga tttcgccaca tactattgcg cccagaacct ggagatccct    300
aggacctttg gccagggcac aaaggtggag ctgaagaccg tggcagcacc atccgtgttc    360
atctttcccc cttctgacga gcagctgaag tctggcacag ccagcgtggt gtgctacctg    420
aacaacttct accccaggga ggccaaggtg cagtggaagg tggataacgc cctgcagtcc    480
ggcaattctc aggagagcgt gaccgagcag gactccaagg attctacata cagcctgtgg    540
tccacccctga cactgtccaa ggccgactac gagaagcaca gctgtatgc atgcgaggtg    600
acccaccagg gcctgtcctc tcccgtgaca aagagcttca taggggaga gtgtggagga    660
ggatcctacc cttatgacgt gccagattat gcctaa                              696
```

<210> SEQ ID NO 44
<211> LENGTH: 1341
<212> TYPE: DNA
<213> ORGANISM: Artificial Sequence
<220> FEATURE:
<223> OTHER INFORMATION: Synthetic

<400> SEQUENCE: 44

```
gaggtgcagc tggtgcagtc cggacctggc ctggtgcagc caggaggctc cgtgaggatc      60
tcttgtgccg ccagcggcta ccttcaca aactacggca tgaattgggt gaagaaggca    120
```

```
cctggcaagg gcctggagtg gatgggctgg atcaacacct atacaggcga gtccacctac        180
gccgactctt ttaagggcga gttcaccttt tctctggata catccgcctc tgccgcctac        240
ctgcagatca atagcctgcg ggccgaggac acagccgtgt actattgtgc cagattcgcc        300
atcaaagggg actactgggg acagggcaca ctgctgaccg tctcaagcgc tctacaaag         360 ggaccaagcg tgtttccact ggcaccctcc tctaagagca cctccggagg aacagccgcc        420
ctgggctgtc tggtgaagga ctatttccca gagcccgtga ccgtgtcctg gaactctggc        480
gccctgacct ccggagtggc aacaggacca gccgtgctgc agagctccgg cctgtacagc        540
ctgtctagcg tggtgaccgt gccctcctct agcctgggca cccagacata tatctgcaac        600
gtgaatcaca agccaagcaa tacaaaggtc gacaagaagg tggagcccaa gtcctgtgat        660
aagacccaca catgcccccc ttgtcctgca ccagagctgc tgggaggacc aagcgtgttc        720
ctgtttccac ccaagcctaa ggacaccctg atgatctcta ggacccccga ggtgacatgc        780
gtggtggtgg acgtgagcca cgaggatcct gaggtgaagt taactggta cgtggatggc        840 gtggaggtgc acaatgccaa gaccaagccc cgggaggagc agtacaactc cacctataga        900
gtggtgtctg tgctgacagt gctgcaccag gactggctga acggcaagga gtataagtgc        960
aaggtgtcca ataaggccct gcccgcccct atcgagaaga ccatctctaa ggccaagggc       1020
cagcctaggg agccacaggt gtacacactg cctccatccc gcaaggagct gaccaagaac       1080
caggtgtctc tgacatgtct ggtgaagggc ttctatcctt ctgatatcgc cgtggagtgg       1140
gagagcaatg gccagccaga gaacaattac aagaccacac ccctgtgct gaagagcgac        1200 ggctccttct ttctgtatag caagctgacc gtggataagt ccagatggca gcagggcaac       1260 gtgtttct ct tgtagcgtgat gcacgaggcc ctgcacaatc actacacaca gaagtccctg       1320
tctctgagcc ctggcaagta a                                                  1341

<210> SEQ ID NO 45
<211> LENGTH: 642
<212> TYPE: DNA
<213> ORGANISM: Artificial Sequence
<220> FEATURE:
<223> OTHER INFORMATION: Synthetic

<400> SEQUENCE: 45
gagctgcaga tgacccagtc ccctagctct ttaagcgctt ccgtgggcga cagagtgacc         60
atcacatgtc gtacctccca gagcatcagc tcctatttaa actggtacca gcagaagccc        120
ggacagcccc ccaagctgct gatctactgg gcttccactc tgaaagcgg cgtgcccgat         180 cgttttccg gcagcggcag cggcaccgac tttactttaa ccatctcctc tttacagccc         240
gaggatagcg ccacctacta ctgccagcag agctacgaca tccctacac attcggccaa         300 ggtaccaagc tggaaatcaa aactgtggct gcaccatctg tcttcatctt cccgccatct        360
gatgagcagt tgaaatctgg aactgcctct gttgtgtgcc tgctgaataa cttctatccc       420
agagaggcca agtacagtgg aaggtggat aacgccctcc aatcgggtaa ctcccaggag        480
agtgtcacag agcaggacag caaggacagc acctacagcc tcagcagcac cctgacgctg       540
agcaaagcag actacgagaa acacaaactc tacgcctgcg aagtcaccca tcagggcctg      600
agctcgcccg tcacaaagag cttcaacagg ggagagtgct ga                            642

<210> SEQ ID NO 46
<211> LENGTH: 696
<212> TYPE: DNA
```

<213> ORGANISM: Artificial Sequence
<220> FEATURE:
<223> OTHER INFORMATION: Synthetic

<400> SEQUENCE: 46

```
gaagtgcagc tgctggagag cggaggcgga gtggtgcaac ccggtcgttc tttaaggctg      60
agctgcgctg ccagcggctt caccttcagc agctatggca tgcactgggt gagacaagct     120
cccggaaaag gtttagagtg ggtggccgtg atctcctacg acggcagcaa caagtactac     180
gccgacagcg tgaagggtcg tttcaccatc tctcgtgaca actccaagaa cactttatac     240
ctccagatga actctttaag ggccgaggac accgccgtgt actactgtgc caaggacatg     300
ggctggggca gcggatggag gccctactac tactacggca tggacgtgtg gggccaaggt     360
acaaccgtga ccgtgtccag cgcctccacc aagggcccat cggtcttccc cctggcaccc     420
tcctccaaga gcacctctgg gggcacagcg gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacccagac ctacatctgc aacgtgaatc acaagcccag caacaccaag     660
gtggacaaga gagttgagcc caaatcttgt gacaaa                                696
```

<210> SEQ ID NO 47
<211> LENGTH: 789
<212> TYPE: DNA
<213> ORGANISM: Artificial Sequence
<220> FEATURE:
<223> OTHER INFORMATION: Synthetic

<400> SEQUENCE: 47

```
ggcggcggca gcggcggcgg cgaagtgcag ctgctggaga gcggaggcgg agtggtgcaa      60
cccggtcgtt ctttaaggct gagctgcgct gccagcggct tcaccttcag cagctatggc     120
atgcactggg tgagacaagc tcccggaaaa ggtttagagt gggtggccgt gatctcctac     180
gacggcagca acaagtacta cgccgacagc gtgaagggtc gtttcaccat ctctcgtgac     240
aactccaaga acactttata cctccagatg aactctttaa gggccgagga caccgccgtg     300
tactactgtg ccaaggacat gggctggggc agcggatgga ggccctacta ctactacggc     360
atggacgtgt ggggccaagg tacaaccgtg accgtgtcca gcggtggagg cggttcaggc     420
ggaggtggct ctggcggtgg cggatcggag ctgcagatga cccagtcccc tagctcttta     480
agcgcttccg tgggcgacag agtgaccatc acatgtcgta cctcccagag catcagctcc     540
tatttaaact ggtaccagca gaagcccgga cagcccccca agctgctgat ctactgggct     600
tccactcgtg aaagcggcgt gcccgatcgt ttttccggca gcggcagcgg caccgacttt     660
actttaacca tctcctcttt acagcccgag gatagcgcca cctactactg ccagcagagc     720
tacgacatcc cctacacatt cggccaaggt accaagctgg aaatcaaaca ccaccaccac     780
caccactga                                                              789
```

<210> SEQ ID NO 48
<211> LENGTH: 747
<212> TYPE: DNA
<213> ORGANISM: Artificial Sequence
<220> FEATURE:
<223> OTHER INFORMATION: Synthetic

<400> SEQUENCE: 48

| gagctgcaga | tgacccagtc | ccctagctct | ttaagcgctt | ccgtgggcga | cagagtgacc | 60 |
| atcacatgtc | gtacctccca | gagcatcagc | tcctatttaa | actggtacca | gcagaagccc | 120 |
| ggacagcccc | ccaagctgct | gatctactgg | gcttccactc | gtgaaagcgg | cgtgcccgat | 180 |
| cgttttccg | gcagcggcag | cggcaccgac | tttactttaa | ccatctcctc | tttacagccc | 240 |
| gaggatagcg | ccacctacta | ctgccagcag | agctacgaca | tcccctacac | attcggccaa | 300 |
| ggtaccaagc | tggaaatcaa | aggcggcggc | ggcagcggcg | gcggcggctc | cggcggagga | 360 |
| ggctccgaag | tgcagctgct | ggagagcgga | ggcggagtgg | tgcaacccgg | tcgttcttta | 420 |
| aggctgagct | gcgctgccag | cggcttcacc | ttcagcagct | atggcatgca | ctgggtgaga | 480 |
| caagctcccg | gaaaaggttt | agagtggtg | gccgtgatct | cctacgacgg | cagcaacaag | 540 |
| tactacgccg | acagcgtgaa | gggtcgtttc | accatctctc | gtgacaactc | caagaacact | 600 |
| ttatacctcc | agatgaactc | tttaagggcc | gaggacaccg | ccgtgtacta | ctgtgccaag | 660 |
| gacatgggct | ggggcagcgg | atggaggccc | tactactact | acggcatgga | cgtgtggggc | 720 |
| caaggtacaa | ccgtgaccgt | gtccagc | | | | 747 |

<210> SEQ ID NO 49
<211> LENGTH: 681
<212> TYPE: DNA
<213> ORGANISM: Artificial Sequence
<220> FEATURE:
<223> OTHER INFORMATION: Synthetic

<400> SEQUENCE: 49

| aggctgcaga | tgacccagtc | ccctagctct | ttaagcgctt | ccgtgggcga | cagagtgacc | 60 |
| atcacatgtc | gtacctccca | gagcatcagc | tcctatttaa | actggtacca | ggataagccc | 120 |
| ggacagcccc | ccaagctgct | gatctactgg | gcttccactc | gtgaaagcgg | cgtgcccgat | 180 |
| cgttttccg | gcagcggcag | cggcaccgac | tttactttaa | ccatctcctc | tttacagccc | 240 |
| gaggatagcg | ccacctacta | ctgccagcag | agctacgaca | tcccctacac | attcggccaa | 300 |
| ggtaccaagc | tggaaatcaa | aaccgtggca | gcaccatccg | tgttcatctt | tccccttct | 360 |
| gacgagcagc | tgaagtctgg | cacagccagc | gtggtgtgct | acctgaacaa | cttctacccc | 420 |
| agggaggcca | aggtgcagtg | gaaggtggat | aacgccctgc | agtccggcaa | ttctcaggag | 480 |
| agcgtgaccg | agcaggactc | caaggattct | acatacagcc | tgtggtccac | cctgacactg | 540 |
| tccaaggcca | actacgagaa | gcacaagctg | tatgcatgcg | aggtgaccca | ccagggcctg | 600 |
| tcctctcccg | tgacaaagag | cttcaatagg | ggagagtgtg | aggaggatc | ctacccttat | 660 |
| gacgtgccag | attatgccta | a | | | | 681 |

<210> SEQ ID NO 50
<211> LENGTH: 1374
<212> TYPE: DNA
<213> ORGANISM: Artificial Sequence
<220> FEATURE:
<223> OTHER INFORMATION: Synthetic

<400> SEQUENCE: 50

| gaagtgcagc | tgctggagag | cggaggcgga | gtggtgcaac | ccggtcgttc | tttaaggctg | 60 |
| agctgcgctg | ccagcggctt | caccttcagc | agctatggca | tgcactgggt | gagaaaggct | 120 |
| cccggaaaag | gtttagagtg | ggtggccgtg | atctcctacg | acggcagcaa | caagtactac | 180 |

```
gccgacagcg tgaagggtga gttcaccatc tctcgtgaca actccaagaa cactttatac    240
ctccagatga actctttaag ggccgaggac accgccgtgt actactgtgc caaggacatg    300
ggctggggca gcggatggag gccctactac tactacggca tggacgtgtg gggccaaggt    360
acaaccgtga ccgtgtccag cgcctctaca aagggaccaa gcgtgtttcc actggcaccc    420
tcctctaaga gcacctccgg aggaacagcc gccctgggct gtctggtgaa ggactatttc    480
ccagagcccg tgaccgtgtc ctggaactct ggcgccctga cctccggagt ggcaacagga    540
ccagccgtgc tgcagagctc cggcctgtac agcctgtcta gcgtggtgac cgtgccctcc    600
tctagcctgg gcacccagac atatatctgc aacgtgaatc acaagccaag caatacaaag    660
gtcgacaaga aggtggagcc caagtcctgt gataagaccc acacatgccc cccttgtcct    720
gcaccagagc tgctgggagg accaagcgtg ttcctgtttc cacccaagcc taaggacacc    780
ctgatgatct ctaggacccc cgaggtgaca tgcgtggtgg tggacgtgag ccacgaggat    840
cctgaggtga agtttaactg gtacgtggat ggcgtggagg tgcacaatgc caagaccaag    900
ccccgggagg agcagtacaa ctccacctat agagtggtgt ctgtgctgac agtgctgcac    960
caggactggc tgaacggcaa ggagtataag tgcaaggtgt ccaataaggc cctgcccgcc   1020
cctatcgaga gaccatctct aaggccaag ggccagccta gggagccaca ggtgtacaca   1080
ctgcctccat cccgcaagga gctgaccaag aaccaggtgt ctctgacatg tctggtgaag   1140
ggcttctatc cttctgatat cgccgtggag tgggagagca tggcagcc agagaacaat   1200 tacaagacca cacccctgt gctgaagagc gacggctcct tctttctgta tagcaagctg   1260
accgtggata gtccagatg gcagcaggc aacgtgtttt cttgtagcgt gatgcacgag   1320
gccctgcaca atcactacac acagaagtcc ctgtctctga gccctggcaa gtaa         1374
```

<210> SEQ ID NO 51
<211> LENGTH: 648
<212> TYPE: DNA
<213> ORGANISM: Artificial Sequence
<220> FEATURE:
<223> OTHER INFORMATION: Synthetic

<400> SEQUENCE: 51

```
gatattcaga tgacccagag cccgagcagc ctgagcgcaa gcgttggtga tcgtgttacc     60
attacctgta aagcaagcca gaccgttagc gcaaatgttg catggtatca gcagaaaccg    120
ggtaaagcac cgaaactgct gatttatctg gcaagctatc gttatcgtgg tgttccgagc    180
cgttttagcg gtagcggtag cggtaccgat tttacccctga ccattagcag cctgcagccg    240
gaagattttg caacctatta ttgtcatcag tattataccct atccgctgtt tacctttggt    300
cagggtacca aactggaaat taaacgtact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactta cgagaaacac aaactctacg cctgcgaagt cacccatcag    600
ggcctgagct cgcccgtcac aaagagcttc aacaggggag agtgctga                 648
```

<210> SEQ ID NO 52
<211> LENGTH: 678
<212> TYPE: DNA
<213> ORGANISM: Artificial Sequence
<220> FEATURE:
<223> OTHER INFORMATION: Synthetic

<400> SEQUENCE: 52

```
caggttcagc tggttcagag cggtagcgaa ctgaaaaaac cgggtgcaag cgttaaagtt      60
agctgtaaag caagcggtta tacctttacc gaatatggta tgaatgtttg gcgtcaggca     120
ccgggtcagg gtctggaatg gatgggttgg attaatacca aaagcggtga agcaacctat     180
gttgaagaat ttaaaggtcg ttttgttttt agcctggata ccagcgttag caccgcatat     240
ctgcagatta gcagcctgaa agcagaagat accgcagttt attattgtgc acgttgggat     300
ttttatgatt atgttgatga agcaatgtat tggggtcagg gtaccaccgt taccgttagc     360
agcgcctcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaa                                                   678
```

<210> SEQ ID NO 53
<211> LENGTH: 777
<212> TYPE: DNA
<213> ORGANISM: Artificial Sequence
<220> FEATURE:
<223> OTHER INFORMATION: Synthetic

<400> SEQUENCE: 53

```
ggcggcggca gcggcggcgg ccaggttcag ctggttcaga gcggtagcga actgaaaaaa      60
ccgggtgcaa gcgttaaagt tagctgtaaa gcaagcggtt atacctttac cgaatatggt     120
atgaatgttt ggcgtcaggc accgggtcag gtctggaatg gatgggttgg attaatacc      180
aaaagcggtg aagcaaccta tgttgaagaa tttaaaggtc gttttgtttt tagcctggat     240
accagcgtta gcaccgcata tctgcagatt agcagcctga aagcagaaga taccgcagtt     300
tattattgtg cacgttggga ttttatgat tatgttgatg aagcaatgta ttggggtcag      360
ggtaccaccg ttaccgttag cagcggtgga ggcggttcag gcggaggtgg ctctggcggt     420
ggcggatcgg atattcagat gacccagagc ccgagcagcc tgagcgcaag cgttggtgat     480
cgtgttacca ttacctgtaa agcaagccag accgttagcg caaatgttgc atggtatcag     540
cagaaaccgg gtaaagcacc gaaactgctg atttatctgg caagctatcg ttatcgtggt     600
gttccgagcc gttttagcgg tagcggtagc ggtaccgatt ttaccctgac cattagcagc     660
ctgcagccgg aagattttgc aacctattat tgtcatcagt attataccta tccgctgttt     720
acctttggtc agggtaccaa actggaaatt aaacgtcacc accaccacca ccactga       777
```

<210> SEQ ID NO 54
<211> LENGTH: 735
<212> TYPE: DNA
<213> ORGANISM: Artificial Sequence
<220> FEATURE:
<223> OTHER INFORMATION: Synthetic

<400> SEQUENCE: 54

```
gatattcaga tgacccagag cccgagcagc ctgagcgcaa gcgttggtga tcgtgttacc      60
attacctgta aagcaagcca gaccgttagc gcaaatgttg catggtatca gcagaaaccg     120
ggtaaagcac cgaaactgct gatttatctg gcaagctatc gttatcgtgg tgttccgagc     180
```

```
cgttttagcg gtagcggtag cggtaccgat tttaccctga ccattagcag cctgcagccg    240
gaagattttg caacctatta ttgtcatcag tattatacct atccgctgtt tacctttggt    300
cagggtacca aactggaaat taaacgtggt ggaggcggtt caggcggagg tggctctggc    360
ggtggcggat cgcaggttca gctggttcag agcggtagcg aactgaaaaa accgggtgca    420
agcgttaaag ttagctgtaa agcaagcggt tatacctttta ccgaatatgg tatgaatgtt    480
tggcgtcagg caccgggtca gggtctggaa tggatgggtt ggattaatac caaaagcggt    540
gaagcaacct atgttgaaga atttaaaggt cgttttgttt ttagcctgga taccagcgtt    600
agcaccgcat atctgcagat tagcagcctg aaagcagaag ataccgcagt ttattattgt    660
gcacgttggg attttttatga ttatgttgat gaagcaatgt attggggtca gggtaccacc    720
gttaccgtta gcagc                                                      735
```

<210> SEQ ID NO 55
<211> LENGTH: 687
<212> TYPE: DNA
<213> ORGANISM: Artificial Sequence
<220> FEATURE:
<223> OTHER INFORMATION: Synthetic

<400> SEQUENCE: 55

```
aggattcaga tgacccagag cccgagcagc ctgagcgcaa gcgttggtga tcgtgttacc     60
attacctgta aagcaagcca gaccgttagc gcaaatgttg catggtatca ggataaaccg    120
ggtaaagcac cgaaactgct gatttatctg gcaagctatc gttatcgtgg tgttccgagc    180
cgttttagcg gtagcggtag cggtaccgat tttaccctga ccattagcag cctgcagccg    240
gaagattttg caacctatta ttgtcatcag tattatacct atccgctgtt tacctttggt    300
cagggtacca aactggaaat taaacgtacc gtggcagcac catccgtgtt catctttccc    360
ccttctgacg agcagctgaa gtctggcaca gccagcgtgg tgtgctacct gaacaacttc    420
taccccaggg aggccaaggt gcagtggaag gtggataacg ccctgcagtc cggcaattct    480
caggagagcg tgaccgagca ggactccaag gattctacat acagcctgtg gtccaccctg    540
acactgtcca aggccgacta cgagaagcac aagctgtatg catgcgaggt gacccaccag    600
ggcctgtcct ctcccgtgac aaagagcttc aatagggagg agtgtggagg aggatcctac    660
ccttatgacg tgccagatta tgcctaa                                         687
```

<210> SEQ ID NO 56
<211> LENGTH: 1356
<212> TYPE: DNA
<213> ORGANISM: Artificial Sequence
<220> FEATURE:
<223> OTHER INFORMATION: Synthetic

<400> SEQUENCE: 56

```
caggttcagc tggttcagag cggtagcgaa ctgaaaaaac cgggtgcaag cgttaaagtt     60
agctgtaaag caagcggtta tacctttacc gaatatggta tgaatgtttg gcgtaaggca    120
ccgggtcagg gtctggaatg gatgggttgg attaatacca aaagcggtga agcaacctat    180
gttgaagaat ttaaaggtcg ttttgttttt agcctggata ccagcgttag caccgcatat    240
ctgcagatta gcagcctgaa agcagaagat accgcagttt attattgtgc acgttgggat    300
ttttatgatt atgttgatga agcaatgtat tggggtcagg gtaccaccgt taccgttagc    360
agcgcctcta caaagggacc aagcgtgttt ccactggcac cctcctctaa gagcacctcc    420
ggaggaacag ccgccctggg ctgtctggtg aaggactatt tcccagagcc cgtgaccgtg    480
```

```
tcctggaact ctggcgccct gacctccgga gtggcaacag gaccagccgt gctgcagagc      540
tccggcctgt acagcctgtc tagcgtggtg accgtgccct cctctagcct gggcacccag      600
acatatatct gcaacgtgaa tcacaagcca agcaatacaa aggtcgacaa gaaggtggag      660
cccaagtcct gtgataagac ccacacatgc ccccttgtc ctgcaccaga gctgctggga      720
ggaccaagcg tgttcctgtt tccacccaag cctaaggaca ccctgatgat ctctaggacc      780
cccgaggtga catgcgtggt ggtggacgtg agccacgagg atcctgaggt gaagtttaac      840
tggtacgtgg atggcgtgga ggtgcacaat gccaagacca agccccggga ggagcagtac      900
aactccacct atagagtggt gtctgtgctg acagtgctgc accaggactg gctgaacggc      960
aaggagtata agtgcaaggt gtccaataag gccctgcccg cccctatcga aagaccatc     1020 tctaaggcca agggccagcc tagggagcca caggtgtaca cactgcctcc atcccgcaag     1080
gagctgacca agaaccaggt gtctctgaca tgtctggtga agggcttcta tccttctgat     1140
atcgccgtgg agtgggagag caatggccag ccagagaaca attacaagac cacacccct     1200 gtgctgaaga gcgacggctc cttctttctg tatagcaagc tgaccgtgga taagtccaga     1260
tggcagcagg gcaacgtgtt ttcttgtagc gtgatgcacg aggccctgca caatcactac     1320
acacagaagt ccctgtctct gagccctggc aagtaa                              1356
```

```
<210> SEQ ID NO 57
<211> LENGTH: 654
<212> TYPE: DNA
<213> ORGANISM: Artificial Sequence
<220> FEATURE:
<223> OTHER INFORMATION: Synthetic

<400> SEQUENCE: 57
```

```
gatattcaga tgacccagag cccgagcagc ctgagcgcga gcgtgggcga tcgcgtgacc       60
attacctgcc aggcgagcca gagcattagc agcagctatc tgagctggta tcagcagaaa      120
ccgggcaaag cgccgaaact gctgatttat gcggtgagct atctggcgag cggcgtgccg      180
agccgcttta gcggcagcgg cagcggcacc gatttcaccc tgaccattag cagcctgcag      240
ccggaagatt ttgcgaccta ttattgccag agcggctatt atagcgcggg cgatctgacc      300
tttggccagg gcaccaaagt ggaaattaaa cgcactgtgg ctgcaccatc tgtcttcatc      360
ttcccgccat ctgatgagca gttgaaatct ggaactgcct ctgttgtgtg cctgctgaat      420
aacttctatc ccagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaac tctacgcctg cgaagtcacc      600
catcagggcc tgagctcgcc cgtcacaaag agcttcaaca ggggagagtg ctga            654
```

```
<210> SEQ ID NO 58
<211> LENGTH: 660
<212> TYPE: DNA
<213> ORGANISM: Artificial Sequence
<220> FEATURE:
<223> OTHER INFORMATION: Synthetic

<400> SEQUENCE: 58
```

```
gaagtgcagc tggtggaaag cggcggcggc ctggtgcagc cgggcggcag cctgcgcctg       60
agctgcgcgg cgagcggctt tagcctgagc aactattata ttaactgggt gcgccaggcg      120
ccgggcaaag gcctggaatg ggtggcgatt attttttgcg cgggcaacgc gtataacgcg      180
```

```
agctgggcga aaggccgctt taccattagc cgcgatgata gcaaaaacac cctgtatctg      240
cagatgaaca gcctgcgcgc ggaagatacc gcggtgtatt attgcgcgcg cggctggcag      300
gcgctggtga actggggcca gggcaccctg gtgaccgtga gcagcgcctc caccaagggc      360
ccatcggtct tccccctggc accctcctcc aagagcacct ctgggggcac agcggccctg      420
ggctgcctgg tcaaggacta cttccccgaa ccggtgacgg tgtcgtggaa ctcaggcgcc      480
ctgaccagcg gcgtgcacac cttcccggct gtcctacagt cctcaggact ctactccctc      540
agcagcgtgg tgaccgtgcc ctccagcagc ttgggcaccc agacctacat ctgcaacgtg      600
aatcacaagc ccagcaacac caaggtggac aagagagttg agcccaaatc ttgtgacaaa      660
```

<210> SEQ ID NO 59
<211> LENGTH: 765
<212> TYPE: DNA
<213> ORGANISM: Artificial Sequence
<220> FEATURE:
<223> OTHER INFORMATION: Synthetic

<400> SEQUENCE: 59

```
ggcggcggca gcggcggcgg cgaagtgcag ctggtggaaa gcggcggcgg cctggtgcag       60
ccgggcggca gcctgcgcct gagctgcgcg gcgagcggct ttagcctgag caactattat      120
attaactggg tgcgccaggc gccgggcaaa ggcctggaat gggtggcgat tattttttgc      180
gcgggcaacg cgtataacgc gagctgggcg aaaggccgct taccattag ccgcgatgat      240 agcaaaaaca ccctgtatct gcagatgaac agcctgcgcg cggaagatac cgcggtgtat      300
tattgcgcgc gcggctggca ggcgctggtg aactggggcc agggcaccct ggtgaccgtg      360
agcagcggcg gcggcggcag cggcggcggc ggcagcggcg gcggcggcag cgatattcag      420
atgacccaga gcccgagcag cctgagcgcg agcgtgggcg atcgcgtgac cattacctgc      480
caggcgagcc agagcattag cagcagctat ctgagctggt atcagcagaa accgggcaaa      540
gcgccgaaac tgctgattta tcgggtgagc tatctggcga gcggcgtgcc gagccgcttt      600
agcggcagcg gcagcggcac cgatttcacc ctgaccatta gcagcctgca gccggaagat      660
tttgcgacct attattgcca gagcggctat tatagcgcgg gcgatctgac ctttggccag      720
ggcaccaaag tggaaattaa acgccaccac caccaccacc actga                      765
```

<210> SEQ ID NO 60
<211> LENGTH: 723
<212> TYPE: DNA
<213> ORGANISM: Artificial Sequence
<220> FEATURE:
<223> OTHER INFORMATION: Synthetic

<400> SEQUENCE: 60

```
gatattcaga tgacccagag cccgagcagc ctgagcgcga gcgtgggcga tcgcgtgacc       60
attacctgcc aggcgagcca gagcattagc agcagctatc tgagctggta tcagcagaaa      120
ccgggcaaag cgccgaaact gctgatttat cgggtgagct atctggcgag cggcgtgccg      180
agccgcttta gcggcagcgg cagcggcacc gatttcaccc tgaccattag cagcctgcag      240
ccggaagatt ttgcgaccta ttattgccag agcggctatt atagcgcggg cgatctgacc      300
tttggccagg gcaccaaagt ggaaattaaa cgcggtggag cggttcaggg cggaggtggc      360
tctggcggtg gcggatcgga agtgcagctg gtggaaagcg gcggcggcct ggtgcagccg      420
ggcggcagcc tgcgcctgag ctgcgcggcg agcggcttta gcctgagcaa ctattatatt      480
aactgggtgc gccaggcgcc gggcaaaggc ctggaatggg tggcgattat tttttgcgcg      540
```

```
ggcaacgcgt ataacgcgag ctgggcgaaa ggccgcttta ccattagccg cgatgatagc    600
aaaaacaccc tgtatctgca gatgaacagc ctgcgcgcgg aagataccgc ggtgtattat    660
tgcgcgcgcg gctggcaggc gctggtgaac tggggccagg caccctggt gaccgtgagc     720 agc                                                                  723
```

```
<210> SEQ ID NO 61
<211> LENGTH: 693
<212> TYPE: DNA
<213> ORGANISM: Artificial Sequence
<220> FEATURE:
<223> OTHER INFORMATION: Synthetic

<400> SEQUENCE: 61
aggattcaga tgacccagag cccgagcagc ctgagcgcga gcgtgggcga tcgcgtgacc     60
attacctgcc aggcgagcca gagcattagc agcagctatc tgagctggta tcaggataaa   120
ccgggcaaag cgccgaaact gctgatttat gcggtgagct atctggcgag cggcgtgccg   180
agccgcttta gcggcagcgg cagcggcacc gatttcaccc tgaccattag cagcctgcag   240
ccggaagatt ttgcgaccta ttattgccag agcggctatt atagcgcggg cgatctgacc   300
tttggccagg gcaccaaagt ggaaattaaa cgcaccgtgg cagcaccatc cgtgttcatc   360 ttccccctt ctgacgagca gctgaagtct ggcacagcca gcgtggtgtg ctacctgaac    420
aacttctacc ccagggaggc caaggtgcag tggaaggtgg ataacgccct gcagtccggc   480
aattctcagg agagcgtgac cgagcaggac tccaaggatt ctacatacag cctgtggtcc   540
accctgacac tgtccaaggc cgactacgag aagcacaagc tgtatgcatg cgaggtgacc   600
caccagggcc tgtcctctcc cgtgacaaag agcttcaata ggggagagtg tggaggagga   660 tcctacccctt atgacgtgcc agattatgcc taa                                693
```

```
<210> SEQ ID NO 62
<211> LENGTH: 1338
<212> TYPE: DNA
<213> ORGANISM: Artificial Sequence
<220> FEATURE:
<223> OTHER INFORMATION: Synthetic

<400> SEQUENCE: 62
gaagtgcagc tggtggaaag cggcggcggc ctggtgcagc cgggcggcag cctgcgcctg     60
agctgcgcgg cgagcggctt tagcctgagc aactattata ttaactgggt gcgcaaggcg   120
ccgggcaaag gcctggaatg ggtggcgatt attttttgcg cgggcaacgc gtataacgcg   180
agctgggcga aggcgagtt taccattagc cgcgatgata gcaaaaacac cctgtatctg   240
cagatgaaca gcctgcgcgc ggaagatacc gcggtgtatt attgcgcgcg cggctggcag   300
gcgctggtga actggggcca gggcaccctg gtgaccgtga gcagcgcctc tacaaaggga   360
ccaagcgtgt tccactggc accctcctct aagagcacct ccgaggaac agccgccctg    420 ggctgtctgg tgaaggacta tttcccagag cccgtgaccg tgtcctggaa ctctggcgcc   480
ctgacctccg gagtggcaac aggaccagcc gtgctgcaga gctccggcct gtacagcctg   540
tctagcgtgg tgaccgtgcc ctcctctagc ctgggcaccc agacatatat ctgcaacgtg   600
aatcacaagc caagcaatac aaaggtcgac aagaaggtgg agcccaagtc ctgtgataag   660
acccacacat gccccccttg tcctgcacca gagctgctgg gaggaccaag cgtgttcctg   720
tttccaccca gcctaagga caccctgatg atctctagga cccccgaggt gacatgcgtg   780
```

```
gtggtggacg tgagccacga ggatcctgag gtgaagttta actggtacgt ggatggcgtg    840
gaggtgcaca atgccaagac caagcccggg gaggagcagt acaactccac ctatagagtg    900
gtgtctgtgc tgacagtgct gcaccaggac tggctgaacg gcaaggagta taagtgcaag    960
gtgtccaata aggccctgcc cgcccctatc gagaagacca tctctaaggc caagggccag   1020
cctagggagc cacaggtgta cacactgcct ccatcccgca aggagctgac caagaaccag   1080
gtgtctctga catgtctggt gaagggcttc tatccttctg atatcgccgt ggagtgggag   1140
agcaatggcc agccagagaa caattacaag accacacccc ctgtgctgaa gagcgacggc   1200
tccttctttc tgtatagcaa gctgaccgtg gataagtcca gatggcagca gggcaacgtg   1260
ttttcttgta gcgtgatgca cgaggccctg cacaatcact acacacagaa gtccctgtct   1320
ctgagccctg gcaagtaa                                                 1338
```

```
<210> SEQ ID NO 63
<211> LENGTH: 21
<212> TYPE: PRT
<213> ORGANISM: Artificial Sequence
<220> FEATURE:
<223> OTHER INFORMATION: Synthetic

<400> SEQUENCE: 63

Met Glu Thr Asp Thr Leu Leu Leu Trp Val Leu Leu Leu Trp Val Pro
1               5                   10                  15

Gly Ser Thr Gly Asp
            20
```

```
<210> SEQ ID NO 64
<211> LENGTH: 214
<212> TYPE: PRT
<213> ORGANISM: Artificial Sequence
<220> FEATURE:
<223> OTHER INFORMATION: Synthetic

<400> SEQUENCE: 64

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 220
<212> TYPE: PRT
<213> ORGANISM: Artificial Sequence
<220> FEATURE:
<223> OTHER INFORMATION: Synthetic

<400> SEQUENCE: 65

Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ala Ser Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys
    210                 215                 220

<210> SEQ ID NO 66
<211> LENGTH: 257
<212> TYPE: PRT
<213> ORGANISM: Artificial Sequence
<220> FEATURE:
<223> OTHER INFORMATION: Synthetic

<400> SEQUENCE: 66

Gly Gly Gly Ser Gly Gly Gly Asp Ile Lys Leu Gln Gln Ser Gly Ala
1               5                   10                  15

Glu Leu Ala Arg Pro Gly Ala Ser Val Lys Met Ser Cys Lys Thr Ser
            20                  25                  30

Gly Tyr Thr Phe Thr Arg Tyr Thr Met His Trp Val Lys Gln Arg Pro
        35                  40                  45
```

```
Gly Gln Gly Leu Glu Trp Ile Gly Tyr Ile Asn Pro Ser Arg Gly Tyr
            50                  55                  60

Thr Asn Tyr Asn Gln Lys Phe Lys Asp Lys Ala Thr Leu Thr Thr Asp
 65                  70                  75                  80

Lys Ser Ser Ser Thr Ala Tyr Met Gln Leu Ser Ser Leu Thr Ser Glu
                    85                  90                  95

Asp Ser Ala Val Tyr Tyr Cys Ala Arg Tyr Tyr Asp Asp His Tyr Cys
                100                 105                 110

Leu Asp Tyr Trp Gly Gln Gly Thr Thr Leu Thr Val Ser Ser Val Glu
            115                 120                 125

Gly Gly Ser Gly Gly Ser Gly Ser Gly Gly Ser Gly Gly Val Asp
        130                 135                 140

Asp Ile Gln Leu Thr Gln Ser Pro Ala Ile Met Ser Ala Ser Pro Gly
145                 150                 155                 160

Glu Lys Val Thr Met Thr Cys Arg Ala Ser Ser Ser Val Ser Tyr Met
                165                 170                 175

Asn Trp Tyr Gln Gln Lys Ser Gly Thr Ser Pro Lys Arg Trp Ile Tyr
            180                 185                 190

Asp Thr Ser Lys Val Ala Ser Gly Val Pro Tyr Arg Phe Ser Gly Ser
        195                 200                 205

Gly Ser Gly Thr Ser Tyr Ser Leu Thr Ile Ser Ser Met Glu Ala Glu
    210                 215                 220

Asp Ala Ala Thr Tyr Tyr Cys Gln Gln Trp Ser Ser Asn Pro Leu Thr
225                 230                 235                 240

Phe Gly Ala Gly Thr Lys Leu Glu Leu Lys Arg His His His His His
                245                 250                 255

His

<210> SEQ ID NO 67
<211> LENGTH: 213
<212> TYPE: PRT
<213> ORGANISM: Artificial Sequence
<220> FEATURE:
<223> OTHER INFORMATION: Synthetic

<400> SEQUENCE: 67

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
 65                 70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Leu Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 68
<211> LENGTH: 217
<212> TYPE: PRT
<213> ORGANISM: Artificial Sequence
<220> FEATURE:
<223> OTHER INFORMATION: Synthetic

<400> SEQUENCE: 68

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val
    210                 215
```

<210> SEQ ID NO 69
<211> LENGTH: 252
<212> TYPE: PRT
<213> ORGANISM: Artificial Sequence
<220> FEATURE:
<223> OTHER INFORMATION: Synthetic

<400> SEQUENCE: 69

```
Gly Gly Gly Ser Gly Gly Gly Glu Val Gln Leu Val Gln Ser Gly Ala
1               5                   10                  15
```

```
Glu Val Lys Lys Pro Gly Ala Ser Val Lys Ile Ser Cys Lys Thr Ser
                20                  25                  30
Gly Tyr Thr Phe Thr Glu Tyr Thr Ile His Trp Val Lys Gln Ala Ser
            35                  40                  45
Gly Lys Gly Leu Glu Trp Ile Gly Asn Ile Asn Pro Asn Asn Gly Gly
        50                  55                  60
Thr Thr Tyr Asn Gln Lys Phe Glu Asp Arg Ala Thr Leu Thr Val Asp
65                  70                  75                  80
Lys Ser Thr Ser Thr Ala Tyr Met Glu Leu Ser Ser Leu Arg Ser Glu
                85                  90                  95
Asp Thr Ala Val Tyr Tyr Cys Ala Ala Gly Trp Asn Phe Asp Tyr Trp
            100                 105                 110
Gly Gln Gly Thr Thr Val Thr Val Ser Ser Ala Gly Gly Gly Gly Ser
        115                 120                 125
Gly Gly Gly Gly Ser Gly Gly Gly Ser Asp Ile Val Met Thr Gln
        130                 135                 140
Ser Pro Ser Ser Leu Ser Ala Ser Val Gly Asp Arg Val Thr Ile Thr
145                 150                 155                 160
Cys Lys Ala Ser Gln Asp Val Gly Thr Ala Val Asp Trp Tyr Gln Gln
                165                 170                 175
Lys Pro Gly Lys Ala Pro Lys Leu Leu Ile Tyr Trp Ala Ser Thr Arg
            180                 185                 190
His Thr Gly Val Pro Asp Arg Phe Thr Gly Ser Gly Ser Gly Thr Asp
        195                 200                 205
Phe Thr Leu Thr Ile Ser Ser Leu Gln Pro Glu Asp Phe Ala Asp Tyr
210                 215                 220
Phe Cys Gln Gln Tyr Asn Ser Tyr Pro Leu Thr Phe Gly Gly Gly Thr
225                 230                 235                 240
Lys Leu Glu Ile Lys Arg His His His His His
            245                 250

<210> SEQ ID NO 70
<211> LENGTH: 239
<212> TYPE: PRT
<213> ORGANISM: Artificial Sequence
<220> FEATURE:
<223> OTHER INFORMATION: Synthetic

<400> SEQUENCE: 70

Asp Ile Val Met Thr Gln Ser Pro Ser Ser Leu Ser Ala Ser Val Gly
1               5                   10                  15
Asp Arg Val Thr Ile Thr Cys Lys Ala Ser Gln Asp Val Gly Thr Ala
                20                  25                  30
Val Asp Trp Tyr Gln Gln Lys Pro Gly Lys Ala Pro Lys Leu Leu Ile
            35                  40                  45
Tyr Trp Ala Ser Thr Arg His Thr Gly Val Pro Asp Arg Phe Thr Gly
        50                  55                  60
Ser Gly Ser Gly Thr Asp Phe Thr Leu Thr Ile Ser Ser Leu Gln Pro
65                  70                  75                  80
Glu Asp Phe Ala Asp Tyr Phe Cys Gln Gln Tyr Asn Ser Tyr Pro Leu
                85                  90                  95
Thr Phe Gly Gly Gly Thr Lys Leu Glu Ile Lys Arg Gly Gly Gly Gly
            100                 105                 110
Ser Gly Gly Gly Gly Ser Gly Gly Gly Gly Ser Glu Val Gln Leu Val
        115                 120                 125
```

```
Gln Ser Gly Ala Glu Val Lys Lys Pro Gly Ala Ser Val Lys Ile Ser
            130                 135                 140

Cys Lys Thr Ser Gly Tyr Thr Phe Thr Glu Tyr Thr Ile His Trp Val
145                 150                 155                 160

Lys Gln Ala Ser Gly Lys Gly Leu Glu Trp Ile Gly Asn Ile Asn Pro
                165                 170                 175

Asn Asn Gly Gly Thr Thr Tyr Asn Gln Lys Phe Glu Asp Arg Ala Thr
                180                 185                 190

Leu Thr Val Asp Lys Ser Thr Ser Thr Ala Tyr Met Glu Leu Ser Ser
        195                 200                 205

Leu Arg Ser Glu Asp Thr Ala Val Tyr Tyr Cys Ala Ala Gly Trp Asn
    210                 215                 220

Phe Asp Tyr Trp Gly Gln Gly Thr Thr Val Thr Val Ser Ser Ala
225                 230                 235
```

<210> SEQ ID NO 71
<211> LENGTH: 223
<212> TYPE: PRT
<213> ORGANISM: Artificial Sequence
<220> FEATURE:
<223> OTHER INFORMATION: Synthetic

<400> SEQUENCE: 71

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Arg Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Leu Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser His His His His His His
    210                 215                 220
```

<210> SEQ ID NO 72
<211> LENGTH: 449
<212> TYPE: PRT
<213> ORGANISM: Artificial Sequence

```
<220> FEATURE:
<223> OTHER INFORMATION: Synthetic

<400> SEQUENCE: 72

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Tyr Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Asp Thr Thr Pro Pro Val Leu
385                 390                 395                 400
```

```
Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 73
<211> LENGTH: 227
<212> TYPE: PRT
<213> ORGANISM: Artificial Sequence
<220> FEATURE:
<223> OTHER INFORMATION: Synthetic

<400> SEQUENCE: 73

Arg Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Asp Lys Pro Gly Lys Ala Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Tyr Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Trp
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Tyr Pro Tyr Asp Val Pro
    210                 215                 220

Asp Tyr Ala
225

<210> SEQ ID NO 74
<211> LENGTH: 445
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Gln Ser Gly Ala Glu Val Lys Lys Pro Gly Ala
1               5                   10                  15
```

Ser Val Lys Ile Ser Cys Lys Thr Ser Gly Tyr Thr Phe Thr Glu Tyr
            20                  25                  30

Thr Ile His Trp Val Lys Lys Ala Ser Gly Lys Gly Leu Glu Trp Ile
        35                  40                  45

Gly Asn Ile Asn Pro Asn Asn Gly Gly Thr Thr Tyr Asn Gln Glu Phe
 50                  55                  60

Glu Asp Arg Ala Thr Leu Thr Val Asp Lys Ser Thr Ser Thr Ala Tyr
65                   70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val Ala Thr Gly Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Lys Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Lys Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

-continued

His Tyr Thr Gln Lys Ser Leu Ser Leu Ser Pro Gly Lys
            435                 440                 445

<210> SEQ ID NO 75
<211> LENGTH: 214
<212> TYPE: PRT
<213> ORGANISM: Artificial Sequence
<220> FEATURE:
<223> OTHER INFORMATION: Synthetic

<400> SEQUENCE: 75

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 224
<212> TYPE: PRT
<213> ORGANISM: Artificial Sequence
<220> FEATURE:
<223> OTHER INFORMATION: Synthetic

<400> SEQUENCE: 76

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

```
Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
               100                 105                 110

Thr Leu Val Thr Val Ser Ala Ala Ser Thr Lys Gly Pro Ser Val Phe
           115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
               165                 170                 175

Gln Ser Ser Gly Leu Tyr Ser Leu Ser Ser Val Val Thr Val Pro Ser
           180                 185                 190

Ser Ser Leu Gly Thr Gln Thr Tyr Ile Cys Asn Val Asn His Lys Pro
       195                 200                 205

Ser Asn Thr Lys Val Asp Lys Arg Val Glu Pro Lys Ser Cys Asp Lys
210                 215                 220
```

<210> SEQ ID NO 77
<211> LENGTH: 255
<212> TYPE: PRT
<213> ORGANISM: Artificial Sequence
<220> FEATURE:
<223> OTHER INFORMATION: Synthetic

<400> SEQUENCE: 77

```
Gly Gly Gly Ser Gly Gly Gly Gln Val Gln Leu Lys Gln Ser Gly Pro
1               5                   10                  15

Gly Leu Val Gln Pro Ser Gln Ser Leu Ser Ile Thr Cys Thr Val Ser
           20                  25                  30

Gly Phe Ser Leu Thr Asn Tyr Gly Val His Trp Val Arg Gln Ser Pro
       35                  40                  45

Gly Lys Gly Leu Glu Trp Leu Gly Val Ile Trp Ser Gly Gly Asn Thr
   50                  55                  60

Asp Tyr Asn Thr Pro Phe Thr Ser Arg Leu Ser Ile Asn Lys Asp Asn
65                  70                  75                  80

Ser Lys Ser Gln Val Phe Phe Lys Met Asn Ser Leu Gln Ser Asn Asp
                85                  90                  95

Thr Ala Ile Tyr Tyr Cys Ala Arg Ala Leu Thr Tyr Tyr Asp Tyr Glu
               100                 105                 110

Phe Ala Tyr Trp Gly Gln Gly Thr Leu Val Thr Val Ser Ala Gly Gly
           115                 120                 125

Gly Gly Ser Gly Gly Gly Gly Ser Gly Gly Gly Gly Ser Asp Ile Leu
130                 135                 140

Leu Thr Gln Ser Pro Val Ile Leu Ser Val Ser Pro Gly Glu Arg Val
145                 150                 155                 160

Ser Phe Ser Cys Arg Ala Ser Gln Ser Ile Gly Thr Asn Ile His Trp
               165                 170                 175

Tyr Gln Gln Arg Thr Asn Gly Ser Pro Arg Leu Leu Ile Lys Tyr Ala
           180                 185                 190

Ser Glu Ser Ile Ser Gly Ile Pro Ser Arg Phe Ser Gly Ser Gly Ser
       195                 200                 205

Gly Thr Asp Phe Thr Leu Ser Ile Asn Ser Val Glu Ser Glu Asp Ile
210                 215                 220
```

```
Ala Asp Tyr Tyr Cys Gln Gln Asn Asn Asn Trp Pro Thr Thr Phe Gly
225                 230                 235                 240

Ala Gly Thr Lys Leu Glu Leu Lys Arg His His His His His
                245                 250                 255

<210> SEQ ID NO 78
<211> LENGTH: 242
<212> TYPE: PRT
<213> ORGANISM: Artificial Sequence
<220> FEATURE:
<223> OTHER INFORMATION: Synthetic

<400> SEQUENCE: 78

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Gly Gly Gly Gly
            100                 105                 110

Ser Gly Gly Gly Gly Ser Gly Gly Gly Ser Gln Val Gln Leu Lys
        115                 120                 125

Gln Ser Gly Pro Gly Leu Val Gln Pro Ser Gln Ser Leu Ser Ile Thr
    130                 135                 140

Cys Thr Val Ser Gly Phe Ser Leu Thr Asn Tyr Gly Val His Trp Val
145                 150                 155                 160

Arg Gln Ser Pro Gly Lys Gly Leu Glu Trp Leu Gly Val Ile Trp Ser
                165                 170                 175

Gly Gly Asn Thr Asp Tyr Asn Thr Pro Phe Thr Ser Arg Leu Ser Ile
            180                 185                 190

Asn Lys Asp Asn Ser Lys Ser Gln Val Phe Phe Lys Met Asn Ser Leu
        195                 200                 205

Gln Ser Asn Asp Thr Ala Ile Tyr Tyr Cys Ala Arg Ala Leu Thr Tyr
    210                 215                 220

Tyr Asp Tyr Glu Phe Ala Tyr Trp Gly Gln Gly Thr Leu Val Thr Val
225                 230                 235                 240

Ser Ala

<210> SEQ ID NO 79
<211> LENGTH: 254
<212> TYPE: PRT
<213> ORGANISM: Artificial Sequence
<220> FEATURE:
<223> OTHER INFORMATION: Synthetic

<400> SEQUENCE: 79

Gly Gly Gly Ser Asp Ile Lys Leu Gln Gln Ser Gly Ala Glu Leu Ala
1               5                   10                  15

Arg Pro Gly Ala Ser Val Lys Met Ser Cys Lys Thr Ser Gly Tyr Thr
                20                  25                  30
```

```
Phe Thr Arg Tyr Thr Met His Trp Val Lys Gln Arg Pro Gly Gln Gly
            35                  40                  45

Leu Glu Trp Ile Gly Tyr Ile Asn Pro Ser Arg Gly Tyr Thr Asn Tyr
 50                  55                  60

Asn Gln Lys Phe Lys Asp Lys Ala Thr Leu Thr Thr Asp Lys Ser Ser
 65                  70                  75                  80

Ser Thr Ala Tyr Met Gln Leu Ser Ser Leu Thr Ser Glu Asp Ser Ala
                 85                  90                  95

Val Tyr Tyr Cys Ala Arg Tyr Tyr Asp Asp His Tyr Cys Leu Asp Tyr
            100                 105                 110

Trp Gly Gln Gly Thr Thr Leu Thr Val Ser Ser Val Glu Gly Gly Ser
            115                 120                 125

Gly Gly Ser Gly Gly Ser Gly Gly Ser Gly Gly Val Asp Asp Ile Gln
        130                 135                 140

Leu Thr Gln Ser Pro Ala Ile Met Ser Ala Ser Pro Gly Glu Lys Val
145                 150                 155                 160

Thr Met Thr Cys Arg Ala Ser Ser Ser Val Ser Tyr Met Asn Trp Tyr
                165                 170                 175

Gln Gln Lys Ser Gly Thr Ser Pro Lys Arg Trp Ile Tyr Asp Thr Ser
            180                 185                 190

Lys Val Ala Ser Gly Val Pro Tyr Arg Phe Ser Gly Ser Gly Ser Gly
            195                 200                 205

Thr Ser Tyr Ser Leu Thr Ile Ser Ser Met Glu Ala Glu Asp Ala Ala
        210                 215                 220

Thr Tyr Tyr Cys Gln Gln Trp Ser Ser Asn Pro Leu Thr Phe Gly Ala
225                 230                 235                 240

Gly Thr Lys Leu Glu Leu Lys Arg His His His His His His
                245                 250

<210> SEQ ID NO 80
<211> LENGTH: 227
<212> TYPE: PRT
<213> ORGANISM: Artificial Sequence
<220> FEATURE:
<223> OTHER INFORMATION: Synthetic

<400> SEQUENCE: 80

Arg Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
                 20                  25                  30

Ile His Trp Tyr Gln Asp Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Tyr Leu Asn Asn Phe Tyr Pro Arg Glu Ala
            130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Trp
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Tyr Pro Tyr Asp Val Pro
    210                 215                 220

Asp Tyr Ala
225

<210> SEQ ID NO 81
<211> LENGTH: 449
<212> TYPE: PRT
<213> ORGANISM: Artificial Sequence
<220> FEATURE:
<223> OTHER INFORMATION: Synthetic

<400> SEQUENCE: 81

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Lys Ser Pro Gly Lys Gly Leu Glu Trp Leu
            35                  40                  45

Gly Val Ile Trp Ser Gly Gly Asn Thr Asp Tyr Asn Thr Glu Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Lys Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 82
<211> LENGTH: 214
<212> TYPE: PRT
<213> ORGANISM: Artificial Sequence
<220> FEATURE:
<223> OTHER INFORMATION: Synthetic

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 83
<211> LENGTH: 223
<212> TYPE: PRT
<213> ORGANISM: Artificial Sequence
<220> FEATURE:
<223> OTHER INFORMATION: Synthetic

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys
    210                 215                 220
```

<210> SEQ ID NO 84
<211> LENGTH: 257
<212> TYPE: PRT
<213> ORGANISM: Artificial Sequence
<220> FEATURE:
<223> OTHER INFORMATION: Synthetic

<400> SEQUENCE: 84

```
Gly Gly Gly Ser Gly Gly Gly Glu Val Gln Leu Val Glu Ser Gly Gly
1               5                   10                  15

Gly Leu Val Gln Pro Gly Gly Ser Leu Arg Leu Ser Cys Ala Ala Ser
            20                  25                  30

Gly Phe Thr Phe Ser Asp Ser Trp Ile His Trp Val Arg Gln Ala Pro
        35                  40                  45
```

```
Gly Lys Gly Leu Glu Trp Val Ala Trp Ile Ser Pro Tyr Gly Gly Ser
         50                  55                  60

Thr Tyr Tyr Ala Asp Ser Val Lys Gly Arg Phe Thr Ile Ser Ala Asp
 65                  70                  75                  80

Thr Ser Lys Asn Thr Ala Tyr Leu Gln Met Asn Ser Leu Arg Ala Glu
                 85                  90                  95

Asp Thr Ala Val Tyr Tyr Cys Ala Arg Arg His Trp Pro Gly Gly Phe
            100                 105                 110

Asp Tyr Trp Gly Gln Gly Thr Leu Val Thr Val Ser Ala Val Glu Gly
        115                 120                 125

Gly Ser Gly Gly Ser Gly Ser Gly Gly Ser Gly Gly Val Asp Asp
        130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Asp Val Ser Thr Ala Val
                165                 170                 175

Ala Trp Tyr Gln Gln Lys Pro Gly Lys Ala Pro Lys Leu Leu Ile Tyr
            180                 185                 190

Ser Ala Ser Phe Leu Tyr Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Tyr Leu Tyr His Pro Ala Thr
225                 230                 235                 240

Phe Gly Gln Gly Thr Lys Val Glu Ile Lys Arg His His His His
                245                 250                 255

His

<210> SEQ ID NO 85
<211> LENGTH: 241
<212> TYPE: PRT
<213> ORGANISM: Artificial Sequence
<220> FEATURE:
<223> OTHER INFORMATION: Synthetic

<400> SEQUENCE: 85

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140
```

```
Cys Ala Ala Ser Gly Phe Thr Phe Ser Asp Ser Trp Ile His Trp Val
145                 150                 155                 160

Arg Gln Ala Pro Gly Lys Gly Leu Glu Trp Val Ala Trp Ile Ser Pro
                165                 170                 175

Tyr Gly Gly Ser Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg His Trp
    210                 215                 220

Pro Gly Gly Phe Asp Tyr Trp Gly Gln Gly Thr Leu Val Thr Val Ser
225                 230                 235                 240

Ala

<210> SEQ ID NO 86
<211> LENGTH: 227
<212> TYPE: PRT
<213> ORGANISM: Artificial Sequence
<220> FEATURE:
<223> OTHER INFORMATION: Synthetic

<400> SEQUENCE: 86

Arg Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Asp Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Tyr Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Trp
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Tyr Pro Tyr Asp Val Pro
    210                 215                 220

Asp Tyr Ala
225

<210> SEQ ID NO 87
<211> LENGTH: 448
<212> TYPE: PRT
```

<213> ORGANISM: Artificial Sequence
<220> FEATURE:
<223> OTHER INFORMATION: Synthetic

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Lys Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Glu Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val Ala Thr Gly Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Lys Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

Asn Gly Gln Pro Glu Asn Asn Tyr Lys Thr Thr Pro Pro Val Leu Lys
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 88
<211> LENGTH: 214
<212> TYPE: PRT
<213> ORGANISM: Artificial Sequence
<220> FEATURE:
<223> OTHER INFORMATION: Synthetic

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 89
<211> LENGTH: 225
<212> TYPE: PRT
<213> ORGANISM: Artificial Sequence
<220> FEATURE:
<223> OTHER INFORMATION: Synthetic

<400> SEQUENCE: 89

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys
225

<210> SEQ ID NO 90
<211> LENGTH: 256
<212> TYPE: PRT
<213> ORGANISM: Artificial Sequence
<220> FEATURE:
<223> OTHER INFORMATION: Synthetic

<400> SEQUENCE: 90

Gly Gly Gly Ser Gly Gly Gly Glu Val Gln Leu Val Glu Ser Gly Gly
1               5                  10                  15

Gly Leu Val Gln Pro Gly Gly Ser Leu Arg Leu Ser Cys Ala Ala Ser
             20                  25                  30

Gly Phe Asn Ile Lys Asp Thr Tyr Ile His Trp Val Arg Gln Ala Pro
         35                  40                  45

Gly Lys Gly Leu Glu Trp Val Ala Arg Ile Tyr Pro Thr Asn Gly Tyr
 50                  55                  60

Thr Arg Tyr Ala Asp Ser Val Lys Gly Arg Phe Thr Ile Ser Ala Asp
 65                  70                  75                  80

Thr Ser Lys Asn Thr Ala Tyr Leu Gln Met Asn Ser Leu Arg Ala Glu
                 85                  90                  95

Asp Thr Ala Val Tyr Tyr Cys Ser Arg Trp Gly Gly Asp Gly Phe Tyr
                100                 105                 110

Ala Met Asp Tyr Trp Gly Gln Gly Thr Leu Val Thr Val Ser Ser Gly
            115                 120                 125

Gly Gly Gly Ser Gly Gly Gly Ser Gly Gly Gly Ser Asp Ile
130                 135                 140
```

```
Gln Met Thr Gln Ser Pro Ser Leu Ser Ala Ser Val Gly Asp Arg
145                 150                 155                 160

Val Thr Ile Thr Cys Arg Ala Ser Gln Asp Val Asn Thr Ala Val Ala
            165                 170                 175

Trp Tyr Gln Gln Lys Pro Gly Lys Ala Pro Lys Leu Leu Ile Tyr Ser
        180                 185                 190

Ala Ser Phe Leu Tyr Ser Gly Val Pro Ser Arg Phe Ser Gly Ser Arg
    195                 200                 205

Ser Gly Thr Asp Phe Thr Leu Thr Ile Ser Ser Leu Gln Pro Glu Asp
210                 215                 220

Phe Ala Thr Tyr Tyr Cys Gln Gln His Tyr Thr Thr Pro Pro Thr Phe
225                 230                 235                 240

Gly Gln Gly Thr Lys Val Glu Ile Lys Arg His His His His His His
            245                 250                 255

<210> SEQ ID NO 91
<211> LENGTH: 243
<212> TYPE: PRT
<213> ORGANISM: Artificial Sequence
<220> FEATURE:
<223> OTHER INFORMATION: Synthetic

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
            165                 170                 175

Thr Asn Gly Tyr Thr Arg Tyr Ala Asp Ser Val Lys Gly Arg Phe Thr
        180                 185                 190

Ile Ser Ala Asp Thr Ser Lys Asn Thr Ala Tyr Leu Gln Met Asn Ser
    195                 200                 205

Leu Arg Ala Glu Asp Thr Ala Val Tyr Tyr Cys Ser Arg Trp Gly Gly
210                 215                 220

Asp Gly Phe Tyr Ala Met Asp Tyr Trp Gly Gln Gly Thr Leu Val Thr
225                 230                 235                 240

Val Ser Ser
```

```
<210> SEQ ID NO 92
<211> LENGTH: 227
<212> TYPE: PRT
<213> ORGANISM: Artificial Sequence
<220> FEATURE:
<223> OTHER INFORMATION: Synthetic

<400> SEQUENCE: 92

Arg Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Asp Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Tyr Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Trp
                165                 170                 175

Ser Thr Leu Thr Leu Ser Lys Ala Asp Tyr Glu Lys His Lys Leu Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Tyr Pro Tyr Asp Val Pro
    210                 215                 220

Asp Tyr Ala
225

<210> SEQ ID NO 93
<211> LENGTH: 450
<212> TYPE: PRT
<213> ORGANISM: Artificial Sequence
<220> FEATURE:
<223> OTHER INFORMATION: Synthetic

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Lys Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Lys Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Lys Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 94
<211> LENGTH: 219
<212> TYPE: PRT
<213> ORGANISM: Artificial Sequence
<220> FEATURE:

<223> OTHER INFORMATION: Synthetic

<400> SEQUENCE: 94

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 95
<211> LENGTH: 229
<212> TYPE: PRT
<213> ORGANISM: Artificial Sequence
<220> FEATURE:
<223> OTHER INFORMATION: Synthetic

<400> SEQUENCE: 95

```
Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser Ala Ser Thr Lys
        115                 120                 125
```

```
Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys
225

<210> SEQ ID NO 96
<211> LENGTH: 268
<212> TYPE: PRT
<213> ORGANISM: Artificial Sequence
<220> FEATURE:
<223> OTHER INFORMATION: Synthetic

<400> SEQUENCE: 96

Gly Gly Gly Ser Gly Gly Gly Gln Val Gln Leu Val Gln Ser Gly Ala
1               5                   10                  15

Glu Val Lys Lys Pro Gly Ala Ser Val Lys Val Ser Cys Lys Thr Ser
            20                  25                  30

Arg Tyr Thr Phe Thr Glu Tyr Thr Ile His Trp Val Arg Gln Ala Pro
        35                  40                  45

Gly Gln Arg Leu Glu Trp Ile Gly Gly Ile Asn Pro Asn Asn Gly Ile
    50                  55                  60

Pro Asn Tyr Asn Gln Lys Phe Lys Gly Arg Val Thr Ile Thr Val Asp
65                  70                  75                  80

Thr Ser Ala Ser Thr Ala Tyr Met Glu Leu Ser Ser Leu Arg Ser Glu
                85                  90                  95

Asp Thr Ala Val Tyr Tyr Cys Ala Arg Arg Arg Ile Ala Tyr Gly Tyr
            100                 105                 110

Asp Glu Gly His Ala Met Asp Tyr Trp Gly Gln Gly Thr Leu Val Thr
        115                 120                 125

Val Ser Ser Gly Ser Thr Ser Gly Ser Gly Lys Pro Gly Ser Gly Glu
    130                 135                 140

Gly Ser Thr Lys Gly Asp Ile Val Met Thr Gln Ser Pro Asp Ser Leu
145                 150                 155                 160

Ala Val Ser Leu Gly Glu Arg Ala Thr Ile Asn Cys Lys Ser Ser Gln
                165                 170                 175

Ser Leu Leu Tyr Ser Arg Asn Gln Lys Asn Tyr Leu Ala Trp Tyr Gln
            180                 185                 190

Gln Lys Pro Gly Gln Pro Pro Lys Leu Leu Ile Phe Trp Ala Ser Thr
        195                 200                 205

Arg Glu Ser Gly Val Pro Asp Arg Phe Ser Gly Ser Gly Phe Gly Thr
    210                 215                 220

Asp Phe Thr Leu Thr Ile Ser Ser Leu Gln Ala Glu Asp Val Ala Val
225                 230                 235                 240

Tyr Tyr Cys Gln Gln Tyr Phe Ser Tyr Pro Leu Thr Phe Gly Gln Gly
                245                 250                 255
```

Thr Lys Val Glu Ile Lys His His His His His His
            260                 265

<210> SEQ ID NO 97
<211> LENGTH: 252
<212> TYPE: PRT
<213> ORGANISM: Artificial Sequence
<220> FEATURE:
<223> OTHER INFORMATION: Synthetic

<400> SEQUENCE: 97

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Tyr Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ala
    130                 135                 140

Ser Val Lys Val Ser Cys Lys Thr Ser Arg Tyr Thr Phe Thr Glu Tyr
145                 150                 155                 160

Thr Ile His Trp Val Arg Gln Ala Pro Gly Gln Arg Leu Glu Trp Ile
                165                 170                 175

Gly Gly Ile Asn Pro Asn Asn Gly Ile Pro Asn Tyr Asn Gln Lys Phe
            180                 185                 190

Lys Gly Arg Val Thr Ile Thr Val Asp Thr Ser Ala Ser Thr Ala Tyr
        195                 200                 205

Met Glu Leu Ser Ser Leu Arg Ser Glu Asp Thr Ala Val Tyr Tyr Cys
    210                 215                 220

Ala Arg Arg Arg Ile Ala Tyr Gly Tyr Asp Glu Gly His Ala Met Asp
225                 230                 235                 240

Tyr Trp Gly Gln Gly Thr Leu Val Thr Val Ser Ser
                245                 250

<210> SEQ ID NO 98
<211> LENGTH: 232
<212> TYPE: PRT
<213> ORGANISM: Artificial Sequence
<220> FEATURE:
<223> OTHER INFORMATION: Synthetic

<400> SEQUENCE: 98

Arg Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

```
Arg Asn Gln Lys Asn Tyr Leu Ala Trp Tyr Gln Asp Lys Pro Gly Gln
            35                  40                  45

Pro Pro Lys Leu Leu Ile Phe Trp Ala Ser Thr Arg Glu Ser Gly Val
 50                  55                  60

Pro Asp Arg Phe Ser Gly Ser Gly Phe Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Phe Ser Tyr Pro Leu Thr Phe Gly Gln Gly Thr Lys Val Glu Ile
                100                 105                 110

Lys Thr Val Ala Ala Pro Ser Val Phe Ile Phe Pro Pro Ser Asp Glu
                115                 120                 125

Gln Leu Lys Ser Gly Thr Ala Ser Val Val Cys Tyr Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Trp Ser Thr Leu Thr Leu Ser Lys Ala Asp Tyr Glu
                180                 185                 190

Lys His Lys Leu Tyr Ala Cys Glu Val Thr His Gln Gly Leu Ser Ser
                195                 200                 205

Pro Val Thr Lys Ser Phe Asn Arg Gly Glu Cys Gly Gly Gly Ser Tyr
                210                 215                 220

Pro Tyr Asp Val Pro Asp Tyr Ala
225                 230

<210> SEQ ID NO 99
<211> LENGTH: 454
<212> TYPE: PRT
<213> ORGANISM: Artificial Sequence
<220> FEATURE:
<223> OTHER INFORMATION: Synthetic

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
                20                  25                  30

Thr Ile His Trp Val Arg Lys Ala Pro Gly Gln Arg Leu Glu Trp Ile
            35                  40                  45

Gly Gly Ile Asn Pro Asn Asn Gly Ile Pro Asn Tyr Asn Gln Arg Phe
 50                  55                  60

Lys Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Arg Ile Ala Tyr Gly Tyr Asp Glu Gly His Ala Met Asp
                100                 105                 110

Tyr Trp Gly Gln Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160
```

Val Thr Val Ser Trp Asn Ser Gly Ala Leu Thr Ser Gly Val Ala Thr
            165                 170                 175

Gly Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Lys Glu Leu Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Lys Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 100
<211> LENGTH: 218
<212> TYPE: PRT
<213> ORGANISM: Artificial Sequence
<220> FEATURE:
<223> OTHER INFORMATION: Synthetic

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Gly Ser Gly Thr Asp Phe Thr Leu Thr Ile
 65                  70                  75                  80

Ser Ser Leu Gln Pro Glu Asp Phe Ala Thr Tyr Tyr Cys Ala Gln Asn
                 85                  90                  95

Leu Glu Ile Pro Arg Thr Phe Gly Gln Gly Thr Lys Val Glu Leu Lys
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Leu Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 101
<211> LENGTH: 221
<212> TYPE: PRT
<213> ORGANISM: Artificial Sequence
<220> FEATURE:
<223> OTHER INFORMATION: Synthetic

<400> SEQUENCE: 101

Glu Val Gln Leu Val Gln Ser Gly Pro Gly Leu Val Gln Pro Gly Gly
 1               5                  10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
 50                  55                  60

Lys Gly Arg Phe Thr Phe Ser Leu Asp Thr Ser Ala Ser Ala Ala Tyr
 65                  70                  75                  80

Leu Gln Ile Asn Ser Leu Arg Ala Glu Asp Thr Ala Val Tyr Tyr Cys
                 85                  90                  95

Ala Arg Phe Ala Ile Lys Gly Asp Tyr Trp Gly Gln Gly Thr Leu Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys
    210                 215                 220

<210> SEQ ID NO 102
<211> LENGTH: 256
<212> TYPE: PRT
<213> ORGANISM: Artificial Sequence
<220> FEATURE:
<223> OTHER INFORMATION: Synthetic

<400> SEQUENCE: 102

Gly Gly Gly Ser Gly Gly Glu Val Gln Leu Val Gln Ser Gly Pro
1               5                   10                  15

Gly Leu Val Gln Pro Gly Gly Ser Val Arg Ile Ser Cys Ala Ala Ser
                20                  25                  30

Gly Tyr Thr Phe Thr Asn Tyr Gly Met Asn Trp Val Lys Gln Ala Pro
            35                  40                  45

Gly Lys Gly Leu Glu Trp Met Gly Trp Ile Asn Thr Tyr Thr Gly Glu
        50                  55                  60

Ser Thr Tyr Ala Asp Ser Phe Lys Gly Arg Phe Thr Phe Ser Leu Asp
65                  70                  75                  80

Thr Ser Ala Ser Ala Ala Tyr Leu Gln Ile Asn Ser Leu Arg Ala Glu
                85                  90                  95

Asp Thr Ala Val Tyr Tyr Cys Ala Arg Phe Ala Ile Lys Gly Asp Tyr
            100                 105                 110

Trp Gly Gln Gly Thr Leu Leu Thr Val Ser Ser Gly Gly Gly Gly Ser
        115                 120                 125

Gly Gly Gly Gly Ser Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ser Thr Lys Ser Leu Leu His Ser Asn Gly Ile Thr Tyr Leu
                165                 170                 175

Tyr Trp Tyr Gln Gln Lys Pro Gly Lys Ala Pro Lys Leu Leu Ile Tyr
            180                 185                 190

Gln Met Ser Asn Leu Ala Ser Gly Val Pro Ser Arg Phe Ser Ser Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Ala Gln Asn Leu Glu Ile Pro Arg Thr
225                 230                 235                 240

Phe Gly Gln Gly Thr Lys Val Glu Leu Lys His His His His His His
                245                 250                 255

<210> SEQ ID NO 103
<211> LENGTH: 254
<212> TYPE: PRT
<213> ORGANISM: Artificial Sequence
<220> FEATURE:
<223> OTHER INFORMATION: Synthetic

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
                20                  25                  30

```
Asn Gly Ile Thr Tyr Leu Tyr Trp Tyr Gln Gln Lys Pro Gly Lys Ala
            35                  40                  45
Pro Lys Leu Leu Ile Tyr Gln Met Ser Asn Leu Ala Ser Gly Val Pro
 50                  55                  60
Ser Arg Phe Ser Ser Ser Gly Ser Gly Thr Asp Phe Thr Leu Thr Ile
 65                  70                  75                  80
Ser Ser Leu Gln Pro Glu Asp Phe Ala Thr Tyr Tyr Cys Ala Gln Asn
                 85                  90                  95
Leu Glu Ile Pro Arg Thr Phe Gly Gln Gly Thr Lys Val Glu Leu Lys
            100                 105                 110
Arg Ala Thr Pro Ser His Asn Ser His Gln Val Pro Ser Ala Gly Gly
            115                 120                 125
Pro Thr Ala Asn Ser Gly Thr Ser Gly Ser Glu Val Gln Leu Val Gln
130                 135                 140
Ser Gly Pro Gly Leu Val Gln Pro Gly Gly Ser Val Arg Ile Ser Cys
145                 150                 155                 160
Ala Ala Ser Gly Tyr Thr Phe Thr Asn Tyr Gly Met Asn Trp Val Lys
                165                 170                 175
Gln Ala Pro Gly Lys Gly Leu Glu Trp Met Gly Trp Ile Asn Thr Tyr
            180                 185                 190
Thr Gly Glu Ser Thr Tyr Ala Asp Ser Phe Lys Gly Arg Phe Thr Phe
            195                 200                 205
Ser Leu Asp Thr Ser Ala Ser Ala Ala Tyr Leu Gln Ile Asn Ser Leu
        210                 215                 220
Arg Ala Glu Asp Thr Ala Val Tyr Tyr Cys Ala Arg Phe Ala Ile Lys
225                 230                 235                 240
Gly Asp Tyr Trp Gly Gln Gly Thr Leu Leu Thr Val Ser Ser
                245                 250

<210> SEQ ID NO 104
<211> LENGTH: 231
<212> TYPE: PRT
<213> ORGANISM: Artificial Sequence
<220> FEATURE:
<223> OTHER INFORMATION: Synthetic

<400> SEQUENCE: 104

Arg Ile Gln Met Thr Gln Ser Pro Ser Ser Leu Ser Ala Ser Val Gly
  1               5                  10                  15
Asp Arg Val Thr Ile Thr Cys Arg Ser Thr Lys Ser Leu Leu His Ser
             20                  25                  30
Asn Gly Ile Thr Tyr Leu Tyr Trp Tyr Gln Asp Lys Pro Gly Lys Ala
            35                  40                  45
Pro Lys Leu Leu Ile Tyr Gln Met Ser Asn Leu Ala Ser Gly Val Pro
 50                  55                  60
Ser Arg Phe Ser Ser Ser Gly Ser Gly Thr Asp Phe Thr Leu Thr Ile
 65                  70                  75                  80
Ser Ser Leu Gln Pro Glu Asp Phe Ala Thr Tyr Tyr Cys Ala Gln Asn
                 85                  90                  95
Leu Glu Ile Pro Arg Thr Phe Gly Gln Gly Thr Lys Val Glu Leu Lys
            100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Tyr Leu Asn Asn Phe Tyr
        130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Trp Ser Thr Leu Thr Leu Ser Lys Ala Asp Tyr Glu Lys
        180                 185                 190

His Lys Leu Tyr Ala Cys Glu Val Thr His Gln Gly Leu Ser Ser Pro
    195                 200                 205

Val Thr Lys Ser Phe Asn Arg Gly Glu Cys Gly Gly Ser Tyr Pro
210                 215                 220

Tyr Asp Val Pro Asp Tyr Ala
225                 230

<210> SEQ ID NO 105
<211> LENGTH: 446
<212> TYPE: PRT
<213> ORGANISM: Artificial Sequence
<220> FEATURE:
<223> OTHER INFORMATION: Synthetic

<400> SEQUENCE: 105

Glu Val Gln Leu Val Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Lys Ala Pro Gly Lys Gly Leu Glu Trp Met
        35                  40                  45

Gly Trp Ile Asn Thr Tyr Thr Gly Glu Ser Thr Tyr Ala Asp Ser Phe
50                  55                  60

Lys Gly Glu Phe Thr Phe Ser Leu Asp Thr Ser Ala Ser Ala Ala Tyr
65                  70                  75                  80

Leu Gln Ile Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val Ala Thr Gly Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
                275                 280                 285

Lys Pro Arg Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Lys Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Lys Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 106
<211> LENGTH: 213
<212> TYPE: PRT
<213> ORGANISM: Artificial Sequence
<220> FEATURE:
<223> OTHER INFORMATION: Synthetic

<400> SEQUENCE: 106

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
                20                  25                  30

Leu Asn Trp Tyr Gln Gln Lys Pro Gly Gln Pro Pro Lys Leu Leu Ile
            35                  40                  45

Tyr Trp Ala Ser Thr Arg Glu Ser Gly Val Pro Asp Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Leu Tyr Ala
                180                 185                 190
```

Cys Glu Val Thr His Gln Gly Leu Ser Ser Pro Val Thr Lys Ser Phe
            195                 200                 205

Asn Arg Gly Glu Cys
    210

<210> SEQ ID NO 107
<211> LENGTH: 232
<212> TYPE: PRT
<213> ORGANISM: Artificial Sequence
<220> FEATURE:
<223> OTHER INFORMATION: Synthetic

<400> SEQUENCE: 107

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Gly Trp Gly Ser Gly Trp Arg Pro Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys
225                 230

<210> SEQ ID NO 108
<211> LENGTH: 262
<212> TYPE: PRT
<213> ORGANISM: Artificial Sequence
<220> FEATURE:
<223> OTHER INFORMATION: Synthetic

<400> SEQUENCE: 108

Gly Gly Gly Ser Gly Gly Gly Glu Val Gln Leu Leu Glu Ser Gly Gly
1               5                   10                  15

Gly Val Val Gln Pro Gly Arg Ser Leu Arg Leu Ser Cys Ala Ala Ser
            20                  25                  30

Gly Phe Thr Phe Ser Ser Tyr Gly Met His Trp Val Arg Gln Ala Pro
            35                  40                  45

Gly Lys Gly Leu Glu Trp Val Ala Val Ile Ser Tyr Asp Gly Ser Asn
 50                  55                  60

Lys Tyr Tyr Ala Asp Ser Val Lys Gly Arg Phe Thr Ile Ser Arg Asp
 65                  70                  75                  80

Asn Ser Lys Asn Thr Leu Tyr Leu Gln Met Asn Ser Leu Arg Ala Glu
                 85                  90                  95

Asp Thr Ala Val Tyr Tyr Cys Ala Lys Asp Met Gly Trp Gly Ser Gly
            100                 105                 110

Trp Arg Pro Tyr Tyr Tyr Gly Met Asp Val Trp Gly Gln Gly Thr
            115                 120                 125

Thr Val Thr Val Ser Ser Gly Gly Gly Ser Gly Gly Gly Gly Ser
    130                 135                 140

Gly Gly Gly Gly Ser Glu Leu Gln Met Thr Gln Ser Pro Ser Ser Leu
145                 150                 155                 160

Ser Ala Ser Val Gly Asp Arg Val Thr Ile Thr Cys Arg Thr Ser Gln
                165                 170                 175

Ser Ile Ser Ser Tyr Leu Asn Trp Tyr Gln Gln Lys Pro Gly Gln Pro
            180                 185                 190

Pro Lys Leu Leu Ile Tyr Trp Ala Ser Thr Arg Glu Ser Gly Val Pro
            195                 200                 205

Asp Arg Phe Ser Gly Ser Gly Ser Gly Thr Asp Phe Thr Leu Thr Ile
            210                 215                 220

Ser Ser Leu Gln Pro Glu Asp Ser Ala Thr Tyr Tyr Cys Gln Gln Ser
225                 230                 235                 240

Tyr Asp Ile Pro Tyr Thr Phe Gly Gln Gly Thr Lys Leu Glu Ile Lys
                245                 250                 255

His His His His His His
            260

<210> SEQ ID NO 109
<211> LENGTH: 249
<212> TYPE: PRT
<213> ORGANISM: Artificial Sequence
<220> FEATURE:
<223> OTHER INFORMATION: Synthetic

<400> SEQUENCE: 109

Glu Leu Gln Met Thr Gln Ser Pro Ser Ser Leu Ser Ala Ser Val Gly
1               5                  10                  15

Asp Arg Val Thr Ile Thr Cys Arg Thr Ser Gln Ser Ile Ser Ser Tyr
             20                  25                  30

Leu Asn Trp Tyr Gln Gln Lys Pro Gly Gln Pro Pro Lys Leu Leu Ile
            35                  40                  45

Tyr Trp Ala Ser Thr Arg Glu Ser Gly Val Pro Asp Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ser Ala Thr Tyr Tyr Cys Gln Gln Ser Tyr Asp Ile Pro Tyr
                 85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Glu Val Gln Leu Leu Glu
            115                 120                 125

```
Ser Gly Gly Gly Val Val Gln Pro Gly Arg Ser Leu Arg Leu Ser Cys
    130                 135                 140
Ala Ala Ser Gly Phe Thr Phe Ser Ser Tyr Gly Met His Trp Val Arg
145                 150                 155                 160
Gln Ala Pro Gly Lys Gly Leu Glu Trp Val Ala Val Ile Ser Tyr Asp
                165                 170                 175
Gly Ser Asn Lys Tyr Tyr Ala Asp Ser Val Lys Gly Arg Phe Thr Ile
            180                 185                 190
Ser Arg Asp Asn Ser Lys Asn Thr Leu Tyr Leu Gln Met Asn Ser Leu
        195                 200                 205
Arg Ala Glu Asp Thr Ala Val Tyr Tyr Cys Ala Lys Asp Met Gly Trp
    210                 215                 220
Gly Ser Gly Trp Arg Pro Tyr Tyr Tyr Gly Met Asp Val Trp Gly
225                 230                 235                 240
Gln Gly Thr Thr Val Thr Val Ser Ser
                245
```

<210> SEQ ID NO 110
<211> LENGTH: 226
<212> TYPE: PRT
<213> ORGANISM: Artificial Sequence
<220> FEATURE:
<223> OTHER INFORMATION: Synthetic

<400> SEQUENCE: 110

```
Arg Leu Gln Met Thr Gln Ser Pro Ser Ser Leu Ser Ala Ser Val Gly
1               5                   10                  15
Asp Arg Val Thr Ile Thr Cys Arg Thr Ser Gln Ser Ile Ser Ser Tyr
                20                  25                  30
Leu Asn Trp Tyr Gln Asp Lys Pro Gly Gln Pro Pro Lys Leu Leu Ile
            35                  40                  45
Tyr Trp Ala Ser Thr Arg Glu Ser Gly Val Pro Asp Arg Phe Ser Gly
        50                  55                  60
Ser Gly Ser Gly Thr Asp Phe Thr Leu Thr Ile Ser Ser Leu Gln Pro
65                  70                  75                  80
Glu Asp Ser Ala Thr Tyr Tyr Cys Gln Gln Ser Tyr Asp Ile Pro Tyr
                85                  90                  95
Thr Phe Gly Gln Gly Thr Lys Leu Glu Ile Lys Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Tyr Leu Asn Asn Phe Tyr Pro Arg Glu Ala Lys
130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Trp Ser
                165                 170                 175
Thr Leu Thr Leu Ser Lys Ala Asp Tyr Glu Lys His Lys Leu Tyr Ala
            180                 185                 190
Cys Glu Val Thr His Gln Gly Leu Ser Ser Pro Val Thr Lys Ser Phe
        195                 200                 205
Asn Arg Gly Glu Cys Gly Gly Gly Ser Tyr Pro Tyr Asp Val Pro Asp
    210                 215                 220
Tyr Ala
225
```

<210> SEQ ID NO 111
<211> LENGTH: 457
<212> TYPE: PRT
<213> ORGANISM: Artificial Sequence
<220> FEATURE:
<223> OTHER INFORMATION: Synthetic

<400> SEQUENCE: 111

```
Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Lys Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Glu Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Gly Trp Gly Ser Gly Trp Arg Pro Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val Ala Thr Gly Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Lys Glu Leu
        355                 360                 365
```

```
Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Lys Ser Asp Gly Ser Phe Phe Leu
                405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
        435                 440                 445

Lys Ser Leu Ser Leu Ser Pro Gly Lys
        450                 455

<210> SEQ ID NO 112
<211> LENGTH: 215
<212> TYPE: PRT
<213> ORGANISM: Artificial Sequence
<220> FEATURE:
<223> OTHER INFORMATION: Synthetic

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Thr Val Ser Ala Asn
            20                  25                  30

Val Ala Trp Tyr Gln Gln Lys Pro Gly Lys Ala Pro Lys Leu Leu Ile
        35                  40                  45

Tyr Leu Ala Ser Tyr Arg Tyr Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 113
<211> LENGTH: 226
<212> TYPE: PRT
<213> ORGANISM: Artificial Sequence
<220> FEATURE:
<223> OTHER INFORMATION: Synthetic
```

<400> SEQUENCE: 113

```
Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Glu Tyr
            20                  25                  30
Gly Met Asn Val Trp Arg Gln Ala Pro Gly Gln Gly Leu Glu Trp Met
        35                  40                  45
Gly Trp Ile Asn Thr Lys Ser Gly Glu Ala Thr Tyr Val Glu Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Trp Asp Phe Tyr Asp Tyr Val Asp Glu Ala Met Tyr Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys
225
```

<210> SEQ ID NO 114
<211> LENGTH: 258
<212> TYPE: PRT
<213> ORGANISM: Artificial Sequence
<220> FEATURE:
<223> OTHER INFORMATION: Synthetic

<400> SEQUENCE: 114

```
Gly Gly Gly Ser Gly Gly Gly Gln Val Gln Leu Val Gln Ser Gly Ser
1               5                   10                  15
Glu Leu Lys Lys Pro Gly Ala Ser Val Lys Val Ser Cys Lys Ala Ser
            20                  25                  30
Gly Tyr Thr Phe Thr Glu Tyr Gly Met Asn Val Trp Arg Gln Ala Pro
        35                  40                  45
Gly Gln Gly Leu Glu Trp Met Gly Trp Ile Asn Thr Lys Ser Gly Glu
    50                  55                  60
Ala Thr Tyr Val Glu Glu Phe Lys Gly Arg Phe Val Phe Ser Leu Asp
65                  70                  75                  80
Thr Ser Val Ser Thr Ala Tyr Leu Gln Ile Ser Ser Leu Lys Ala Glu
                85                  90                  95
Asp Thr Ala Val Tyr Tyr Cys Ala Arg Trp Asp Phe Tyr Asp Tyr Val
            100                 105                 110
```

```
Asp Glu Ala Met Tyr Trp Gly Gln Gly Thr Thr Val Thr Val Ser Ser
            115                 120                 125

Gly Gly Gly Gly Ser Gly Gly Gly Gly Ser Gly Gly Gly Gly Ser Asp
            130                 135                 140

Ile Gln Met Thr Gln Ser Pro Ser Ser Leu Ser Ala Ser Val Gly Asp
145                 150                 155                 160

Arg Val Thr Ile Thr Cys Lys Ala Ser Gln Thr Val Ser Ala Asn Val
                165                 170                 175

Ala Trp Tyr Gln Gln Lys Pro Gly Lys Ala Pro Lys Leu Leu Ile Tyr
            180                 185                 190

Leu Ala Ser Tyr Arg Tyr Arg Gly Val Pro Ser Arg Phe Ser Gly Ser
            195                 200                 205

Gly Ser Gly Thr Asp Phe Thr Leu Thr Ile Ser Ser Leu Gln Pro Glu
            210                 215                 220

Asp Phe Ala Thr Tyr Tyr Cys His Gln Tyr Tyr Thr Tyr Pro Leu Phe
225                 230                 235                 240

Thr Phe Gly Gln Gly Thr Lys Leu Glu Ile Lys Arg His His His His
                245                 250                 255

His His

<210> SEQ ID NO 115
<211> LENGTH: 245
<212> TYPE: PRT
<213> ORGANISM: Artificial Sequence
<220> FEATURE:
<223> OTHER INFORMATION: Synthetic

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Thr Val Ser Ala Asn
            20                  25                  30

Val Ala Trp Tyr Gln Gln Lys Pro Gly Lys Ala Pro Lys Leu Leu Ile
        35                  40                  45

Tyr Leu Ala Ser Tyr Arg Tyr Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Gly Gly Gly
            100                 105                 110

Gly Ser Gly Gly Gly Gly Ser Gly Gly Gly Gly Ser Gln Val Gln Leu
        115                 120                 125

Val Gln Ser Gly Ser Glu Leu Lys Lys Pro Gly Ala Ser Val Lys Val
    130                 135                 140

Ser Cys Lys Ala Ser Gly Tyr Thr Phe Thr Glu Tyr Gly Met Asn Val
145                 150                 155                 160

Trp Arg Gln Ala Pro Gly Gln Gly Leu Glu Trp Met Gly Trp Ile Asn
                165                 170                 175

Thr Lys Ser Gly Glu Ala Thr Tyr Val Glu Glu Phe Lys Gly Arg Phe
            180                 185                 190

Val Phe Ser Leu Asp Thr Ser Val Ser Thr Ala Tyr Leu Gln Ile Ser
        195                 200                 205
```

```
Ser Leu Lys Ala Glu Asp Thr Ala Val Tyr Tyr Cys Ala Arg Trp Asp
    210                 215                 220
Phe Tyr Asp Tyr Val Asp Glu Ala Met Tyr Trp Gly Gln Gly Thr Thr
225                 230                 235                 240
Val Thr Val Ser Ser
            245
```

<210> SEQ ID NO 116
<211> LENGTH: 228
<212> TYPE: PRT
<213> ORGANISM: Artificial Sequence
<220> FEATURE:
<223> OTHER INFORMATION: Synthetic

<400> SEQUENCE: 116

```
Arg Ile Gln Met Thr Gln Ser Pro Ser Ser Leu Ser Ala Ser Val Gly
1               5                   10                  15
Asp Arg Val Thr Ile Thr Cys Lys Ala Ser Gln Thr Val Ser Ala Asn
                20                  25                  30
Val Ala Trp Tyr Gln Asp Lys Pro Gly Lys Ala Pro Lys Leu Leu Ile
            35                  40                  45
Tyr Leu Ala Ser Tyr Arg Tyr Arg Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys His Gln Tyr Tyr Thr Tyr Pro Leu
                85                  90                  95
Phe Thr Phe Gly Gln Gly Thr Lys Leu Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Tyr Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Trp Ser Thr Leu Thr Leu Ser Lys Ala Asp Tyr Glu Lys His Lys Leu
            180                 185                 190
Tyr Ala Cys Glu Val Thr His Gln Gly Leu Ser Ser Pro Val Thr Lys
        195                 200                 205
Ser Phe Asn Arg Gly Glu Cys Gly Gly Gly Ser Tyr Pro Tyr Asp Val
    210                 215                 220
Pro Asp Tyr Ala
225
```

<210> SEQ ID NO 117
<211> LENGTH: 451
<212> TYPE: PRT
<213> ORGANISM: Artificial Sequence
<220> FEATURE:
<223> OTHER INFORMATION: Synthetic

<400> SEQUENCE: 117

```
Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Glu Tyr
                20                  25                  30
```

```
Gly Met Asn Val Trp Arg Lys Ala Pro Gly Gln Gly Leu Glu Trp Met
         35                  40                  45
Gly Trp Ile Asn Thr Lys Ser Gly Glu Ala Thr Tyr Val Glu Glu Phe
 50                  55                  60
Lys Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                 85                  90                  95
Ala Arg Trp Asp Phe Tyr Asp Tyr Val Asp Glu Ala Met Tyr Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val Ala Thr Gly Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Lys Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Lys Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

Pro Gly Lys
    450

<210> SEQ ID NO 118
<211> LENGTH: 217
<212> TYPE: PRT
<213> ORGANISM: Artificial Sequence
<220> FEATURE:
<223> OTHER INFORMATION: Synthetic

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Ser
            20                  25                  30

Tyr Leu Ser Trp Tyr Gln Gln Lys Pro Gly Lys Ala Pro Lys Leu Leu
        35                  40                  45

Ile Tyr Ala Val Ser Tyr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Ser Gly Tyr Tyr Ser Ala
                85                  90                  95

Gly Asp Leu Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 119
<211> LENGTH: 220
<212> TYPE: PRT
<213> ORGANISM: Artificial Sequence
<220> FEATURE:
<223> OTHER INFORMATION: Synthetic

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Ile Asn Trp Val Arg Gln Ala Pro Gly Lys Gly Leu Glu Trp Val
        35                  40                  45

Ala Ile Ile Phe Cys Ala Gly Asn Ala Tyr Asn Ala Ser Trp Ala Lys
    50                  55                  60

Gly Arg Phe Thr Ile Ser Arg Asp Asp Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Trp Gln Ala Leu Val Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys
    210                 215                 220

<210> SEQ ID NO 120
<211> LENGTH: 254
<212> TYPE: PRT
<213> ORGANISM: Artificial Sequence
<220> FEATURE:
<223> OTHER INFORMATION: Synthetic

<400> SEQUENCE: 120

Gly Gly Gly Ser Gly Gly Gly Glu Val Gln Leu Val Glu Ser Gly Gly
1               5                   10                  15

Gly Leu Val Gln Pro Gly Gly Ser Leu Arg Leu Ser Cys Ala Ala Ser
            20                  25                  30

Gly Phe Ser Leu Ser Asn Tyr Tyr Ile Asn Trp Val Arg Gln Ala Pro
        35                  40                  45

Gly Lys Gly Leu Glu Trp Val Ala Ile Ile Phe Cys Ala Gly Asn Ala
    50                  55                  60

Tyr Asn Ala Ser Trp Ala Lys Gly Arg Phe Thr Ile Ser Arg Asp Asp
65                  70                  75                  80

Ser Lys Asn Thr Leu Tyr Leu Gln Met Asn Ser Leu Arg Ala Glu Asp
                85                  90                  95

Thr Ala Val Tyr Tyr Cys Ala Arg Gly Trp Gln Ala Leu Val Asn Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Gln Ala Ser Gln Ser Ile Ser Ser Tyr Leu Ser Trp Tyr Gln Gln
                165                 170                 175

Lys Pro Gly Lys Ala Pro Lys Leu Leu Ile Tyr Ala Val Ser Tyr Leu
            180                 185                 190

Ala Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

```
Tyr Cys Gln Ser Gly Tyr Tyr Ser Ala Gly Asp Leu Thr Phe Gly Gln
225                 230                 235                 240

Gly Thr Lys Val Glu Ile Lys Arg His His His His His His
                245                 250
```

<210> SEQ ID NO 121
<211> LENGTH: 241
<212> TYPE: PRT
<213> ORGANISM: Artificial Sequence
<220> FEATURE:
<223> OTHER INFORMATION: Synthetic

<400> SEQUENCE: 121

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Ser
            20                  25                  30

Tyr Leu Ser Trp Tyr Gln Gln Lys Pro Gly Lys Ala Pro Lys Leu Leu
        35                  40                  45

Ile Tyr Ala Val Ser Tyr Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Ser Gly Tyr Tyr Ser Ala
                85                  90                  95

Gly Asp Leu Thr Phe Gly Gln Gly Thr Lys Val Glu Ile Lys Arg Gly
            100                 105                 110

Gly Gly Gly Ser Gly Gly Gly Gly Ser Gly Gly Gly Gly Ser Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Ser Leu Ser Asn Tyr Tyr Ile
145                 150                 155                 160

Asn Trp Val Arg Gln Ala Pro Gly Lys Gly Leu Glu Trp Val Ala Ile
                165                 170                 175

Ile Phe Cys Ala Gly Asn Ala Tyr Asn Ala Ser Trp Ala Lys Gly Arg
            180                 185                 190

Phe Thr Ile Ser Arg Asp Asp Ser Lys Asn Thr Leu Tyr Leu Gln Met
        195                 200                 205

Asn Ser Leu Arg Ala Glu Asp Thr Ala Val Tyr Tyr Cys Ala Arg Gly
    210                 215                 220

Trp Gln Ala Leu Val Asn Trp Gly Gln Gly Thr Leu Val Thr Val Ser
225                 230                 235                 240

Ser
```

<210> SEQ ID NO 122
<211> LENGTH: 230
<212> TYPE: PRT
<213> ORGANISM: Artificial Sequence
<220> FEATURE:
<223> OTHER INFORMATION: Synthetic

<400> SEQUENCE: 122

```
Arg Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Ser
            20                  25                  30
```

```
Tyr Leu Ser Trp Tyr Gln Asp Lys Pro Gly Lys Ala Pro Lys Leu Leu
        35                  40                  45

Ile Tyr Ala Val Ser Tyr Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Ser Gly Tyr Tyr Ser Ala
                 85                  90                  95

Gly Asp Leu Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Trp Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys Gly Gly Ser Tyr Pro Tyr
210                 215                 220

Asp Val Pro Asp Tyr Ala
225                 230

<210> SEQ ID NO 123
<211> LENGTH: 445
<212> TYPE: PRT
<213> ORGANISM: Artificial Sequence
<220> FEATURE:
<223> OTHER INFORMATION: Synthetic

<400> SEQUENCE: 123

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Asn Tyr
            20                  25                  30

Tyr Ile Asn Trp Val Arg Lys Ala Pro Gly Lys Gly Leu Glu Trp Val
        35                  40                  45

Ala Ile Ile Phe Cys Ala Gly Asn Ala Tyr Asn Ala Ser Trp Ala Lys
 50                  55                  60

Gly Glu Phe Thr Ile Ser Arg Asp Asp Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Trp Gln Ala Leu Val Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160
```

```
Leu Thr Ser Gly Val Ala Thr Gly Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Lys Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Lys Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 124
<211> LENGTH: 119
<212> TYPE: PRT
<213> ORGANISM: Artificial Sequence
<220> FEATURE:
<223> OTHER INFORMATION: Synthetic

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Ser Tyr Ala Gln Lys Phe
    50                  55                  60

Gln Gly Arg Val Thr Met Thr Thr Asp Lys Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 125
<211> LENGTH: 5
<212> TYPE: PRT
<213> ORGANISM: Artificial Sequence
<220> FEATURE:
<223> OTHER INFORMATION: Synthetic

<400> SEQUENCE: 125

Arg Tyr Thr Met His
1               5

<210> SEQ ID NO 126
<211> LENGTH: 17
<212> TYPE: PRT
<213> ORGANISM: Artificial Sequence
<220> FEATURE:
<223> OTHER INFORMATION: Synthetic

<400> SEQUENCE: 126

Tyr Ile Asn Pro Ser Arg Gly Tyr Thr Ser Tyr Ala Gln Lys Phe Gln
1               5                   10                  15

Gly

<210> SEQ ID NO 127
<211> LENGTH: 10
<212> TYPE: PRT
<213> ORGANISM: Artificial Sequence
<220> FEATURE:
<223> OTHER INFORMATION: Synthetic

<400> SEQUENCE: 127

Tyr Tyr Asp Asp His Tyr Cys Leu Asp Tyr
1               5                   10

<210> SEQ ID NO 128
<211> LENGTH: 107
<212> TYPE: PRT
<213> ORGANISM: Artificial Sequence
<220> FEATURE:
<223> OTHER INFORMATION: Synthetic

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

Asn Trp Tyr Gln Gln Lys Pro Gly Lys Ala Pro Lys Leu Leu Ile Tyr
        35                  40                  45

Asp Thr Ser Lys Val Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95
```

Phe Gly Gly Gly Thr Lys Val Glu Ile Lys Arg
            100                 105

<210> SEQ ID NO 129
<211> LENGTH: 10
<212> TYPE: PRT
<213> ORGANISM: Artificial Sequence
<220> FEATURE:
<223> OTHER INFORMATION: Synthetic

<400> SEQUENCE: 129

Arg Ala Ser Ser Ser Val Ser Tyr Met Asn
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Synthetic

<400> SEQUENCE: 130

Asp Thr Ser Lys Val Ala Ser
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Gln Gln Trp Ser Ser Asn Pro Leu Thr
1               5

<210> SEQ ID NO 132
<211> LENGTH: 774
<212> TYPE: DNA
<213> ORGANISM: Artificial Sequence
<220> FEATURE:
<223> OTHER INFORMATION: Synthetic

<400> SEQUENCE: 132

```
ggtggcggct caggtggagg ccaggtgcag ctggtgcaga gcggcgcgga agtgaaaaaa    60
ccgggcgcga gcgtgaaagt gagctgcaaa gcgagcggct ataccttac ccgctatacc    120
atgcattggg tgcgccaggc gccgggccag ggcctggaat ggatgggcta tattaacccg    180
agccgcggct ataccagcta tgcgcagaaa tttcagggcc gcgtgaccat gaccaccgat    240
aaaagcacca gcaccgtgta tatggaactg agcagcctgc gcagcgaaga taccgcggtg    300
tattattgcg cgcgctatta tgatgatcat tattgcctgg attattgggg ccagggcacc    360
accgtgaccg tgagcagcgt ggagggcggc agcggcggca gcggcggcag cggcggcagc    420
ggcggcgtgg acgatattca gatgacccag agcccgagca gcctgagcgc gagcgtgggc    480
gatcgcgtga ccattacctg ccgcgcgagc agcagcgtga gctatatgaa ctggtatcag    540
cagaaaccgg gcaaagcgcc gaaactgctg atttatgata ccagcaaagt ggcgagcggc    600
gtgccgagcc gctttagcgg cagcggcagc ggcaccgatt atacctgac cattagcagc    660
ctgcagccgg aagattttgc gacctattat tgccagcagt ggagcagcaa cccgctgacc    720
tttggcggcg gcaccaaagt ggaaattaaa cgccaccacc accaccacca ctga          774
```

-continued

<210> SEQ ID NO 133
<211> LENGTH: 257
<212> TYPE: PRT
<213> ORGANISM: Artificial Sequence
<220> FEATURE:
<223> OTHER INFORMATION: Synthetic

<400> SEQUENCE: 133

```
Gly Gly Gly Ser Gly Gly Gly Gln Val Gln Leu Val Gln Ser Gly Ala
1               5                   10                  15

Glu Val Lys Lys Pro Gly Ala Ser Val Lys Val Ser Cys Lys Ala Ser
            20                  25                  30

Gly Tyr Thr Phe Thr Arg Tyr Thr Met His Trp Val Arg Gln Ala Pro
        35                  40                  45

Gly Gln Gly Leu Glu Trp Met Gly Tyr Ile Asn Pro Ser Arg Gly Tyr
    50                  55                  60

Thr Ser Tyr Ala Gln Lys Phe Gln Gly Arg Val Thr Met Thr Thr Asp
65                  70                  75                  80

Lys Ser Thr Ser Thr Val Tyr Met Glu Leu Ser Ser Leu Arg Ser Glu
                85                  90                  95

Asp Thr Ala Val Tyr Tyr Cys Ala Arg Tyr Tyr Asp Asp His Tyr Cys
            100                 105                 110

Leu Asp Tyr Trp Gly Gln Gly Thr Thr Val Thr Val Ser Ser Val Glu
        115                 120                 125

Gly Gly Ser Gly Gly Ser Gly Gly Ser Gly Gly Ser Gly Gly Val Asp
    130                 135                 140

Asp Ile Gln Met Thr Gln Ser Pro Ser Ser Leu Ser Ala Ser Val Gly
145                 150                 155                 160

Asp Arg Val Thr Ile Thr Cys Arg Ala Ser Ser Ser Val Ser Tyr Met
                165                 170                 175

Asn Trp Tyr Gln Gln Lys Pro Gly Lys Ala Pro Lys Leu Leu Ile Tyr
            180                 185                 190

Asp Thr Ser Lys Val Ala Ser Gly Val Pro Ser Arg Phe Ser Gly Ser
        195                 200                 205

Gly Ser Gly Thr Asp Tyr Thr Leu Thr Ile Ser Ser Leu Gln Pro Glu
    210                 215                 220

Asp Phe Ala Thr Tyr Tyr Cys Gln Gln Trp Ser Ser Asn Pro Leu Thr
225                 230                 235                 240

Phe Gly Gly Gly Thr Lys Val Glu Ile Lys Arg His His His His His
                245                 250                 255

His
```

<210> SEQ ID NO 134
<211> LENGTH: 642
<212> TYPE: DNA
<213> ORGANISM: Artificial Sequence
<220> FEATURE:
<223> OTHER INFORMATION: Synthetic

<400> SEQUENCE: 134

```
gatattcaga tgacccagag cccgagcagc ctgagcgcga gcgtgggcga tcgcgtgacc      60
attacctgcc gcgcgagcag cagcgtgagc tatatgaact ggtatcagca gaaaccgggc     120
aaagcgccga aactgctgat ttatgatacc agcaaagtgg cgagcggcgt gccgagccgc     180
tttagcggca gcggcagcgg caccgattat accctgacca ttagcagcct gcagccggaa     240
gattttgcga cctattattg ccagcagtgg agcagcaacc cgctgacctt tggcggcggc     300
```

```
accaaagtgg aaattaaacg cactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag     480
agtgtcacag agcaggacag caaggacagc acctacagcc tcagcagcac cctgacgctg    540
agcaaagcag actacgagaa acacaaactc tacgcctgcg aagtcaccca tcagggcctg    600
agctcgcccg tcacaaagag cttcaacagg ggagagtgct ga                      642
```

```
<210> SEQ ID NO 135
<211> LENGTH: 213
<212> TYPE: PRT
<213> ORGANISM: Artificial Sequence
<220> FEATURE:
<223> OTHER INFORMATION: Synthetic

<400> SEQUENCE: 135
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

Asn Trp Tyr Gln Gln Lys Pro Gly Lys Ala Pro Lys Leu Leu Ile Tyr
        35                  40                  45

Asp Thr Ser Lys Val Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Leu Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

```
<210> SEQ ID NO 136
<211> LENGTH: 651
<212> TYPE: DNA
<213> ORGANISM: Artificial Sequence
<220> FEATURE:
<223> OTHER INFORMATION: Synthetic

<400> SEQUENCE: 136
```

```
caggtgcagc tggtgcagag cggcgcggaa gtgaaaaaac cgggcgcgag cgtgaaagtg     60
agctgcaaag cgagcggcta cctttacc cgctatacca tgcattgggt gcgccaggcg     120
ccgggccagg gcctggaatg gatgggctat attaacccga gccgcggcta taccagctat    180
```

```
gcgcagaaat tcagggccg cgtgaccatg accaccgata aaagcaccag caccgtgtat      240
atggaactga gcagcctgcg cagcgaagat accgcggtgt attattgcgc gcgctattat      300
gatgatcatt attgcctgga ttattggggc cagggcacca ccgtgaccgt gagcagcgcc      360
tccaccaaag gtccatcggt cttccccctg gcgccctgct ccaggagcac ctccgagagc      420
acagcggccc tgggctgcct ggtcaaggac tacttccccg aaccggtgac ggtgtcgtgg      480
aactcaggcg ctctgaccag cggcgtgcac accttcccag ctgtcctaca gtcctcagga      540
ctctactccc tcagcagcgt ggtgaccgtg ccctccagca acttcggcac ccagacctac      600
acctgcaacg tagatcacaa gcccagtaac accaaggtgg acaagacagt t              651
```

```
<210> SEQ ID NO 137
<211> LENGTH: 217
<212> TYPE: PRT
<213> ORGANISM: Artificial Sequence
<220> FEATURE:
<223> OTHER INFORMATION: Synthetic

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Ser Tyr Ala Gln Lys Phe
    50                  55                  60

Gln Gly Arg Val Thr Met Thr Thr Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val
    210                 215

<210> SEQ ID NO 138
<211> LENGTH: 765
<212> TYPE: DNA
<213> ORGANISM: Artificial Sequence
<220> FEATURE:
<223> OTHER INFORMATION: Synthetic
```

<400> SEQUENCE: 138

```
ggcggtggat cacaggtgca gctggtgcag agcggcgcgg aagtgaaaaa accgggcgcg    60
agcgtgaaag tgagctgcaa agcgagcggc tataccttta cccgctatac catgcattgg   120
gtgcgccagg cgccgggcca gggcctggaa tggatgggct atattaaccc gagccgcggc   180
tataccagct atgcgcagaa atttcagggc cgcgtgacca tgaccaccga taaaagcacc   240
agcaccgtgt atatggaact gagcagcctg cgcagcgaag ataccgcggt gtattattgc   300
gcgcgctatt atgatgatca ttattgcctg gattattggg gccagggcac caccgtgacc   360
gtgagcagcg tggagggcgg cagcggcggc agcggcggca gcggcggcag cggcggcgtg   420
gacgatattc agatgaccca gagcccgagc agcctgagcg cgagcgtggg cgatcgcgtg   480
accattaccc gccgcgcgag cagcagcgtg agctatatga actggtatca gcagaaaccg   540
ggcaaagcgc cgaaactgct gatttatgat accagcaaag tggcgagcgg cgtgccgagc   600
cgctttagcg gcagcggcag cggcaccgat tataccctga ccattagcag cctgcagccg   660
gaagattttg cgacctatta ttgccagcag tggagcagca acccgctgac ctttggcggc   720
ggcaccaaag tggaaattaa acgccaccac caccaccacc actga                  765
```

<210> SEQ ID NO 139
<211> LENGTH: 254
<212> TYPE: PRT
<213> ORGANISM: Artificial Sequence
<220> FEATURE:
<223> OTHER INFORMATION: Synthetic

<400> SEQUENCE: 139

```
Gly Gly Gly Ser Gln Val Gln Leu Val Gln Ser Gly Ala Glu Val Lys
  1               5                  10                  15
Lys Pro Gly Ala Ser Val Lys Val Ser Cys Lys Ala Ser Gly Tyr Thr
             20                  25                  30
Phe Thr Arg Tyr Thr Met His Trp Val Arg Gln Ala Pro Gly Gln Gly
         35                  40                  45
Leu Glu Trp Met Gly Tyr Ile Asn Pro Ser Arg Gly Tyr Thr Ser Tyr
     50                  55                  60
Ala Gln Lys Phe Gln Gly Arg Val Thr Met Thr Thr Asp Lys Ser Thr
 65                  70                  75                  80
Ser Thr Val Tyr Met Glu Leu Ser Ser Leu Arg Ser Glu Asp Thr Ala
                 85                  90                  95
Val Tyr Tyr Cys Ala Arg Tyr Tyr Asp Asp His Tyr Cys Leu Asp Tyr
            100                 105                 110
Trp Gly Gln Gly Thr Thr Val Thr Val Ser Ser Val Glu Gly Gly Ser
        115                 120                 125
Gly Gly Ser Gly Gly Ser Gly Gly Ser Gly Gly Val Asp Asp Ile Gln
    130                 135                 140
Met Thr Gln Ser Pro Ser Ser Leu Ser Ala Ser Val Gly Asp Arg Val
145                 150                 155                 160
Thr Ile Thr Cys Arg Ala Ser Ser Ser Val Ser Tyr Met Asn Trp Tyr
                165                 170                 175
Gln Gln Lys Pro Gly Lys Ala Pro Lys Leu Leu Ile Tyr Asp Thr Ser
            180                 185                 190
Lys Val Ala Ser Gly Val Pro Ser Arg Phe Ser Gly Ser Gly Ser Gly
        195                 200                 205
```

Thr Asp Tyr Thr Leu Thr Ile Ser Ser Leu Gln Pro Glu Asp Phe Ala
    210                 215                 220

Thr Tyr Tyr Cys Gln Gln Trp Ser Ser Asn Pro Leu Thr Phe Gly Gly
225                 230                 235                 240

Gly Thr Lys Val Glu Ile Lys Arg His His His His His His
            245                 250

<210> SEQ ID NO 140
<211> LENGTH: 672
<212> TYPE: DNA
<213> ORGANISM: Artificial Sequence
<220> FEATURE:
<223> OTHER INFORMATION: Synthetic

<400> SEQUENCE: 140
gatattcaga tgacccagag cccgagcagc ctgagcgcga gcgtgggcga tcgcgtgacc      60
attacctgcc gcgcgagcag cagcgtgagc tatatgaact ggtatcagcg taaaccgggc     120
aaagcgccga aactgctgat ttatgatacc agcaaagtgg cgagcggcgt gccgagccgc     180
tttagcggca gcggcagcgg caccgattat accctgacca ttagcagcct gcagccggaa     240
gattttgcga cctattattg ccagcagtgg agcagcaacc cgctgacctt tggcggcggc     300
accaaagtgg aaattaaacg caccgtggca gcacctagcg tgttcatctt tccccctcc      360 gacgagcagc tgaagtccgg cacagcctct gtggtgtgcc tgctgaacaa tttctatcca     420
cgcgaggcca aggtgcagtg gaaggtggat aacgccctgc agtctggcaa tagccaggag     480
tccgtgaccg agcaggactc taaggatagc acatactccc tgtcctctac cctgacactg     540
agcaaggccg attacgagaa gcacaagctg tatgcatgcg aggtgaccca ccagggcctg     600
agctccccag tgacaaagtc ttttaaccgg ggcgagtgtg cggcggctc ccaccaccac      660 caccaccact ga                                                         672

<210> SEQ ID NO 141
<211> LENGTH: 223
<212> TYPE: PRT
<213> ORGANISM: Artificial Sequence
<220> FEATURE:
<223> OTHER INFORMATION: Synthetic

<400> SEQUENCE: 141

Asp Ile Gln Met Thr Gln Ser Pro Ser Ser Leu Ser Ala Ser Val Gly
1               5                  10                  15

Asp Arg Val Thr Ile Thr Cys Arg Ala Ser Ser Ser Val Ser Tyr Met
            20                  25                  30

Asn Trp Tyr Gln Arg Lys Pro Gly Lys Ala Pro Lys Leu Leu Ile Tyr
        35                  40                  45

Asp Thr Ser Lys Val Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Leu Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser His His His His His His
    210                 215                 220

<210> SEQ ID NO 142
<211> LENGTH: 1350
<212> TYPE: DNA
<213> ORGANISM: Artificial Sequence
<220> FEATURE:
<223> OTHER INFORMATION: Synthetic

<400> SEQUENCE: 142
caggtgcagc tggtgcagag cggcgcggaa gtgaaaaaac cgggcgcgag cgtgaaagtg      60
agctgcaaag cgagcggcta cctttacc cgctatacca tgcattgggt gcgctatgcg       120
ccgggccagg gcctggaatg gatgggctat attaacccga ccgcggcta taccagctat     180
gcgcagaaat tcagggccg cgtgaccatg accaccgata aaagcaccag caccgtgtat      240
atggaactga gcagcctgcg cagcgaagat accgcggtgt attattgcgc gcgctattat     300
gatgatcatt attgcctgga ttattggggc cagggcacca ccgtgaccgt gagcagcgcc    360
tctacaaagg gacctagcgt gttcccactg gcaccctcct ctaagtccac ctctggagga    420
acagccgccc tgggatgcct ggtgaaggat tacttcccag gcccgtgac cgtgtcctgg     480
aactctggcg ccctgaccag cggagtgcac acatttcctg ccgtgctgca gagctccggc    540
ctgtactccc tgtctagcgt ggtgacagtg ccatcctcta gcctgggcac ccagacatat    600
atctgcaacg tgaatcacaa gccaagcaat accaaggtcg acaagaaggt ggagcccaag    660
tcctgtgata gaacccacac atgccccct tgtcctgcac cagagctgct gggaggacca     720
agcgtgttcc tgttccacc caagcctaag gacaccctga tgatctctcg gacccccagg    780
gtgacatgcg tggtggtgga cgtgagccac gaggatcccg aggtgaagtt taactggtac    840
gtggatggcg tggaggtgca caatgccaag accaagccca gggaggagca gtacaattcc    900
acctatcgcg tggtgtctgt gctgacagtg ctgcaccagg actggctgaa cggcaaggag   960
tataagtgca aggtgtccaa taaggccctg cccgcccta tcgagaagac aatctctaag   1020
gcaaagggac agcctcggga gccacaggtg tacaccctgc ctccatccag agatgagctg  1080
accaagaacc aggtgtctct gacatgtctg gtgaagggct tctatccctc tgacatcgcc  1140
gtggagtggg agagcaatgg ccagcctgag aacaattacg ataccacacc cctgtgctg   1200
gacagcgatg gctccttctt tctgtatagc gacctgacag tggataagtc cagatggcag  1260
cagggcaacg tgtttagctg ttccgtgatg cacgaggccc tgcacaatca ctacacccag  1320
aagtctctga gcctgtcccc cggcaagtaa                                     1350

<210> SEQ ID NO 143
<211> LENGTH: 449
<212> TYPE: PRT

<213> ORGANISM: Artificial Sequence
<220> FEATURE:
<223> OTHER INFORMATION: Synthetic

<400> SEQUENCE: 143

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Tyr Ala Pro Gly Gln Gly Leu Glu Trp Met
        35                  40                  45

Gly Tyr Ile Asn Pro Ser Arg Gly Tyr Thr Ser Tyr Ala Gln Lys Phe
    50                  55                  60

Gln Gly Arg Val Thr Met Thr Thr Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

-continued

```
Ser Asn Gly Gln Pro Glu Asn Tyr Asp Thr Thr Pro Pro Val Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```